US007445928B2

(12) United States Patent
Sanchez

(10) Patent No.: US 7,445,928 B2
(45) Date of Patent: Nov. 4, 2008

(54) BACTERIAL ARTIFICIAL CHROMOSOME CONSTRUCT ENCODING RECOMBINANT CORONAVIRUS

(75) Inventor: Luis Enjuanes Sanchez, Madrid (ES)

(73) Assignee: Consejo Superior de Investigationes Cientificas, Madrid (ES)

( * ) Notice: Subject to any disclaimer, the term of this patent is extended or adjusted under 35 U.S.C. 154(b) by 0 days.

(21) Appl. No.: 10/148,669

(22) PCT Filed: Nov. 30, 2000

(86) PCT No.: PCT/EP00/12063

§ 371 (c)(1),
(2), (4) Date: Jun. 3, 2002

(87) PCT Pub. No.: WO01/39797

PCT Pub. Date: Jun. 7, 2001

(65) Prior Publication Data

US 2004/0086846 A1 May 6, 2004

(30) Foreign Application Priority Data

Dec. 3, 1999 (ES) .................................. 9902673

(51) Int. Cl.
C12N 15/00 (2006.01)
A61K 39/215 (2006.01)
(52) U.S. Cl. ................................. 435/320.1; 424/221.1
(58) Field of Classification Search .............. 435/320.1, 435/325, 235.1; 536/23.1; 424/204.1
See application file for complete search history.

(56) References Cited

U.S. PATENT DOCUMENTS

| 5,288,641 | A | 2/1994 | Roizman |
| 5,501,979 | A | 3/1996 | Geller et al. |
| 5,585,096 | A | 12/1996 | Martuza et al. |
| 5,658,724 | A | 8/1997 | DeLuca |
| 5,776,745 | A | 7/1998 | Ketner et al. |
| 6,277,621 | B1 | 8/2001 | Horsburgh et al. |
| 6,593,111 | B2 | 7/2003 | Baric et al. |

FOREIGN PATENT DOCUMENTS

| EP | 0 453 242 A1 | 10/1991 |
| WO | WO 90/09441 | 8/1990 |
| WO | WO 95/03400 | 2/1995 |
| WO | WO 96/04394 | 2/1996 |
| WO | WO 96/15779 | 5/1996 |
| WO | WO 96/26267 | 8/1996 |
| WO | WO 97/05263 | 2/1997 |
| WO | WO 97/30732 | 8/1997 |
| WO | WO 97/34008 | 9/1997 |
| WO | WO 99/06582 | 2/1999 |
| WO | WO 99/43842 | 9/1999 |
| WO | WO 01/39797 | 6/2001 |

OTHER PUBLICATIONS

P. Ahlquist et al., "Multicomponent RNA Plant Virus Infection Derived From Cloned Viral cDNA", Proc. Natl. Acad. Sci. USA, Nov. 1984, pp. 7066-7070, vol. 81, The National Academy of Sciences, Washington, DC.

F. Almazan et al., "Engineering the Largest RNA Virus Genome as an Infectious Bacterial Artificial Chromosome", Proc. Natl., Acad. Sci. USA, May 2000, pp. 5516-5521, vol. 97, No. 10, The National Academy of Sciences, Washington, DC.

F. Ascenzioni et al., "Mammalian Artificial Chromosomes-Vectors for Somatic Gene Therapy", Cancer Letters, 1997, pp. 135-142, vol. 118, Elsevier Science Ireland Ltd., Ireland.

M.L. Ballesteros et al., "Two Amino Acid Changes at the N-Terminus of Transmissible Gastroenteritis Coronavirus Spoke Protein Result in the Loss of Enteric Tropsim", Virology, 1997, pp. 378-388, vol. 227, Academic Press, Inc., San Diego, CA.

M.D. Baron et al., "Rescue of Rinderpest Virus From Cloned cDNA", J. Virol., Feb. 1997, pp. 1265-1271, vol. 71, No. 2, American Society for Microbiology, Washington, DC.

G. Bilbao et al., "Adenoviral/Retroviral Vector Chimeras: A Novel Strategy to Achieve High-Efficiency Stable Transduction in vivo", The FASEB Journal, Jul. 1997, pp. 624-634, vol. 11, FASEB, Bethesda, MD.

J.-C. Boyer et al., "Infectious Transcripts and cDNA Clones of RNA Viruses", Virology, 1994, pp. 415-426, vol. 198, Academic Press, Inc., San Diego, CA.

Burke, "Special Section: Yeast Artificial Chromosome Cloning; YAC Cloning: Options and Problems", Genet. Anal. Tech. Appl., 1990, pp. 94-99, vol. 7, No. 5, Elsevier Science Publishing Co., Inc., NY, NY.

R. Casais et al., "Reverse Genetics System for the Avian Coronavirus Infectious Bronchitis Virus", J. Virol., Dec. 2001, pp. 12359-12369, vol. 75, No. 24, ASM Press, Washington, DC.

(Continued)

Primary Examiner—Stacy B Chen
(74) Attorney, Agent, or Firm—Sharon E. Crane; Bingham McCutchen, LLP

(57) ABSTRACT

The present invention relates to methods of preparing a DNA comprising steps, wherein (a) a DNA comprising a full length copy of the genomic RNA (gRNA) or an RNA virus; or (b) a DNA comprising one or several fragments of a gRNA of an RNA virus, which fragments code for an RNA dependent RNA polymerase and at least one structural or non-structural protein; or (c) a DNA having a homology of at least 60% to the sequences of (a) or (b); is cloned into a bacterial artificial chromosome (BAC). Additionally, DNAs are provided, which comprise sequences derived from the genomic RNA (gRNA) of a coronavirus which sequences have a homology of at least 60% to the natural sequence of the virus and code for an RNA dependent RNA polymerase and at least one structural or no-structural protein, wherein a fragment of said DNA is capable of being transcribed into RNA which RNA can be assembled to a virion. Further, the use of these nucleic acids for preparation of viral RNA or virions as well as pharmaceutical preparations comprising these DNAs, viral RNAs or virions is disclosed.

5 Claims, 25 Drawing Sheets

OTHER PUBLICATIONS

R.-Y. Chang et al., "A cis-Acting Function for the Coronavirus Leader in Defective Interfering RNA Replication", J. Virol., Dec. 1994, pp. 8223-8231, vol. 68, No. 12, American Society for Microbiology, Washington, DC.

H.C. Chiou et al., "Mutations in the Herpes Simplex Virus DNA-Binding Protein Gene Leading to Altered Sensitivity to DNA Polymerase Inhibitors", Virology, 1985, pp. 213-226, vol. 145, Academic Press, Inc., San Diego, CA.

P. L. Collins et al., "Production of Infectious Human Respiratory Syncytial Virus From Cloned cDNA Confirms an Essential Role for the Transcription Elongation Factor From the 5' Proximal Open Reading Frame of the M2 mRNA in Gene Expression and Provides a Capability for Vaccine Development", Proc. Natl. Acad. Sci. USA, Dec. 1995, pp. 11563-11567, vol. 92, The National Academy of Sciences, Washington, DC.

N.L. Davis et al., "In vitro Synthesis of Infectious Venezuelan Equine Encephalitis Virus RNA From a cDNA Clone: Analysis of a Viable Deletion Mutant", Virology, 1989, pp. 189-204, vol. 171, Academic Press, Inc., San Diego, CA.

T.W. Dubensky, Jr. et al., "Sindbis Virus DNA-Based Expression Vectors : Utility For in vitro and in vivo Gene Transfer", J. Virol., Jan. 1996, pp. 508-519, vol. 70, No. 1, American Society for Microbiology, Washington, DC.

A.P. Durbin et al., "Recovery of Infectious Human Parainfluenza Virus Type 3 From cDNA", Virology, 1997, pp. 323-332, vol. 235, Academic Press, Inc., San Diego, CA.

L. Enjuanes et al., "Coronaviruses and *Arteriviruses*", 1998, Plenum Press, New York.

L. Enjuanes et al., "Molecular Basis of Transmissible Gastroenteritis Virus Epidemiology", In The *Coronaviridae*, 1995, S.G. Siddell (Ed.) Plenum Press, New York, pp. 337-376.

I. Frolov et al., "Alphavirus-Based Expression Vectors: Strategies and Applications", Proc. Natl. Acad. Sci. USA, Oct. 1996, pp. 11371-11377, vol. 93, The National Academy of Sciences, Washington, DC.

P.J. Gage et al., "A cell-Free Recombination System for Site-Specific Integration of Multigenic Shuttle Plasmids Into the Herpes Simplex Virus Type 1 Genome", J. Virol., Sep. 1992, pp. 5509-5515, vol. 66, No. 9, American Society for Microbiology, Washington, DC.

D. Garcin et al., "A highly Recombinogenic System for the Recovery of Infectious Sendai Paramyxovirus From cDNA: Generation of a Novel Copy-Back Nondefective Interfering Virus", EMBO J., 1995, pp. 6087-6094, vol. 14, No. 24, Oxford University Press, Oxford, UK.

U. Geigenmüller et al., "Construction of a Genome-Length cDNA Clone for Human Astrovirus Serotype 1 and Synthesis of Infectious RNA Transcripts", Feb. 1997, J. Virol., pp. 1713-1717, vol. 71, No. 2, American Society for Microbiology, Washington, DC.

B.C. Horsburgh et al., "Allele Replacement: An Application That Permits Rapid Manipulation of Herpes Simplex Virus Type 1 Genomes", Gene Therapy, May 1999, pp. 922-930, vol. 6, No. 5, Stockton Press, Hampshire, UK.

B. Hsue et al., "Insertion of a New Transcriptional Unit Into the Genome of Mouse Hepatitis Virus", J. Virol., Jul. 1999, pp. 6128-6135, vol. 73, No. 7, American Society for Microbiology, Washington, DC.

A. Izeta et al., "Replication and Packaging of Transmissible Gastroenteritis Coronavirus-Derived Synthetic Minigenomes", J. Virol., Feb. 1999, pp. 1535-1545, vol. 73, No. 2, American Society for Microbiology, Washington, DC.

G. Ketner et al., "Efficient Manipulation of the Human Adenovirus Genome as an Infectious Yeast Artificial Chromosome Clone", Proc. Natl. Acad. Sci. USA, Jun. 1994, pp. 6186-6190, vol. 91, The National Academy of Sciences, Washington, DC.

U.-J. Kim et al., "Stable Propagation of Cosmid Sized Human DNA Inserts in an F Factor Based Vector", Nucleic Acids Res., Mar. 11, 1992, pp. 1083-1085, vol. 20, No. 5, Oxford University Press, Oxford, UK.

L. Kuo et al., "Retargeting of Coronavirus by Substitution of the Spike Glycoprotein Ectodomain: Crossing the Host Cell Species Barrier", J. Virol., Feb. 2000, pp. 1393-1406, vol. 74, No. 3, ASM Press, Washington, DC.

M.C. Lai, "The Making of Infectious Viral RNA: No Size Limit in Sight", Proc. Natl., Acad. Sci. USA, May 2000, pp. 5025-5027, vol. 97, No. 10, The National Academy of Sciences, Washington, DC.

C.-J. Lai et al., "Infectious RNA Transcribed From Stably Cloned Full-Length cDNA of Dengue Type 4 Virus", Proc. Natl. Acad. Sci. USA, Jun. 1991, pp. 5139-5143, vol. 88, The National Academy of Sciences, Washington, DC.

M.M.C. Lai et al., "The Molecular Biology of Coronaviruses", Adv. Virus Res., 1997, pp. 1-100, vol. 48, Academic Press.

M.M.C. Lai et al., "Coronavirus: How a Large RNA Viral Genome is Replicated and Transcribed", Infect. Agents Dis., 1994, pp. 98-105, vol. 3, No. 2/3, Raven Press Ltd., NY.

P. Liljeström, "Alphavirus Expression Systems", Curr. Opin. Biotech., 1994, pp. 495-500, vol. 5, Current Biology Ltd., London, UK.

P. Liljeström et al., "A New Generation of Animal Cell Expression Vectors Based on the Semliki Forest Virus Replicon", Bio/Technology, Dec. 1991, pp. 1356-1361, vol. 9, Nature Publishing Co., Bleecker, NY.

W. Luytjes et al., "Amplification, Expression, and Packaging of a Foreign Gene by Influenza Virus", Cell, Dec. 22, 1989, pp. 1107-1113, vol. 59, Cell Press, Cambridge, Massachusetts.

C.W. Mandl et al., "Infectious cDNA Clones of Tick-Borne Encephalitis Virus European Subtype Prototypic Strain Neudoerfl and High Virulence Strain Hypr", J. Gen. Virol, 1997, pp. 1049-1057, vol. 78, SGM, UK.

T. Maniatis et al., "Molecular Cloning: A Laboratory Manual", 1989, Cold Spring Harbour Laboratory Press, New York.

P.S. Masters, "Reverse Genetics of the Largest RNA Viruses", Advances in Virus Research, 1999, pp. 245-246, vol. 53, Academic Press, San Diego, CA.

A. Méndez et al., "Molecular characterization of Transmissible Gastroenteritis Coronavirus Defective Inferfering Genomes: Packaging and Heterogeneity", Virology, 1996, pp. 495-507, vol. 217, Academic Press, Inc., San Diego, CA.

M. Messerle et al., "Reconstitution of a Recombinant Cytomegalovirus From Two Fragments Cloned Into Bacterial Artificial Chromosomes", J. Mol. Med., 1996, pp. vol. 74, No. 4, Abstracts B1-B11, Springer-Verlag, Berlin, Germany.

M. Messerle et al., "Cloning and Mutagenesis of a Herpesvirus Genome as an Infectious Bacterial Artificial Chromosome", Proc. Natl. Acad. Sci. USA, 1997, pp. 14759-14763, vol. 94, The National Academy of Sciences, Washington, DC.

Monaco et al., Tibtech, Jul. 1994, pp. 280-286, vol. 12.

Z. Penzes et al., "Complete Genome Sequence of Transmissible Gastroenteritis Coronavirus PUR46-MAD Clone and Evolution of the Purdue Virus Cluster", Virus Genes, 2001, pp. 105-118, vol. 23, No. 1, Kluwer Academic Publishers, The Netherlands.

P. Pushko et al., "Replicon-Helper Systems From Attenuated Venezuelan Equine Encephalitis Virus: Expression of Heterologous Genes in vitro and Immunization Against Heterologous Pathogens in vivo", Virology, 1997, pp. 389-401, vol. 239, Academic Press, Inc., San Diego, CA.

V.R. Racaniello et al., "Cloned Poliovirus Complementary DNA is Infectious in Mammalian Cells", Science, 1981, pp. 916-919, vol. 214, American Association for the Advancement of Science, Washington, DC.

F. Radecke et al., "Rescue of Measles Viruses From Cloned DNA", EMBO J., 1995, pp. 5773-5784, vol. 14, No. 23, Oxford University Press, Oxford, UK.

C.M. Rice et al., "Transcription of Infectious Yellow Fever RNA From Full-Length cDNA Templates Produced by in vitro Ligation", New Biologist, Dec. 1989, pp. 285-296, vol. 1, No. 3, W.B. Saunders Co.

C.M. Rice et al., "Production of Infectious RNA Transcripts From Sindbis Virus cDNA Clones: Mapping of Lethal Mutations, Rescue of a Temperature-Sensitive Marker, and in vitro Mutagenesis to Generate Defined Mutants", J. Virol., Dec. 1987, pp. 3809-3819, vol. 61, No. 12, American Society for Microbiology, Washington, DC.

C.M. Rice et al., "Synthesis, Cleavage, and Sequence Anlysis of DNA Complementary to the 26 S Messenger RNA of Sindbis Virus", J. Mol. Biol., 1981, pp. 315-340, vol. 150, Academic Press Inc., London, UK.

N. Ruggli et al., "Nucleotide Sequence of Classical Swine Fever Virus Strain Alfort/187 and Transciption of Infectious RNA From Stably Cloned Full-Length cDNA", J. Virol., Jun. 1996, pp. 3478-3487, vol. 70, No. 6, American Society for Microbiology, Washington, DC.

Y. Saeki et al., "Herpes Simplex Virus Type 1 DNA Amplified as Bacterial Artificial Chromosome in *Eschericia coli*: Rescue of Replication-Competent Virus Progeny and Packaging of Amplicon Vectors", Human Gene Therapy, Dec. 10, 1998, pp. 2787-2794, vol. 9, Mary Ann Liebert, Inc., Larchmont, NY.

C.M. Sánchez et al., "Targeted Recombination Demonstrates that the Spike Gene of Transmissible Gastroenteritis Coronavirus is a Determinant of its Enteric Tropism and Virulence", J. Virol., Sep. 1999, pp. 7607-7618, vol. 73, No. 9, ASM Press, Washington, DC.

C.M. Sánchez et al., "Antigenic Homology Among Coronaviruses Related to Transmissible Gastroenteritis Virus", Virology, 1990, pp. 410-417, vol. 174, Academic Press, Inc., San Diego, CA.

C.M. Sánchez et al., "Genetic Evolution and Tropism of Transmissible Gastroenteritis Coronaviruses", Virology, 1992, pp. 92-105, vol. 190, Academic Press, Inc., San Diego, CA.

S.G. Sawicki et al., "Coronavirus Transcription: Subgenomic Mouse Hepatitis Virus Replicative Intermediates Function in RNA Synthesis", J. Virol., Mar. 1990, pp. 1050-1056, vol. 64, No. 3, American Society for Microbiology, Washington, DC.

M.J. Schnell et al., "Infectious Rabies Viruses From Cloned cDNA", EMBO J., Sep. 15, 1994, pp. 4195-4203, vol. 13, No. 18, Oxford University Press, Oxford, UK.

P.B. Sethna et al., "Coronavirus Subgenomic Minus-Strand RNAs and the Potential for mRNA Replicons", Proc. Natl. Acad. Sci. USA, Jul. 1989, pp. 5626-5630, vol. 86, The National Academy of Sciences, Washington, DC.

H. Shizuya et al., "Cloning and Stable Maintenance of 300-Kilobase-Pair Fragments of Human DNA in *Escherichia coli* Using an F-Factor-Based Vector", Proc. Natl. Acad. Sci. USA, Sep. 1992, pp. 8794-8797, vol. 89, The National Academy of Sciences, Washington, DC.

S.G. Siddell, The Coronaviridae, 1995, Plenum Press, New York.

C. Smerdou et al., "Non-Viral Amplification Systems for Gene Transfer: Vectors Based on Alphaviruses", Curr. Opin. Mol. Therap., 1999, pp. 244-251, vol. 1, No. 2, Current Drugs Ltd., London, UK.

R.R. Spaete et al., "Insertion and Deletion Mutagenesis of the Human Cytomegalovirus Genome", Proc. Natl. Acad. Sci. USA, Oct 1987, pp. 7213-7217, vol. 84, The National Academy of Sciences, Washington, DC.

M. Taniguchi et al., "Specific Suppressive Factors Produced by Hybridomas Derived From the Fusion of Enriched Suppressor T Cells and A T Lymphoma Cell Line", J. Exp. Med., 1978, pp. 373-382, vol. 148, The Rockefeller University Press, NY, NY.

V. Thiel et al., "Infectious RNA Transcribed in vitro From a cDNA Copy of the Human Coronavirus Genome Cloned in Vaccinia Virus", J. Gen. Virol., 2001, pp. 1273-1281, vol. 82, Society for General Microbiology, Great Britain.

R.G. Van Der Most et al., "Coronavirus Replication, Transcription, and RNA Recombination", *In* The Coronaviridae, 1995, pp. 11-31, S.G. Siddell (Ed.), Plenum Press, New York.

K. Wang et al., "Complete Nucleotide Sequence of Two Generations of a Bacterial Artificial Chromosome Cloning Vector", BioTechniques, Dec. 1997, pp. 992-994, vol. 23, No. 6.

S.-S. Woo et al., "Construction and Characterization of a Bacterial Artificial Chromosome Library of *Sorghum bicolor.*", Nucleic Acids Res., 1994, pp. 4922-4931, vol. 22, No. 23, Oxford University Press, Oxford, UK.

X. Yang et al., "Homologous Recombination Based Modification in *Escherchia coli* and Germline Transmission in Transgenic Mice of a Bacterial Artificial Chromosome", Nature Biotechnology, Sep. 1997, pp. 859-865, vol. 15, Nature America Inc., NY, NY.

X. Zhang et al., "Coronavirus Leader RNA Regulates and Initiates Subgenomic mRNA Transcription Both in *trans* and in *cis*", J. Virol., Aug. 1994, pp. 4738-4746, vol. 68, No. 8, American Society for Microbiology, Washington, DC.

Gritsun, T.S. et al., "Infectious Transcripts of Tick-Borne Encephalitis Virus, Generated in Days by RT-PCR," Virology, 1995, pp. 611-618, Academic Press, Inc.

Herold, J. et al., "A Strategy for the Generation of Infectious RNAs and Autonomously Replicating RNAs Based on the HCV 229E Genome," Adv. Exp. Med. Biol., 1998, pp. 265-268, vol. 440, Plenum Press, New York.

Hurrelbrink, Robert J. et al., "Characterization of Infectious Murray Valley encephalitis virus derived from a stably cloned genome-length cDNA," J. Gen. Virology, 1999, pp. 3115-3125, vol. 80, Great Britain.

Kapoor, Mini et al., "Synthesis and characterization of an infectious dengue virus type-2 RNA genome (New Guinea C strain)," Gene, 1995, pp. 175-180, vol. 162, Elsevier Science B.V.

Mendez, Ernesto et al., "Infectious Bovine Viral Diarrhea Virus (Strain NADL) RNA from Stable cDNA Clones: a Cellular Insert Determines NS3 Production and Viral Cytopathogenicity," J. Virology, Jun. 1998, pp. 4737-4745, vol. 72, No. 6, Amer. Soc. For Microbiology.

Moormann, R.J.M. et al., "Infectious RNA Transcribed from an Engineered Full-Length cDNA Template of the Genome of a Pestivirus," J. Virology, Feb. 1996, pp. 763-770, vol. 70, No. 2, Ameri. Soc. For Microbiology.

Penzes, Zoltan et al., "Progress Towards the Construction of a Transmissible Gastroenteritis Coronavirus Self-Replicating RNA Using A Two-Layer Expression System," Adv. Exp. Med. Biol., 1998, pp. 319-325, vol. 440, Plenum Press, New York.

Penzes et al., "Construction and expression of a TGEV self-replicating RNA," Poster at the VIIth International Symposium on Coronaviruses and Arteriviruses, May 10-15, 1997, Segovia, Spain.

Polo, Stephanie et al., "Infectious RNA Transcripts from Full-Length Dengue Virus Type 2 cDNA Clones Made in Yeast," J. Virology, Jul. 1997, pp. 5366-5374, vol. 71, No. 7, Amer. Soc. For Microbiology.

Sumiyoshi, Hideo et al., "Infectious Japanese Encephalitis Virus RNA Can Be Synthesized from In Vitro-Ligated cDNA Templates," J. Virology, Sep. 1992, pp. 5425-5431, vol. 66, No. 9, Amer. Soc. For Microbiology.

Tellier, Raymond et al., "Amplification of the full-length hepatitis A virus genome by long reverse transcription-PCR and Transcription of Infectious RNA directly from the amplicon," PNAS, Apr. 1996, pp. 4370-4373, vol. 93, Genetics.

Tellier, Raymond et al., "Long PCR and Its Application to Hepatitis Viruses: Amplification of Hepatitis A, Hepatitis B, and Hepatitis C Virus Genomes," J. Clin. Microbiol., Dec. 1996, pp. 3085-3091, vol. 34, No. 12.

Thiel, Volker et al., "Effective Amplification of 20-kb DNA by Reverse Transcription PCR," Analytical Biochem., 1997, pp. 62-70, vol. 252, Academic Press.

Thiel, V. et al, "Reverse Genetics of Coronaviruses Using Vaccinia Virus Vectors," 2005, pp. 199-227, vol. 287, Springer-Verlag.

Yanagi, Masayuki et al., "Transcripts from a single full-length CDNA clone of hepatitis C virus are infectious when directly transfected into the liver of a chimpanzee," PNAS, Aug. 1997, pp. 8738-8743, vol. 94, Medical Sciences.

Godet, Murielle et al., "Major Receptor-Binding and Neutralization Determinants Are Located within the Same Domain of the Transmissible Gastroenteritis Virus (Coronavirus) Spike Protein," Jnl. of Virology, Dec. 1994, pp. 8008-8016, vol. 68, No. 12, American Society for Microbiology.

Kolb, Andreas F. et al., "Identification of residues critical for the human coronavirus 229E receptor function of human aminopeptidase N," Jnl. of General Virology, 1997, pp. 2795-2802, vol. 78, Great Britain.

Krempl, Christine et al., "Point Mutations in the S Protein Connect the Sialic Acid Binding Activity with the Enteropathogenicity of Transmissible Gasteroenteritis Coronavirus," Jnl. of Virology, Apr. 1997, pp. 3285-3287, vol. 71, No. 4, American Society for Microbiology.

Salanueva, Inigo J. et al., "Structural Maturation of the Transmissible Gastroenteritis Coronavirus," Jnl. of Virology, Oct. 1999, pp. 7952-7964, vol. 73, No. 10, American Society for Microbiology.

International Search Report, May 19, 2003, PCT ES 03/0008.

International Preliminary Examination Report of WO 01/39797 dated Mar. 27, 2002.

First Office Action from EP Application 04 007 406.4-1223, dated Nov. 7, 2005.

Enjuanes et al., "*Coronavirus derived expression systems*," 88 Journal of Biotechnology 183-204 (2001).

Yount et al., "*Systematic Assembly of a Full-Length Infections cDNA of Mouse Hepatitis Virus Strain A59*," 72(21) Journal of Virology 11065-11078 (2002).

St-Jean et al., "*Genetic evolution of human coronavirus OC43 in neural cell culture*," X Int. Nidovirus Symp.—Colorado Springs—USA, Jun. 25-30, 2005.

Almazán et al., "*Identification of essential genes as a strategy to select a SARS candidate vaccine using a SARS-VOV infectious cDNA clone*," X. Int. Nidovirus Symp. Colorado Springs, USA, Jun. 25-30, 2005.

Glossary term "Clone," In Lewin: Genes VII NY: Oxford Univ. Press 955 (2000).

St-Jean et al., "*Recovery of a neurovirulent human coronavirus OC43 from an infectious cDNA clone*,"80 J. Virol. 3670-4 (Apr. 2006).

Almazán et al., "*Construction of a severe acute respiratory syndrome coronavirus infectious cDNA clone and a replicon to study coronavirus RNA synthesis*," 80(21) J. Virol. 1-7 (Nov. 2006).

Almazán et al., "*The nucleoprotein is required for efficient coronavirus genome replication*," 78 J. Virol. 12683-8 (Nov. 2004).

Somia et al., "Gene Therapy: Trials and Tribulations," *Nature Review*, Nov. 2000, vol. 1, pp. 91-99.

FIGURE 1
FIGURE 1A
FIGURE 1B
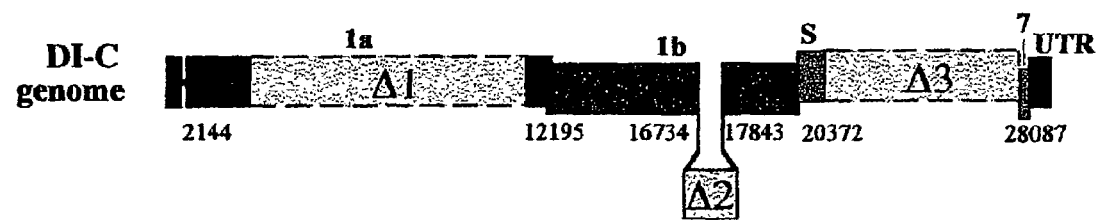
FIGURE 1C
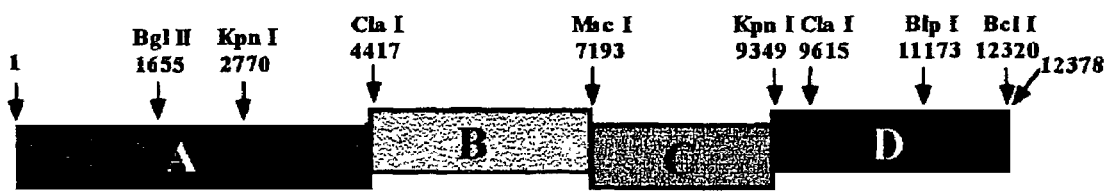

pBeloBAC

FIGURE 6
FIGURE 6A
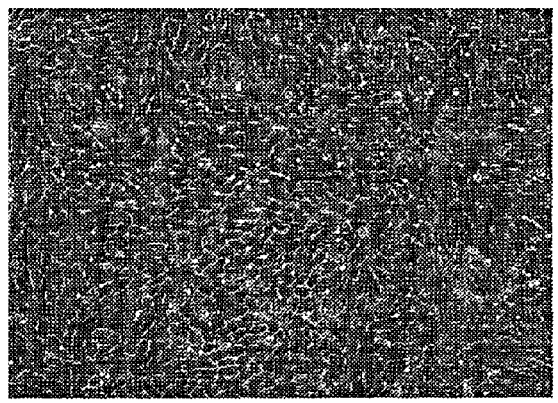
FIGURE 6B
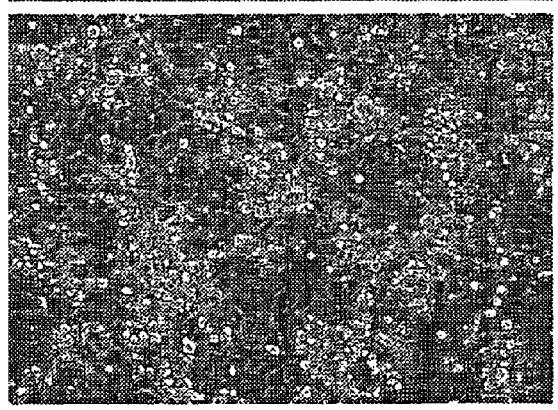
FIGURE 6C
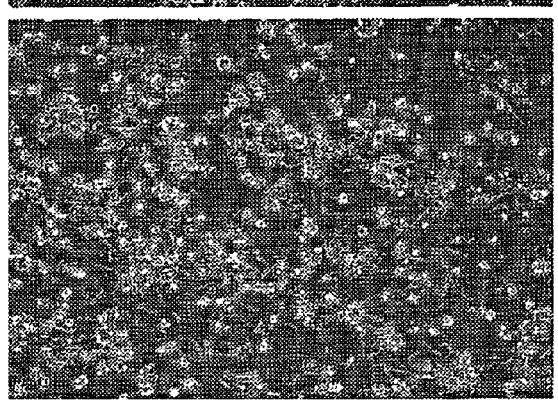

FIGURE 9
FIGURE 9A
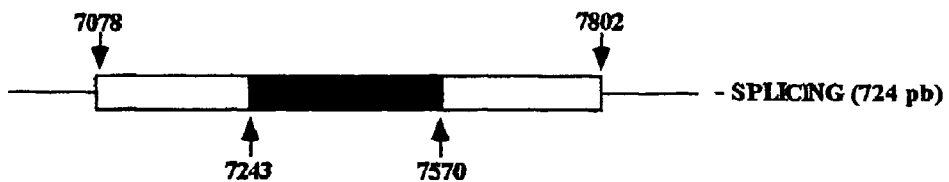
FIGURE 9B
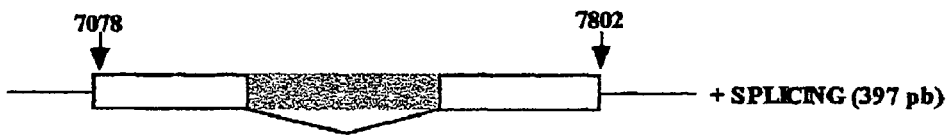
FIGURE 9C
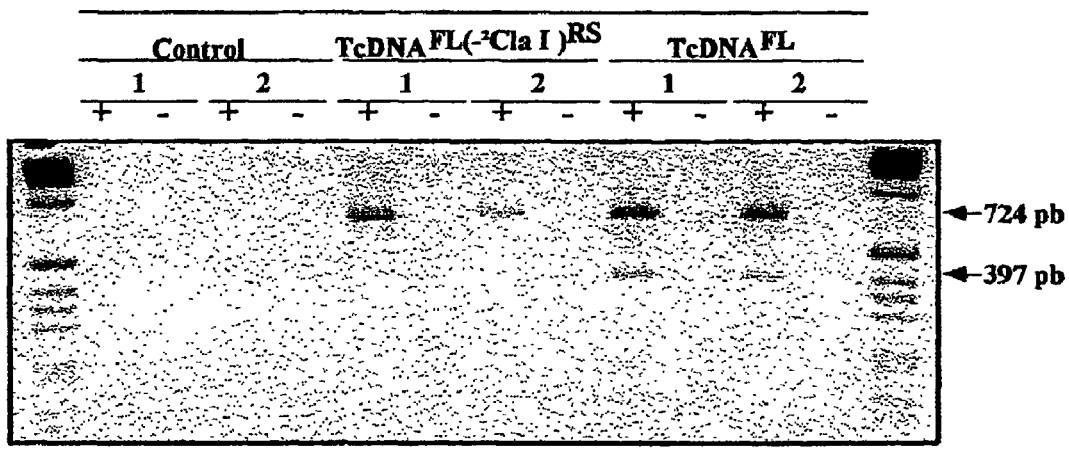
FIGURE 9D
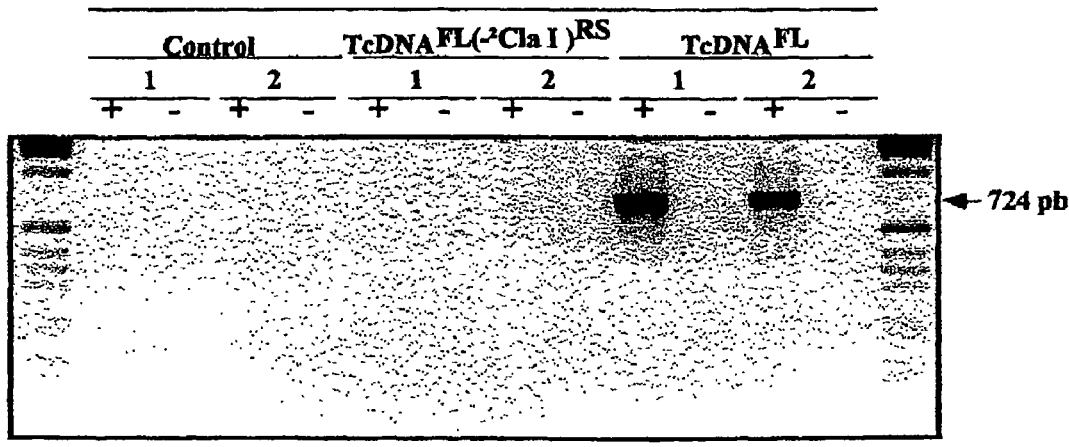

FIGURE 10

FIGURE 11
FIGURE 11A
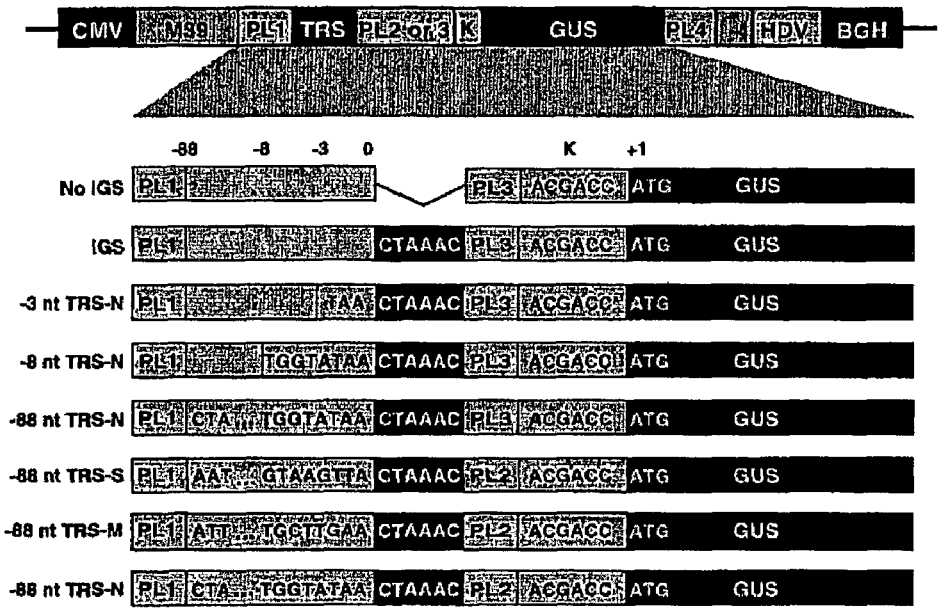
FIGURE 11B
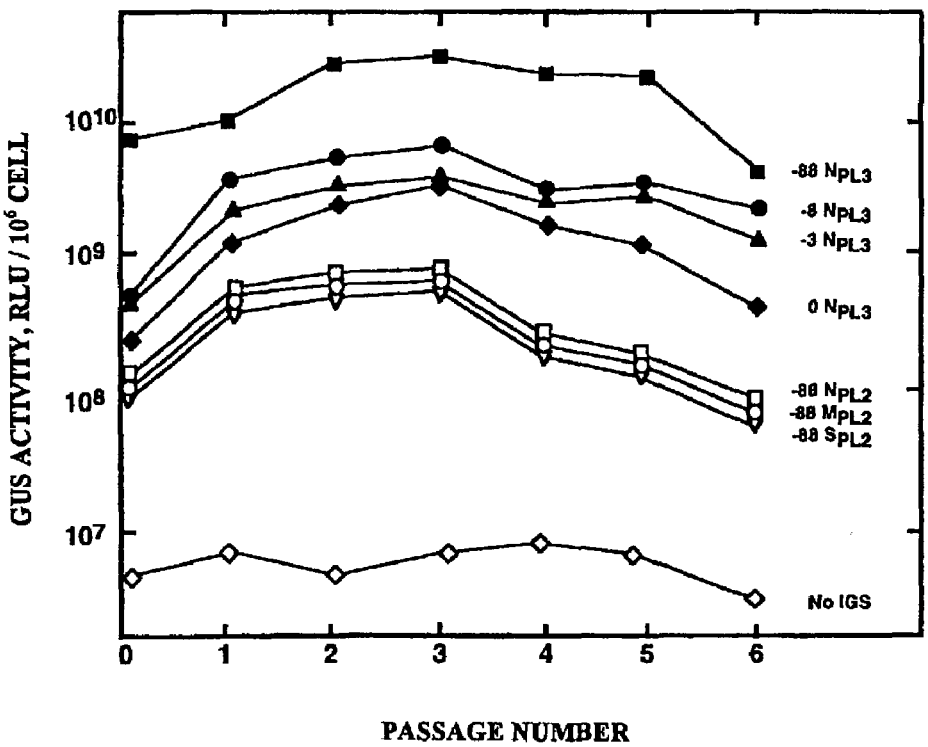

FIGURE 12
FIGURE 12A
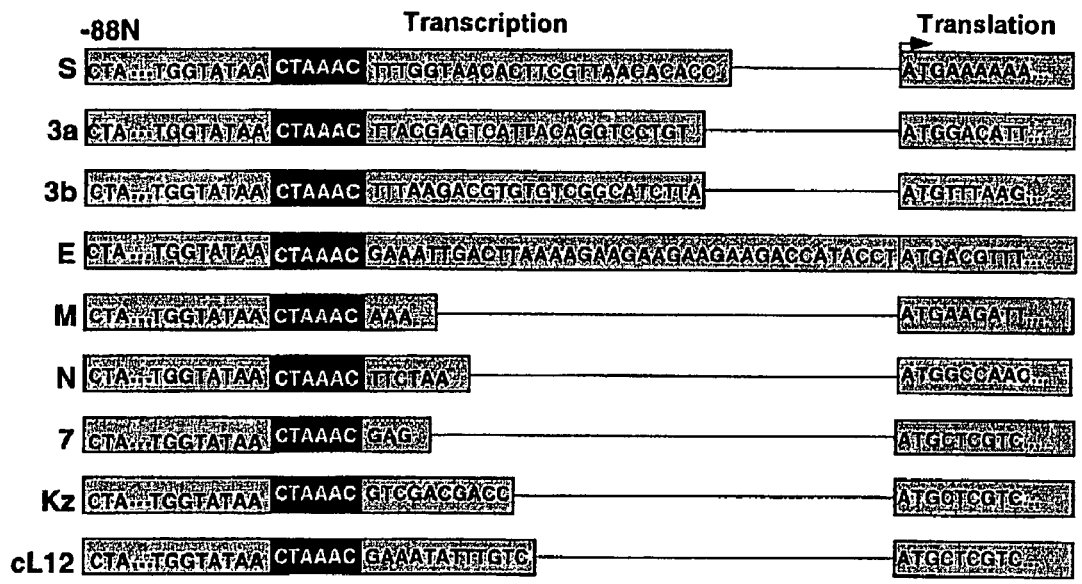
FIGURE 12B
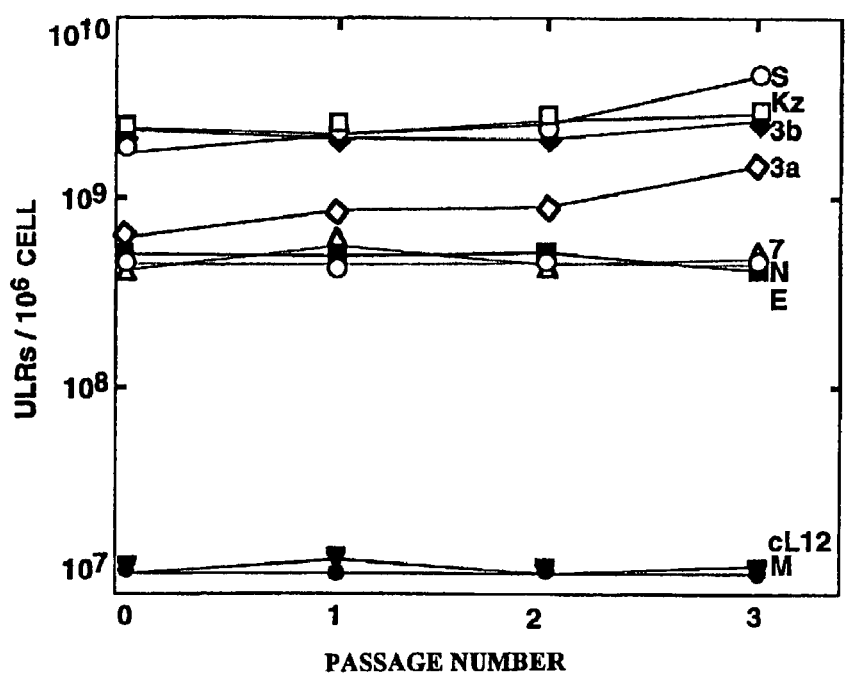

FIGURE 13
FIGURE 13A
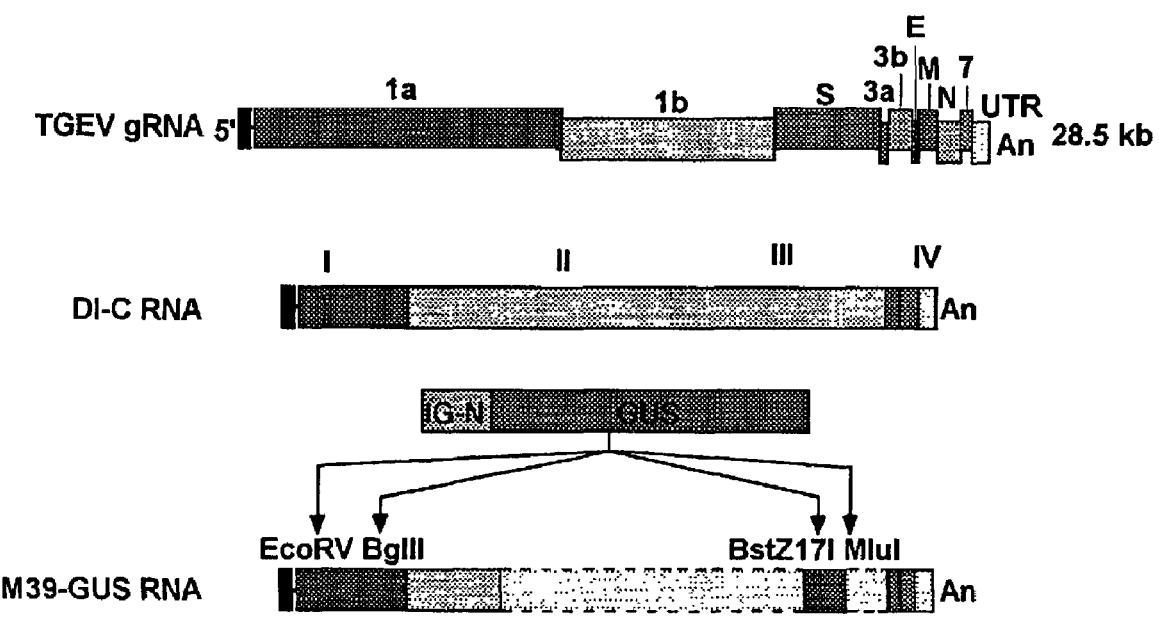
FIGURE 13B
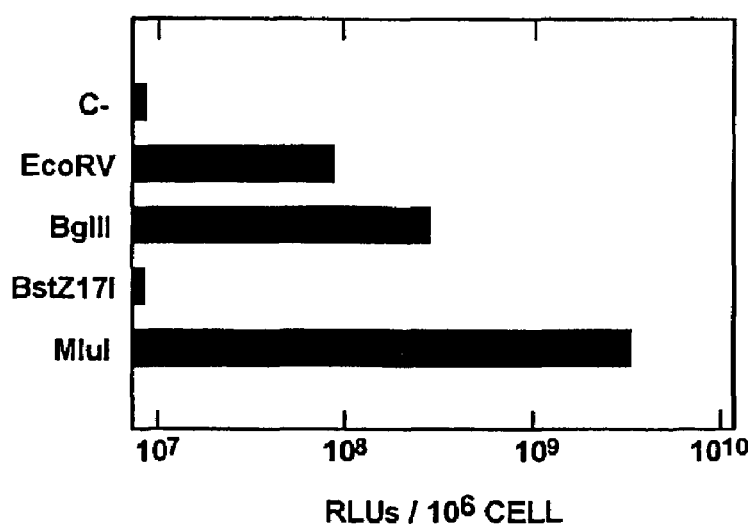

FIGURE 14-1

```
ACTTTTAAAG TAAAGTGAGT GTAGCGTGGC TATATCTCTT CTTTTACTTT AACTAGCCTT   60
GTGCTAGATT TTGTCTTCGG ACACCAACTC GAACTAAACG AAATATTTGT CTTTCTATGA  120
AATCATAGAG GACAAGCGTT GATTATTTCC ATTCAGTTTG GCAATCACTC CTTGGAACGG  180
GGTTGAGCGA ACGGTGCAGT AGGGTTCCGT CCCTATTTCG TAAGTCGCCT AGTAGTAGCG  240
AGTGCGGTTC CGCCCGTACA ACGTTGGGTA GACCGGGTTC CGTCCTGTGA TCTCCCTCGC  300
CGGCCGCCAG GAGAATGAGT TCCAAACAAT TCAAGATCCT TGTTAATGAG GACTATCAAG  360
TCAACGTGCC TAGTCTTCCT ATTCGTGACG TGTTACAGGA AATTAAGTAC TGCTACCGTA  420
ATGGATTTGA GGGCTATGTT TTCGTACCAG AATACTGTCG TGACCTAGTT GATTGCGATC  480
GTAAGGATCA CTACGTCATT GGTGTTCTTG GTAACGGAGT AAGTGATCTT AAACCTGTTC  540
TTCTTACCGA ACCCTCCGTC ATGTTGCAAG GCTTTATTGT TAGAGCTAAC TGCAATGGCG  600
TTCTTGAGGA CTTTGACCTT AAAATTGCTC GCACTGGCAG AGGTGCCATA TATGTTGATC  660
AATACATGTG TGGTGCTGAT GGAAAACCAG TCATTGAAGG CGATTTTAAG GACTACTTCG  720
GTGATGAAGA CATCATTGAA TTTGAAGGAG AGGAGTACCA TTGCGCTTGG ACAACTGTGC  780
GCGATGAGAA ACCGCTGAAT CAGCAAACTC TCTTTACCAT TCAGGAAATC CAATACAATC  840
TGGACATTCC TCATAAATTG CCAAACTGTG CTACTAGACA TGTAGCACCA CCAGTCAAAA  900
AGAACTCTAA AATAGTTCTG TCTGAAGATT ACAAGAAGCT TTATGATATC TTCGGATCAC  960
CCTTTATGGG AAATGGTGAC TGTCTTAGCA AATGCTTTGA CACTCTTCAT TTTATCGCTG 1020
CTACTCTTAG ATGCCCGTGT GGTTCTGAAA GTAGCGGCGT TGGAGATTGG ACTGGTTTTA 1080
AGACTGCCTG TTGTGGTCTT TCTGGCAAAG TTAAGGGTGT CACTTTGGGT GATATTAAGC 1140
CTGGTGATGC TGTTGTCACT AGTATGAGCG CAGGTAAGGG AGTTAAGTTC TTTGCCAATT 1200
GTGTTCTTCA ATATGCTGGT GATGTTGAAG GTGTCTCCAT CTGGAAAGTT ATTAAAACTT 1260
TTACAGTTGA TGAGACTGTA TGCACCCCTG GTTTTGAAGG CGAATTGAAC GACTTCATCA 1320
AACCTGAGAG CAAATACACTA GTTGCATGCA GCGTTAAAAG AGCATTCATT ACTGGTGATA 1380
TTGATGATGC TGTACATGAT TGTATCATTA CAGGAAAATT GGATCTTAGT ACCAACCTTT 1440
TTGGTAATGT TGGTCTATTA TTCAAGAAGA CTCCATGGTT TGTACAAAAG TGTGGTGCAC 1500
TTTTTGTAGA CGCTTGGAAA GTAGTAGAGG AGCTTTGTGG TTCACTCACA CTTACATACA 1560
AGCAAATTTA TGAAGTTGTA GCATCACTTT GCACTTCTGC TTTTACGATT GTAAACTACA 1620
AGCCAACATT TGTGGTTCCA GACAATCGTG TTAAAGATCT TGTAGACAAG TGTGTGAAAG 1680
TTCTTGTAAA AGCATTTGAT GTTTTTACGC AGATTATCAC AATAGCTGGT ATTGAGGCCA 1740
AATGCTTTGT GCTTGGTGCT AAATACCTGT TGTTCAATAA TGCACTTGTC AAACTTGTCA 1800
GTGTTAAAAT CCTTGGCAAG AAGCAAAAGG GTCTTGAATG TGCATTCTTT GCTACTAGCT 1860
TGGTTGGTGC AACTGTTAAT GTGACACCTA AAAGAACAGA GACTGCCACT ATCAGCTTGA 1920
ACAAGGTTGA TGATGTTGTA GCACCAGGAG AGGGTTATAT CGTCATTGTT GGTGATATGG 1980
CTTTCTACAA GAGTGGTGAA TATTATTTCA TGATGTCTAG TCCTAATTTT GTTCTTACTA 2040
ACAATGTTTT TAAAGCAGTT AAAGTTCCAT CTTATGACAT CGTTTATGAT GTTGATAATG 2100
ATACCAAAAG CAAAATGATT GCAAAACTTG GTTCATCATT TGAATATGAT GGTGATATTG 2160
ATGCTGCTAT TGTAAAAGTC AATGAACTAC TCATTGAATT TAGGCAGCAA AGCTTGTGCT 2220
TCAGAGCTTT TAAGGACGAC AAAAGCATTT TTGTTGAAGC CTATTTTAAA AAGTATAAAA 2280
```

FIGURE 14-2

```
TGCCAGCATG CCTTGCAAAA CATATTGGTT TGTGGAACAT CATAAAGAAA GATTCATGTA 2340
AGAGGGGTTT TCTTAATCTC TTCAATCACT TGAATGAATT GGAAGATATC AAAGAAACTA 2400
ATATTCAGGC TATTAAAAAC ATTCTTTGCC CTGATCCTCT TCTTGATCTG GATTATGGTG 2460
CCATTTGGTA CAATTGCATG CCAGGTTGCT CTGATCCTTC AGTTTTGGGG AGTGTTCAAC 2520
TTTTGATCGG TAATGGTGTG AAAGTAGTTT GTGATGGCTG CAAAGGTTTT GCTAACCAAC 2580
TTTCAAAAGG TTACAACAAG CTCTGTAATG CGGCTCGCAA TGATATTGAG ATCGGTGGTA 2640
TACCATTTTC CACTTTTAAA ACACCTACAA ATACTTTTAT TGAAATGACA GATGCTATCT 2700
ATTCAGTTAT TGAACAAGGT AAGGCATTAT CCTTTAGAGA TGCTGATGTG CCAGTTGTAG 2760
ACAATGGTAC CATTTCTACT GCTGATTGGT CTGAACCCAT TCTGCTTGAA CCTGCTGAAT 2820
ATGTAAAACC AAAGAACAAT GGTAATGTCA TTGTTATTGC AGGTTATACA TTTTATAAAG 2880
ATGAGGATGA ACATTTTTAT CCTTATGGTT TTGGTAAAAT TGTGCAGAGA ATGTATAATA 2940
AAATGGGTGG TGGTGACAAA ACTGTCTCAT TTTCAGAAGA AGTAGATGTT CAAGAAATTG 3000
CACCTGTTAC ACGTGTTAAA CTTGAATTCG AATTTGACAA TGAAATTGTA ACTGGTGTTC 3060
TTGAACGGGC TATTGGTACT AGATACAAAT TTACTGGTAC AACTTGGGAA GAATTTGAAG 3120
AGTCTATTTC TGAAGAACTC GATGCAATCT TTGATACTCT AGCAAACCAA GGTGTCGAAC 3180
TTGAAGGTTA CTTCATTTAT GACACTTGTG GTGGCTTTGA TATAAAAAAT CCAGATGGTA 3240
TTATGATCTC TCAGTATGAT ATCAATATTA CTGCTGATGA AAAATCAGAA GTTAGTGCAT 3300
CAAGTGAAGA AGAAGAAGTT GAATCTGTTG AAGAAGATCC TGAGAATGAA ATTGTAGAAG 3360
CATCTGAAGG TGCTGAAGGG ACTTCTTCTC AAGAAGAGGT TGAAACAGTA GAAGTTGCAG 3420
ATATTACTTC TACAGAAGAA GATGTTGACA TTGTTGAAGT ATCTGCTAAA GATGACCCTT 3480
GGGCTGCAGC TGTTGATGTA CAAGAAGCTG AACAATTTAA TCCTTCTCTA CCACCTTTCA 3540
AGACAACGAA TCTCAACGGA AAAATTATCC TTAAGCAAGG GGATAATAAT TGTTGGATAA 3600
ATGCTTGTTG CTATCAGCTT CAGGCCTTTG ATTTTTTCAA CAATGAAGCT TGGGAGAAAT 3660
TTAAGAAAGG TGATGTCATG GACTTTGTAA ACCTTTGTTA TGCAGCAACA ACACTAGCAA 3720
GAGGTCATTC TGGTGATGCA GAGTATCTTC TTGAACTTAT GCTCAATGAT TATAGCACAG 3780
CCAAGATAGT ACTTGCAGCT AAGTGTGGTT GTGGTGAAAA AGAAATTGTT TTGGAAAGAG 3840
CTGTTTTTAA ACTCACCCCA CTTAAGGAGA GTTTTAATTA TGGTGTTTGT GGTGACTGCA 3900
TGCAAGTTAA CACCTGTAGA TTTTTAAGTG TTGAAGGCTC TGGTGTTTTT GTTCATGACA 3960
TATTAAGCAA GCAAACGCCA GAAGCTATGT TTGTTGTCAA ACCTGTTATG CATGCAGTTT 4020
ACACTGGCAC AACTCAAAAT GGCCATTACA TGGTTGATGA TATTGAACAC GGTTATTGTG 4080
TAGATGGTAT GGGTATTAAA CCACTTAAGA AACGGTGTTA TACATCCACA TTGTTCATTA 4140
ATGCCAATGT AATGACTAGA GCTGAAAAAC AAAACAAGA GTTAAAGTT GAAAAAGTAG 4200
AACAGCAACC GATAGTGGAG GAAAACAAAT CCTCTATTGA AAAAGAGGAA ATTCAAAGTC 4260
CTAAAAACGA TGACCTTATA CTTCCATTTT ACAAAGCTGG TAAACTTTCC TTTTATCAGG 4320
GTGCTTTGGA TGTTTTGATC AATTTCTTGG AACCTGATGT TATTGTTAAT GCTGCTAATG 4380
GTGATCTTAA ACACATGGGT GGTGTCGCAA GAGCCATCGA TGTTTTCACT GGTGGCAAAT 4440
TAACAGAACG TTCTAAGGAT TATCTTAAAA AGAACAAATC TATTGCTCCT GGTAATGCTG 4500
TTTTCTTTGA AAATGTCATT GAGCATCTTA GTGTTTTGAA TGCAGTTGGA CCACGTAATG 4560
GTGACAGCCG AGTTGAAGCC AAACTTTGTA ATGTTTACAA AGCAATTGCA AAGTGTGAAG 4620
GAAAAATATT AACACCACTT ATTAGTGTTG GTATCTTTAA TGTTAGACTT GAAACATCAT 4680
TGCAGTGCTT ACTTAAGACT GTGAATGACA GGGGATTGAA TGTCTTCGTA TACACTGACC 4740
AGGAGAGGCA AACTATTGAG AATTTCTTCT CTTGTTCTAT CCCTGTCAAT GTTACTGAGG 4800
ATAATGTTAA CCATGAACGT GTGTCTGTTT CTTTTGACAA AACATACGGT GAACAGCTTA 4860
```

FIGURE 14-3

```
AGGGCACCGT TGTCATCAAA GACAAAGATG TTACAAACCA GTTGCCTAGC GCTTTTGATG 4920
TTGGTCAAAA AGTTATTAAG GCTATTGATA TAGATTGGCA AGCTCATTAT GGTTTCCGTG 4980
ATGCTGCTGC TTTTAGCGCT AGTAGTCATG ATGCTTATAA ATTTGAAGTT GTTACACATA 5040
GCAATTTCAT TGTGCATAAG CAGACTGACA ACAACTGTTG GATTAATGCA ATTTGTCTTG 5100
CATTACAGAG ACTCAAGCCA CAGTGGAAAT TTCCTGGTGT TAGAGGTCTC TGGAATGAAT 5160
TTCTTGAGCG TAAAACACAA GGTTTTGTAC ATATGTTGTA TCACATTTCT GGAGTAAAGA 5220
AAGGTGAGCC AGGTGATGCT GAATTAATGC TGCATAAACT TGGTGACTTG ATGGACAATG 5280
ATTGTGAAAT CATTGTCACA CACACTACAG CATGTGACAA GTGCGAAAA GTAGAAAAGT 5340
TTGTTGGACC AGTGGTAGCA GCACCTCTTG CAATTCATGG CACTGACGAA ACATGTGTGC 5400
ATGGCGTTAG TGTCAATGTC AAAGTCACCC AAATTAAGGG CACTGTTGCT ATTACTTCTT 5460
TGATTGGTCC TATTATTGGA GAAGTACTAG AAGCAACTGG TTATATTTGT TATAGCGGTT 5520
CTAACAGGAA TGGTCATTAC ACCTATTACG ATAACCGTAA TGGATTAGTG GTTGATGCAG 5580
AAAAGGCTTA CCATTTTAAT AGAGACTTAT TACAGGTCAC AACAGCTATT GCAAGTAATT 5640
TCGTTGTCAA GAAACCACAA GCAGAGGAAA GACCTAAGAA TTGTGCTTTT AACAAAGTTG 5700
CAGCATCTCC TAAGATTGTA CAAGAACAAA AATTGTTGGC TATTGAAAGT GGTGCTAACT 5760
ATGCTCTTAC TGAATTTGGA AGATATGCTG ACATGTTCTT TATGGCTGGA GATAAAATTC 5820
TTAGGTTGCT GCTTGAAGTC TTTAAATATT TGCTGGTTTT ATTTATGTGT CTTAGAAGTA 5880
CTAAGATGCC TAAAGTTAAA GTCAAACCAC CTCTTGCATT TAAAGATTTT GGTGCTAAGG 5940
TCAGAACGCT CAATTACATG AGACAATTGA ACAAACCCTC TGTCTGGCGT TACGCAAAAC 6000
TAGTTTTATT GTTGATAGCA ATATATAATT TCTTTTATTT GTTTGTCAGT ATACCAGTAG 6060
TGCATAAATT AACATGTAAC GGTGCTGTAC AGGCATATAA AAATTCTAGT TTTATAAAGT 6120
CTGCAGTCTG TGGCAACTCT ATTTTATGCA AAGCCTGTTT GGCTTCTTAT GATGAGTTGG 6180
CTGATTTTCA ACATCTCCAA GTTACTTGGG ATTTCAAATC TGACCCACTA TGGAACAGAC 6240
TGGTACAATT GTCTTACTTT GCATTCTTGG CTGTTTTTGG TAATAACTAT GTTAGGTGTT 6300
TTCTTATGTA TTTTGTATCT CAGTACCTCA ACCTTTGGCT TTCTTATTTT GGTTATGTAG 6360
AGTACAGTTG GTTTTTGCAT GTTGTCAACT TTGAATCCAT CTCAGCTGAG TTTGTGATCG 6420
TAGTTATAGT GGTTAAGGCA GTTCTCGCCC TTAAACATAT TGTTTTCGCA TGCTCAAACC 6480
CGTCTTGCAA AACGTGCTCT AGGACTGCAA GGCAGACACG TATTCCTATT CAAGTTGTTG 6540
TTAATGGTTC AATGAAGACT GTTTATGTTC ATGCTAATGG TACTGGTAAA TTCTGCAAGA 6600
AACACAATTT TTATTGTAAG AACTGTGATT CTTATGGCTT TGAAAACACA TTCATCTGTG 6660
ACGAAATTGT ACGTGATCTC AGTAATAGTG TTAAACAAAC TGTTTACGCC ACTGATAGAT 6720
CTCATCAAGA AGTCACAAAA GTTGAATGTT CAGATGGCTT TTACAGATTT TATGTTGGTG 6780
ATGAATTCAC TTCATATGAC TATGATGTAA AACACAAGAA ATACAGTAGT CAAGAGGTTC 6840
TCAAGAGCAT GCTCTTGCTT GATGACTTCA TTGTGTACAG TCCATCTGGT TCTGCTCTTG 6900
CAAATGTTAG AAATGCCTGT GTTTACTTTT CACAACTTAT TGGTAAGCCT ATTAAGATTG 6960
TTAACAGTGA TTTGCTTGAA GACCTCTCTG TAGATTTTAA AGGGGCACTT TTTAATGCTA 7020
AAAAGAATGT AATTAAGAAT TCTTTCAATG TTGATGTCTC AGAATGCAAA AATCTTGACG 7080
AATGTTACAG GGCTTGCAAT CTTAATGTTT CATTTTCTAC ATTTGAAATG GCTGTCAACA 7140
ATGCTCATAG GTTTGGTATT CTGATTACTG ATCGTTCTTT TAACAATTTC TGGCCATCAA 7200
AAGTTAAGCC TGGTTCATCT GGTGTGTCGG CCATGGACAT TGGTAAGTGT ATGACTTCTG 7260
ATGCTAAGAT TGTTAATGCT AAAGTTTTAA CTAACGTGG TAAAAGTGTT GTTGGCTTA 7320
GCCAGGATTT TGCTGCACTT AGCTCAACTG CTCAGAAAGT TTTGGTTAAA ACTTTTGTAG 7380
AAGAAGGTGT CAACTTTTCA CTCACATTTA ATGCTGTAGG TTCAGATGAT GATCTTCCTT 7440
```

FIGURE 14-4

```
ATGAAAGATT CACTGAATCT GTGTCTCCAA AAAGTGGTTC AGGCTTTTTC GATGTAATTA 7500
CACAGCTTAA ACAAATTGTG ATTTTGGTTT TTGTTTTTAT CTTTATTTGT GGTTTGTGCT 7560
CTGTTTACAG TGTTGCTACA CAGTCCTACA TTGAATCTGC TGAAGGCTAT GACTACATGG 7620
TTATTAAGAA TGGAATTGTT CAACCTTTTG ACGATACCAT TTCATGTGTT CATAACACTT 7680
ATAAAGGATT CGGTGACTGG TTTAAAGCTA AGTATGGTTT TATCCCTACT TTTGGTAAAT 7740
CATGTCCAAT TGTTGTAGGA ACTGTTTTTG ATCTTGAAAA TATGAGACCA ATTCCTGACG 7800
TGCCTGCATA TGTTTCTATT GTGGGTAGAT CTCTTGTTTT CGCTATTAAT GCTGCTTTTG 7860
GTGTTACTAA TATGTGCTAT GATCATACTG GCAATGCAGT TAGTAAGGAC TCTTACTTTG 7920
ATACTTGTGT GTTTAATACT GCGTGCACCA CTCTTACAGG TCTTGGTGGT ACAATTGTAT 7980
ATTGTGCAAA GCAAGGTTTA GTTGAAGGTG CTAAGCTCTA TAGTGATCTT ATGCCAGACT 8040
ATTATTATGA GCATGCTAGT GGTAACATGG TTAAATTGCC AGCAATTATT AGAGGACTTG 8100
GTCTACGTTT TGTGAAAACA CAGGCTACAA CTTATTGTAG AGTGGGAGAG TGCATTGATA 8160
GTAAAGCTGG TTTTTGCTTT GGTGGCGATA ACTGGTTTGT CTACGACAAT GAGTTTGGCA 8220
ATGGATACAT CTGTGGTAAT TCTGTGCTAG GATTCTTTAA GAATGTCTTC AAACTCTTTA 8280
ACTCTAACAT GTCTGTGGTA GCTACATCTG GTGCGATGCT TGTTAACATT ATTATTGCAT 8340
GCTTAGCTAT TGCAATGTGT TATGGTGTTC TTAAGTTTAA GAAGATTTTT GGTGATTGTA 8400
CTTTCCTCAT TGTTATGATC ATTGTCACCC TTGTTGTGAA CAATGTGTCT TATTTTGTCA 8460
CTCAAAACAC GTTCTTTATG ATCATCTACG CCATTGTTTA CTATTTTATA ACAAGAAAAC 8520
TTGCATACCC AGGCATTCTT GATGCTGGGT TTATTATTGC TTATATTAAT ATGGCTCCAT 8580
GGTACGTGAT TACCGCATAT ATCCTAGTTT TCCTCTATGA CTCACTCCCT TCACTGTTTA 8640
AACTTAAAGT TTCAACAAAT CTTTTTGAAG GTGATAAATT TGTGGGTAAC TTTGAATCTG 8700
CTGCTATGGG TACTTTTGTT ATTGACATGC GTTCATATGA AACTATTGTT AATTCTACTT 8760
CTATTGCTAG AATTAAATCA TATGCTAACA GCTTCAATAA ATATAAGTAC TACACAGGTT 8820
CAATGGGAGA AGCTGACTAC AGAATGGCTT GCTATGCTCA TCTTGGTAAA GCTCTTATGG 8880
ACTATTCTGT TAATAGAACA GACATGCTTT ACACACCTCC TACTGTTAGT GTTAATTCTA 8940
CACTTCAGTC AGGTTTGCGG AAAATGGCAC AGCCTAGTGG TCTTGTAGAG CCTTGCATTG 9000
TAAGAGTTTC CTATGGTAAC AATGTGCTTA ATGGTTTATG GTTAGGAGAT GAAGTCATTT 9060
GCCCTAGACA TGTTATTGCT AGTGATACCA CACGTGTTAT CAACTATGAA AATGAAATGT 9120
CTAGTGTGAG ACTTCACAAC TTTTCAGTTT CTAAGAATAA TGTGTTTTTG GGTGTTGTGT 9180
CTGCCAGATA TAAGGGTGTG AATCTTGTAC TTAAAGTCAA CCAGGTTAAT CCTAACACAC 9240
CAGAACATAA ATTTAAGTCT ATTAAAGCTG GTGAAAGTTT TAACATTCTT GCTTGTTATG 9300
AAGGATGTCC TGGCAGTGTT TATGGTGTCA ACATGAGAAG TCAAGGTACC ATTAAGGAT 9360
CTTTTATAGC TGGTACTTGT GGATCAGTAG GTTATGTGTT AGAAAATGGA ATTCTCTATT 9420
TTGTATACAT GCATCACTTA GAACTTGGAA ATGGCTCGCA TGTTGGTTCC AATTTTGAAG 9480
GAGAAATGTA CGGTGGTTAT GAAGATCAAC CTAGCATGCA ATTGGAAGGT ACTAATGTCA 9540
TGTCATCAGA TAATGTGGTT GCATTCCTAT ATGCTGCACT TATCAATGGT GAAAGGTGGT 9600
TTGTTACAAA CACATCGATG TCATTAGAAT CATACAATAC ATGGGCCAAA ACTAACAGTT 9660
TCACAGAACT TTCTTCAACT GATGCTTTTA GCATGTTGGC TGCAAAAACT GGTCAAAGTG 9720
TTGAGAAATT ACTAGATAGC ATCGTAAGAC TCAACAAGGG TTTTGGAGGT CGTACTATAC 9780
TTTCTTATGG CTCATTGTGT GACGAGTTCA CTCCAACTGA AGTCATAAGG CAAATGTATG 9840
GTGTAAATCT TCAGGCTGGT AAAGTAAAAT CTTTCTTCTA CCCTATTATG ACTGCAATGA 9900
CAATTCTCTT TGCCTTTTGG CTTGAATTCT TTATGTACAC ACCCTTCACT TGGATTAATC 9960
CAACTTTTGT TAGCATTGTA TTGGCTGTTA CAACTTTGAT CTCGACGGTT TTTGTCTCTG 10020
```

FIGURE 14-5

```
GCATCAAACA TAAGATGTTG TTCTTTATGT CTTTTGTCCT TCCTAGTGTT ATCCTTGTGA 10080
CAGCACACAA TTTGTTCTGG GACTTTTCTT ACTATGAAAG TCTTCAGTCA ATTGTTGAGA 10140
ATACTAACAC TATGTTTTTG CCTGTTGACA TGCAAGGTGT CATGCTCACA GTGTTTGCT  10200
TTATTGTCTT TGTTACATAT AGTGTTAGAT TCTTCACTTG CAAACAATCA TGGTTCTCAC 10260
TTGCTGTGAC AACTATTCTT GTGATCTTTA ACATGGTTAA AATCTTTGGA ACATCTGATG 10320
AACCATGGAC TGAAAACCAA ATTGCTTTCT GCTTTGTGAA CATGCTTACT ATGATTGTCA 10380
GTCTTACTAC AAAGGATTGG ATGGTTGTCA TTGCATCATA CAGAATTGCA TATTATATTG 10440
TTGTATGTGT AATGCCATCT GCTTTTGTAT CTGACTTTGG GTTTATGAAG TGTATTAGCA 10500
TTGTTTACAT GGCGTGCGGT TATTTGTTTT GTTGCTATTA TGGCATTCTT TATTGGGTTA 10560
ACAGATTTAC ATGCATGACT TGTGGTGTTT ATCAATTCAC TGTGTCTGCA GCTGAACTTA 10620
AATACATGAC CGCTAACAAC CTTTCTGCAC CTAAGAACGC ATATGACGCT ATGATTCTTA 10680
GTGCTAAATT GATTGGTGTT GGAGGTAAGA GAAACATCAA AATTTCAACT GTACAGTCAA 10740
AACTTACAGA GATGAAATGT ACCAATGTTG TCTTGCTTGG TCTTTTATCT AAAATGCATG 10800
TCGAGTCTAA CTCAAAGAG TGGAACTATT GTGTTGGACT ACACAATGAG ATAAACCTTT 10860
GTGACGATCC TGAAATCGTT CTTGAGAAAC TGTTAGCTCT TATTGCATTC TTCTTGTCCA 10920
AACATAACAC TTGTGACCTT AGCGAACTTA TTGAATCATA CTTTGAGAAC ACCACCATAC 10980
TCCAGAGTGT GGCTTCAGCT TATGCTGCAT TGCCTAGCTG GATTGCACTT GAAAAAGCTC 11040
GCGCTGATCT TGAAGAGGCT AAGAAAAATG ATGTTAGCCC TCAAATTTTG AAGCAGCTTA 11100
CTAAAGCATT TAACATTGCC AAGAGTGATT TTGAGCGCGA AGCATCAGTG CAAAAGAAAC 11160
TCGACAAAAT GGCTGAGCAG GCTGCAGCTA GTATGTATAA AGAAGCACGA GCTGTGGACA 11220
GAAAGTCAAA GATTGTTTCT GCTATGCATA GCCTACTTTT TGGTATGCTT AAGAAACTTG 11280
ATATGTCCAG TGTCAACACT ATTATTGACC AGGCTCGTAA TGGTGTTCTA CCTTTAAGTA 11340
TCATTCCAGC TGCATCAGCT ACAAGACTTG TTGTTATTAC ACCTAGCCTT GAAGTGTTTT 11400
CCAAGATTAG GCAAGAAAAC AATGTTCATT ATGCTGGTGC TATTTGGACT ATTGTTGAAG 11460
TTAAAGATGC TAATGGTTCA CATGTACATC TTAAGGAAGT CACCGCTGCT AATGAATTAA 11520
ACCTTACTTG GCCATTGAGC ATTACTTGTG AGAGAACCAC AAAGCTTCAG AACAATGAAA 11580
TTATGCCAGG TAAACTTAAA GAAAGAGCTG TCAGAGCGTC AGCAACTCTT GATGGTGAAG 11640
CTTTCGGCAG TGGAAAGGCT CTTATGGCAT CTGAAAGTGG AAAAAGCTTT ATGTATGCAT 11700
TTATAGCCTC AGACAACAAT CTTAAGTATG TTAAGTGGGA GAGCAATAAT GATATTATAC 11760
CTATTGAACT TGAAGCTCCA TTGCGTTTCT ATGTTGACGG CGCTAATGGT CCTGAAGTCA 11820
AGTATTTGTA TTTTGTCAAG AATTTAAACA CTCTTAGACG TGGTGCCGTT CTTGGTTATA 11880
TCGGTGCAAC AGTTCGTCTG CAAGCTGGTA AACCCACTGA ACATCCATCT AACAGTAGTT 11940
TATTGACATT GTGTGCTTTT TCACCTGATC CTGCTAAAGC ATATGTTGAT GCTGTTAAGA 12000
GAGGCATGCA ACCAGTTAAT AACTGTGTAA AAATGCTCTC AAATGGTGCT GGTAATGGTA 12060
TGGCTGTTAC AAACGGTGTC GAAGCTAACA CACAACAGGA CTCTTATGGT GGTGCTTCAG 12120
TTTGTATTTA TTGCAGATGC CATGTTGAAC ATCCTGCTAT TGATGGATTA TGCCGCTACA 12180
AAGGTAAGTT CGTGCAAATA CCAACTGGCA CACAAGATCC AATTCGGTTC TGTATTGAAA 12240
ATGAAGTTTG TGTTGTCTGT GGTTGTTGGC TTAACAATGG TTGCATGTGC GATCGTACTT 12300
CTATGCAGAG TTTTACTGTT GATCAAAGTT ATTTAAACGA GTGCGGGTT CTAGTGCAGC  12360
TCGACTAGAA CCCTGCAATG GTACTGATCC AGACCATGTT AGTAGAGCTT TTGACATCTA 12420
CAACAAAGAT GTTGCGTGTA TTGGTAAATT CCTTAAGACG AATTGTTCAA GATTTAGGAA 12480
TTTGGACAAA CATGATGCCT ACTACATTGT CAAACGTTGT ACAAGACCG TTATGGACCA  12540
TGAGCAAGTC TGTTATAACG ATCTTAAAGA TTCTGGTGCT GTTGCTGAGC ATGACTTCTT 12600
```

FIGURE 14-6

```
CACATATAAA GAGGGTAGAT GTGAGTTCGG TAATGTTGCA CGTAGGAATC TTACAAAGTA 12660
CACAATGATG GATCTTTGTT ACGCTATCAG AAATTTTGAT GAAAAGAACT GTGAAGTTCT 12720
CAAAGAAATA CTCGTGACAG TAGGTGCTTG CACTGAAGAA TTCTTTGAAA ATAAAGATTG 12780
GTTTGATCCA GTTGAAAATG AAGCCATACA TGAAGTTTAT GCAAAACTTG GACCCATTGT 12840
AGCCAATGCT ATGCTTAAAT GTGTTGCTTT TTGCGATGCG ATAGTGGAAA AAGGCTATAT 12900
AGGTGTTATA ACACTTGACA ACCAAGATCT TAATGGCAAT TTCTACGATT TCGGCGATTT 12960
CGTGAAGACT GCTCCGGGTT TTGGTTGCGC TTGTGTTACA TCATATTATT CTTATATGAT 13020
GCCTTTAATG GGGATGACTT CATGCTTAGA GTCTGAAAAC TTTGTGAAAA GTGACATCTA 13080
TGGTTCTGAT TATAAGCAGT ATGATTTACT AGCTTATGAT TTTACCGAAC ATAAGGAGTA 13140
CCTTTTCCAA AAATACTTTA AGTACTGGGA TCGCACATAT CACCCAAATT GTTCTGATTG 13200
TACTAGTGAC GAGTGTATTA TTCATTGTGC TAATTTTAAC ACATTGTTTT CTATGACAAT 13260
ACCAATGACA GCTTTTGGAC CACTTGTCCG TAAAGTTCAT ATTGATGGTG TACCAGTAGT 13320
TGTTACTGCA GGTTACCATT TCAAACAACT TGGTATAGTA TGGAATCTTG ATGTAAAATT 13380
AGACACAATG AAGTTGAGCA TGACTGATCT TCTTAGATTT GTCACAGATC CAACACTTCT 13440
TGTAGCATCA AGCCCTGCAC TTTTAGACCA GCGTACTGTC TGTTTCTCCA TTGCAGCTTT 13500
GAGTACTGGT ATTACATATC AGACAGTAAA ACCAGGTCAC TTTAACAAAG ATTTCTACGA 13560
TTTCATAACA GAGCGTGGAT TCTTTGAAGA GGGATCTGAG TTAACATTAA AACATTTTTT 13620
CTTTGCACAG GGTGGTGAAG CTGCTATGAC AGACTTCAAT TATTATCGCT ACAATAGAGT 13680
CACAGTACTT GATATTTGCC AAGCTCAATT TGTTTACAAA ATAGTTGGCA AGTATTTTGA 13740
ATGTTATGAC GGTGGGTGCA TTAATGCTCG TGAAGTTGTT GTTACAAACT ATGACAAGAG 13800
TGCTGGCTAT CCTTTGAACA AATTTGGTAA AGCTAGACTT TACTACGAAA CTCTTTCATA 13860
TGAAGAGCAG GATGCACTTT TTGCTTTAAC AAAGAGAAAT GTTTTACCCA CAATGACTCA 13920
AATGAATTTG AAATACGCTA TTTCTGGTAA GGCAAGAGCT CGTACAGTAG GAGGAGTTTC 13980
ACTTCTTTCT ACCATGACTA CGAGACAATA TCATCAGAAG CATTTGAAGT CAATTGCTGC 14040
AACACGCAAT GCTACTGTGG TCATTGGTTC AACCAAGTTT TATGGTGGTT GGGACAATAT 14100
GCTTAAAAAT TTAATGCGTG ATGTTGATAA TGGTTGTTTG ATGGGATGGG ACTATCCTAA 14160
GTGTGACCGT GCTTTACCTA ATATGATTAG AATGGCTTCT GCCATGATAT TAGGTTCTAA 14220
GCATGTTGGT TGTTGTACAC ATAATGATAG GTTCTACCGC CTCTCCAATG AGTTAGCTCA 14280
AGTACTCACA GAAGTTGTGC ATTGCACAGG TGGTTTTTAT TTTAAACCTG GTGGTACAAC 14340
TAGCGGTGAT GGTACTACAG CATATGCTAA CTCTGCTTTT AACATCTTTC AAGCTGTTTC 14400
TGCTAATGTT AATAAGCTTT TGGGGGTTGA TTCAAACGCT TGTAACAACG TTACAGTAAA 14460
ATCCATACAA CGTAAAATTT ACGATAATTG TTATCGTAGT AGCAGCATTG ATGAAGAATT 14520
TGTTGTTGAG TACTTTAGTT ATTTGAGAAA ACACTTTTCT ATGATGATTT TATCTGATGA 14580
TGGAGTTGTG TGCTACAACA AAGATTATGC GGATTAGGT TATGTAGCTG ACATTAATGC 14640
TTTTAAAGCA ACACTTTATT ACCAGAATAA CGTCTTTATG TCCACTTCTA AGTGTTGGGT 14700
AGAACCAGAT CTTAGTGTTG GACCACATGA ATTTTGTTCA CAGCATACAT TGCAGATTGT 14760
TGGGCCTGAT GGAGACTACT ATCTTCCCTA TCCAGACCCG TCCAGAATTT TATCAGCTGG 14820
TGTGTTTGTT GATGACATAG TTAAAACAGA CAATGTTATT ATGTTAGAAC GTTACGTGTC 14880
ATTGGCTATT GACGCATACC CGCTCACAAA ACACCCTAAG CCTGCTTATC AAAAAGTGTT 14940
TTACACTCTA CTAGATTGGG TTAAACATCT ACAGAAAAAT TTGAATGCAG GTGTTCTTGA 15000
TTCGTTTTCA GTGACAATGT TAGAGGAAGG TCAAGATAAG TTCTGGAGTG AAGAGTTTTA 15060
CGCTAGCCTC TATGAAAAGT CCACTGTCTT GCAAGCTGCA GGCATGTGTG TAGTATGTGG 15120
TTCGCAAACT GTACTTCGTT GTGGAGACTG TCTTAGGAGA CCACTTTTAT GCACGAAATG 15180
```

FIGURE 14-7

```
TGCTTACGAC CATGTTATGG GAACAAAGCA TAAATTCATT ATGTCTATCA CACCATATGT 15240
GTGTAGTTTT AATGGTTGTA ATGTCAATGA TGTTACAAAG TTGTTTTTAG GTGGTCTTAG 15300
TTATTATTGT ATGAACCACA AACCACAGTT GTCATTCCCA CTCTGTGCTA ATGGCAACGT 15360
TTTTGGTCTA TATAAAAGTA GTGCAGTCGG CTCAGAGGCT GTTGAAGATT TCAACAAACT 15420
TGCAGTTTCT GACTGGACTA ATGTAGAAGA CTACAAACTT GCTAACAATG TCAAGGAATC 15480
TCTGAAAATT TTCGCTGCTG AAACTGTGAA AGCTAAGGAG GAGTCTGTTA AATCTGAATA 15540
TGCTTATGCT GTATTAAAGG AGGTTATCGG CCCTAAGGAA ATTGTACTCC AATGGAAGC 15600
TTCTAAGACT AAGCCTCCAC TTAACAGAAA TTCAGTTTTC ACGTGTTTTC AGATAAGTAA 15660
GGATACTAAA ATTCAATTAG GTGAATTTGT GTTTGAGCAA TCTGAGTACG GTAGTGATTC 15720
TGTTTATTAC AAGAGCACGA GTACTTACAA ATTGACACCA GGTATGATTT TTGTGTTGAC 15780
TTCTCATAAT GTGAGTCCTC TTAAAGCTCC AATTTTAGTC AACCAAGAAA AGTACAATAC 15840
CATATCTAAG CTCTATCCTG TCTTTAATAT AGCGGAGGCC TATAATACAC TGGTTCCTTA 15900
CTACCAAATG ATAGGTAAGC AAAAATTTAC AACTATCCAA GGTCCTCCTG GTAGCGGTAA 15960
ATCTCATTGT GTTATAGGTT TGGGTTTGTA TTACCCTCAG GCGAGAATAG TCTACACTGC 16020
ATGTTCTCAT GCGGCTGTAG ACGCTTTATG TGAAAAAGCA GCCAAAAACT TCAATGTTGA 16080
TAGATGTTCA AGGATAAATAC CTCAAAGAAT CAGAGTTGAT TGTTACACAG GCTTTAAGCC 16140
TAATAACACC AATGCGCAGT ACTTGTTTTG TACTGTTAAT GCTCTACCAG AAGCAAGTTG 16200
TGACATTGTT GTAGTTGATG AGGTCTCTAT GTGTACTAAT TATGATCTTA GTGTCATAAA 16260
TAGCCGACTG AGTTACAAAC ATATTGTTTA TGTTGGAGAC CCACAGCAGC TACCAGCTCC 16320
TAGAACTTTG ATTAATAAGG GTGTACTTCA ACCGCAGGAT TACAATGTTG TAACCAAAAG 16380
AATGTGCACA CTAGGACCTG ATGTCTTTTT GCATAAATGT TACAGGTGCC CAGCTGAAAT 16440
TGTTAAGACA GTCTCTGCAC TTGTTTATGA AAATAAATTT GTACCTGTCA ACCCAGAATC 16500
AAAGCAGTGC TTCAAAATGT TTGTAAAAGG TCAGGTTCAG ATTGAGTCTA ACTCTTCTAT 16560
AAACAACAAG CAACTAGAGG TTGTCAAGGC CTTTTTAGCA CATAATCCAA AATGGCGTAA 16620
AGCTGTTTTC ATCTCACCCT ATAATAGTCA AAATTATGTT GCTCGGCGTC TTCTTGGTTT 16680
GCAAACGCAA ACTGTGGATT CCGCTCAGGG TAGTGAGTAT GATTACGTCA TCTACACACA 16740
GACCTCCGAT ACACAGCATG CTACTAATGT TAACAGATTT AATGTTGCCA TTACGAGAGC 16800
AAAGGTTGGT ATACTTTGTA TCATGTGTGA TAGAACTATG TATGAGAATC TTGATTTCTA 16860
TGAACTCAAA GATTCAAAGA TTGGTTTACA AGCAAAACCT GAAACTTGTG GTTTATTTAA 16920
AGATTGTTCG AAGAGCGAAC AATACATACC ACCTGCTTAT GCAACGACAT ATATGAGCTT 16980
ATCTGATAAT TTTAAGACAA GTGATGGTTT AGCTGTTAAC ATCGGTACAA AAGATGTTAA 17040
ATATGCTAAT GTCATCTCAT ATATGGGATT CAGGTTTGAA GCCAACATAC CAGGCTATCA 17100
CACACTATTC TGCACGCGAG ATTTTGCTAT GCGTAATGTT AGAGCATGGC TTGGGTTTGA 17160
CGTTGAAGGT GCACATGTCT GTGGTGATAA TGTTGAACT AATGTACCAT TACAGCTGGG 17220
TTTCTCAAAC GGTGTGGATT TTGTAGTGCA AACTGAAGGA TGTGTTATTA CTGAAAAAGG 17280
TAATAGCATT GAGGTTGTAA AAGCACGAGC ACCACCAGGT GAGCAATTTG CACACTTGAT 17340
TCCGCTTATG AGAAAGGGTC AACCTTGGCA CATTGTTAGA CGCCGTATAG TGCAGATGGT 17400
CTGTGACTAT TTTGATGGCT TATCAGACAT TCTGATCTTT GTGCTTTGGG CTGGTGGTCT 17460
TGAACTTACA ACTATGAGAT ACTTTGTTAA AATTGGAAGA CCACAAAAAT GTGAATGCGG 17520
CAAAAGTGCA ACTTGTTATA GTAGCTCTCA ATCTGTTTAT GCTTGCTTCA AGCATGCATT 17580
AGGATGTGAT TATTTATATA ACCCTTACTG CATTGACATA CAGCAATGGG GTTACACAGG 17640
ATCTTTGAGC ATGAATCATC ATGAAGTTTG CAACATTCAT AGAAATGAGC ATGTAGCTAG 17700
TGGTGATGCT ATCATGACTA GATGTCTCGC TATACATGAC TGTTTTGTCA AACGTGTTGA 17760
```

FIGURE 14-8

```
TTGGTCAATT GTGTACCCTT TTATTGACAA TGAAGAAAAG ATCAATAAAG CTGGTCGCAT 17820
AGTGCAGTCA CATGTCATGA AAGCTGCTCT GAAGATTTTT AATCCTGCTG CAATTCACGA 17880
TGTGGGTAAT CCAAAAGGCA TCCGTTGTGC TACAACACCA ATACCATGGT TTTGTTATGA 17940
TCGTGATCCT ATTAATAACA ATGTTAGATG TCTGGATTAT GACTATATGG TACATGGTCA 18000
AATGAATGGT CTTATGTTAT TTTGGAACTG TAATGTAGAC ATGTACCCAG AGTTTTCAAT 18060
TGTTTGTAGA TTTGATACTC GCACTCGCTC TAAATTGTCT TTAGAAGGTT GTAATGGTGG 18120
TGCATTGTAT GTTAATAACC ATGCTTTCCA CACACCAGCT TATGATAGAA GAGCTTTTGC 18180
TAAGCTTAAA CCTATGCCAT TCTTTTACTA TGATGATAGT AATTGTGAAC TTGTTGATGG 18240
GCAACCTAAT TATGTACCAC TTAAGTCAAA TGTTTGCATA ACAAAATGCA ACATTGGTGG 18300
TGCTGTCTGC AAGAAGCATG CTGCTCTTTA CAGAGCGTAT GTTGAGGATT ACAACATTTT 18360
TATGCAGGCT GGTTTTACAA TATGGTGTCC TCAAAACTTT GACACCTATA TGCTTTGGCA 18420
TGGTTTTGTT AATAGCAAAG CACTTCAGAG TCTAGAAAAT GTGGCTTTTA ATATCGTTAA 18480
GAAAGGTGCC TTCACCGGTT AAAAGGTGA CTTACCAACT GCTGTTATTG CTGACAAAAT 18540
AATGGTAAGA GATGGACCTA CTGACAAATG TATTTTTACA AATAAGACTA GTTTACCTAC 18600
AAATGTAGCT TTTGAGTTAT ATGCAAAACG CAAACTTGGA CTCACACCTC CATTAACAAT 18660
ACTTAGGAAT TTAGGTGTTG TCGCAACATA TAAGTTTGTG TTGTGGGATT ATGAAGCTGA 18720
ACGTCCTTTC TCAAATTTCA CTAAGCAAGT GTGTTCCTAC ACTGATCTTG ATAGTGAAGT 18780
TGTAACATGT TTTGATAATA GTATTGCTGG TTCTTTTGAG CGTTTTACTA CTACAAGAGA 18840
TGCAGTGCTT ATTTCTAATA ACGCTGTGAA AGGGCTTAGT GCCATTAAAT TACAATATGG 18900
CCTTTTGAAT GATCTACCTG TAAGTACTGT TGGAAATAAA CCTGTCACAT GGTATATCTA 18960
TGTGCGCAAG AATGGTGAGT ACGTCGAACA AATCGATAGT TACTATACAC AGGGACGTAC 19020
TTTTGAAACC TTCAAACCTC GTAGTACAAT GGAAGAAGAT TTTCTTAGTA TGGATACTAC 19080
ACTCTTCATC CAAAAGTATG GTCTTGAGGA TTATGGTTTT GAACACGTTG TATTTGGAGA 19140
TGTCTCTAAA ACTACCATTG GTGGTATGCA TCTTCTTATA TCGCAAGTGC GCCTTGCAAA 19200
AATGGGTTTG TTTTCCGTTC AAGAATTTAT GAATAATTCT GACAGTACAC TGAAAAGTTG 19260
TTGTATTACA TATGCTGATG ATCCATCTTC TAAGAATGTG TGCACTTATA TGGACATACT 19320
CTTGGACGAT TTTGTGACTA TCATTAAGAG CTTAGATCTT AATGTTGTGT CCAAAGTTGT 19380
GGATGTCATT GTAGATTGTA AGGCATGGAG ATGGATGTTG TGGTGTGAGA ATTCACATAT 19440
TAAAACCTTC TATCCACAAC TCCAATCTGC TGAATGGAAT CCCGGCTATA GCATGCCTAC 19500
ACTGTACAAA ATCCAGCGTA TGTGTCTCGA ACGGTGTAAT CTCTACAATT ATGGTGCACA 19560
AGTGAAATTA CCTGTAGGCA TTACTACTAA GTTCGTTAAG TATACTCAGT TGTGTCAATA 19620
CCTTAACACT ACTACATTGT GTGTACCACA CAAATGCGT GTATTGCATT TAGGAGCTGC 19680
TGGTGCATCT GGTGTTGCTC CTGGTAGTAC TGTATTAAGA AGATGGTTAC CAGATGATGC 19740
CATATTGGTT GATAATGATT TGAGAGATTA CGTTTCCGAC GCAGACTTCA GTGTTACAGG 19800
TGATTGTACT AGTCTTTACA TCGAAGACAA GTTTGATTTG CTCGTCTCTG ATTTATATGA 19860
TGGCTCCACA AAATCAATTG ACGGTGAAAA CACGTCGAAA GATGGTTTCT TTACTTATAT 19920
TAATGGTTTC ATTAAGAGA AACTGTCACT TGGTGGATCT GTTGCCATTA AAATCACGGA 19980
ATTTAGTTGG AATAAAGATT TATATGAATT GATTCAAAGA TTTGAGTATT GGACTGTGTT 20040
TTGTACAAGT GTTAACACGT CATCATCAGA AGGCTTTCTG ATTGGTATTA ACTACTTAGG 20100
ACCATACTGT GACAAAGCAA TAGTAGATGG AAATATAATG CATGCCAATT ATATATTTTG 20160
GAGAAACTCT ACAATTATGG CTCTATCACA TAACTCAGTC CTAGACACTC CTAAATTCAA 20220
GTGTCGTTGT AACAACGCAC TTATTGTTAA TTTAAAAGAA AAAGAATTGA ATGAAATGGT 20280
CATTGGATTA CTAAGGAAGG GTAAGTTGCT CATTAGAAAT AATGGTAAGT TACTAAACTT 20340
```

FIGURE 14-9

```
TGGTAACCAC TTCGTTAACA CACCATGAAA AAACTATTTG TGGTTTTGGT CGTAATGCCA 20400
TTGATTTATG GAGACAATTT TCCTTGTTCT AAATTGACTA ATAGAACTAT AGGCAACCAG 20460
TGGAATCTCA TTGAAACCTT CCTTCTAAAC TATAGTAGTA GGTTACCACC TAATTCAGAT 20520
GTGGTGTTAG GTGATTATTT TCCTACTGTA CAACCTTGGT TTAATTGCAT TCGCAATGAT 20580
AGTAATGACC TTTATGTTAC ACTGGAAAAT CTTAAAGCAT TGTATTGGGA TTATGCTACA 20640
GAAAATATCA CTTGGAATCA CAGACAACGG TTAAACGTAG TCGTTAATGG ATACCCATAC 20700
TCCATCACAG TTACAACAAC CCGCAATTTT AATTCTGCTG AAGGTGCTAT TATATGCATT 20760
TGTAAGGGCT CACCACCTAC TACCACCACA GAATCTAGTT TGACTTGCAA TTGGGGTAGT 20820
GAGTGCAGGT TAAACCATAA GTTCCCTATA TGTCCTTCTA ATTCAGAGGC AAATTGTGGT 20880
AATATGCTGT ATGGCCTACA ATGGTTTGCA GATGAGGTTG TTGCTTATTT ACATGGTGCT 20940
AGTTACCGTA TTAGTTTTGA AAATCAATGG TCTGGCACTG TCACATTTGG TGATATGCGT 21000
GCGACAACAT TAGAAGTCGC TGGCACGCTT GTAGACCTTT GGTGGTTTAA TCCTGTTTAT 21060
GATGTCAGTT ATTATAGGGT TAATAATAAA AATGGTACTA CCGTAGTTTC CAATTGCACT 21120
GATCAATGTG CTAGTTATGT GGCTAATGTT TTTACTACAC AGCCAGGAGG TTTTATACCA 21180
TCAGATTTTA GTTTTAATAA TTGGTTCCTT CTAACTAATA GCTCCACGTT GGTTAGTGGT 21240
AAATTAGTTA CCAAACAGCC GTTATTAGTT AATTGCTTAT GGCCAGTCCC TAGCTTTGAA 21300
GAAGCAGCTT CTACATTTTG TTTTGAGGGT GCTGGCTTTG ATCAATGTAA TGGTGCTGTT 21360
TTAAATAATA CTGTAGACGT CATTAGGTTC AACCTTAATT TTACTACAAA TGTACAATCA 21420
GGTAAGGGTG CCACAGTGTT TTCATTGAAC ACAACGGGTG GTGTCACTCT TGAAATTTCA 21480
TGTTATACAG TGAGTGACTC GAGCTTTTTC AGTTACGGTG AAATTCCGTT CGGCGTAACT 21540
GATGGACCAC GGTACTGTTA CGTACACTAT AATGGCACAG CTCTTAAGTA TTTAGGAACA 21600
TTACCACCTA GTGTCAAGGA GATTGCTATT AGTAAGTGGG GCCATTTTA TATTAATGGT 21660
TACAATTTCT TTAGCACATT TCCTATTGAT TGTATATCTT TTAATTTGAC CACTGGTGAT 21720
AGTGACGTTT TCTGGACAAT AGCTTACACA TCGTACACTG AAGCATTAGT ACAAGTTGAA 21780
AACACAGCTA TTACAAAGGT GACGTATTGT AATAGTCACG TTAATAACAT TAAATGCTCT 21840
CAAATTACTG CTAATTTGAA TAATGGATTT TATCCTGTTT CTTCAAGTGA AGTTGGTCTT 21900
GTCAATAAGA GTGTTGTGTT ACTACCTAGC TTTTACACAC ATACCATTGT TAACATAACT 21960
ATTGGTCTTG GTATGAAGCG TAGTGGTTAT GGTCAACCCA TAGCCTCAAC ATTAAGTAAC 22020
ATCACACTAC CAATGCAGGA TCACAACACC GATGTGTACT GTATTCGTTC TGACCAATTT 22080
TCAGTTTATG TTCATTCTAC TTGCAAAAGT GCTTTATGGG ACAATATTTT TAAGCGAAAC 22140
TGCACGGACG TTTTAGATGC CACAGCTGTT ATAAAAACTG GTACTTGTCC TTTCTCATTT 22200
GATAAATTGA ACAATTACTT AACTTTTAAC AAGTTCTGTT TGTCGTTGAG TCCTGTTGGT 22260
GCTAATTGTA AGTTTGATGT AGCTGCCCGT ACAAGAACCA ATGAGCAGGT TGTTAGAAGT 22320
TTGTATGTAA TATATGAAGA AGGAGACAAC ATAGTGGGTG TACCGTCTGA TAATAGTGGT 22380
GTGCACGATT TGTCAGTGCT ACACCTAGAT TCCTGCACAG ATTACAATAT ATATGGTAGA 22440
ACTGGTGTTG GTATTATTAG ACAAACTAAC AGGACGCTAC TTAGTGGCTT ATATTACACA 22500
TCACTATCAG GTGATTTGTT AGGTTTTAAA AATGTTAGTG ATGGTGTCAT CTACTCTGTA 22560
ACGCCATGTG ATGTAAGCGC ACAAGCAGCT GTTATTGATG GTACCATAGT TGGGGCTATC 22620
ACTTCCATTA ACAGTGAACT GTTAGGTCTA ACACATTGGA CAACAACACC TAATTTTTAT 22680
TACTACTCTA TATATAATTA CACAAATGAT AGGACTCGTG GCACTGCAAT TGACAGTAAT 22740
GATGTTGATT GTGAACCTGT CATAACCTAT TCTAACATAG GTGTTTGTAA AAATGGTGCT 22800
TTTGTTTTTA TTAACGTCAC ACATTCTGAT GGAGACGTGC AACCAATTAG CACTGGTAAT 22860
GTCACGATAC CTACAAACTT TACCATATCC GTGCAAGTCG AATATATTCA GGTTTACACT 22920
```

FIGURE 14-10

```
ACACCAGTGT CAATAGACTG TTCAAGATAT GTTTGTAATG GTAACCCTAG GTGTAACAAA 22980
TTGTTAACAC AATACGTTTC TGCATGTCAA ACTATTGAGC AAGCACTTGC AATGGGTGCC 23040
AGACTTGAAA ACATGGAGGT TGATTCCATG TTGTTTGTTT CTGAAAATGC CCTTAAATTG 23100
GCATCTGTTG AAGCATTCAA TAGTTCAGAA ACTTTAGACC CTATTTACAA AGAATGGCCT 23160
AATATAGGTG GTTCTTGGCT AGAAGGTCTA AAATACATAC TTCCGTCCCA TAATAGCAAA 23220
CGTAAGTATC GTTCAGCTAT AGAGGACTTG CTTTTTGATA AGGTTGTAAC ATCGGTTTA 23280
GGTACAGTTG ATGAAGATTA TAAACGTTGT ACAGGTGGTT ATGACATAGC TGACTTAGTA 23340
TGTGCTCAAT ACTATAATGG CATCATGGTG CTACCTGGTG TGGCTAATGC TGACAAAATG 23400
ACTATGTACA CAGCATCCCT TGCAGGTGGT ATAACATTAG GTGCACTTGG TGGAGGCGCC 23460
GTGGCTATAC CTTTTGCAGT AGCAGTTCAG GCTAGACTTA ATTATGTTGC TCTACAAACT 23520
GATGTATTGA ACAAAAACCA GCAGATTCTG GCTAGTGCTT TCAATCAAGC TATTGGTAAC 23580
ATTACACAGT CATTTGGTAA GGTTAATGAT GCTATACATC AAACATCACG AGGTCTTGCT 23640
ACTGTTGCTA AAGCATTGGC AAAAGTGCAA GATGTTGTCA ACATACAAGG GCAAGCTTTA 23700
AGCCACCTAA CAGTACAATT GCAAAATAAT TTCCAAGCCA TTAGTAGTTC TATTAGTGAC 23760
ATTTATAATA GGCTTGACGA ATTGAGTGCT GATGCACAAG TTGACAGGCT GATCACAGGA 23820
AGACTTACAG CACTTAATGC ATTTGTGTCT CAGACTCTAA CCAGACAAGC GGAGGTTAGG 23880
GCTAGTAGAC AACTTGCCAA AGACAAGGTT AATGAATGCG TTAGGTCTCA GTCTCAGAGA 23940
TTCGGATTCT GTGGTAATGG TACACATTTG TTTTCACTCG CAAATGCAGC ACCAAATGGC 24000
ATGATTTTCT TTCACACAGT GCTATTACCA ACGGCTTATG AAACTGTGAC TGCTTGGCCA 24060
GGTATTTGTG CTTCAGATGG TGATCGCACT TTTGGACTTG TCGTTAAAGA TGTCCAGTTG 24120
ACTTTGTTTC GTAATCTAGA TGACAAGTTC TATTTGACCC CCAGAACTAT GTATCAGCCT 24180
AGAGTTGCAA CTAGTTCTGA CTTTGTTCAA ATTGAAGGGT GCGATGTGCT GTTTGTTAAT 24240
GCAACTGTAA GTGATTTGCC TAGTATTATA CCTGATTATA TTGATATTAA TCAGACTGTT 24300
CAAGACATAT TAGAAAATTT TAGACCAAAT TGGACTGTAC CTGAGTTGAC ATTTGACATT 24360
TTTAACGCAA CCTATTTAAA CCTGACTGGT GAAATTGATG ACTTAGAATT TAGGTCAGAA 24420
AAGCTACATA ACACCACTGT AGAACTTGCC ATTCTCATTG ACAACATTAA CAATACATTA 24480
GTCAATCTTG AATGGCTCAA TAGAATTGAA ACCTATGTAA AATGGCCTTG GTATGTGTGG 24540
CTACTAATAG GCTTAGTAGT AATATTTTGC ATACCATTAC TGCTATTTTG CTGTTGTAGT 24600
ACAGGTTGCT GTGGATGCAT AGGTTGTTTA GGAAGTTGTT GTCACTCTAT ATGTAGTAGA 24660
AGACAATTTG AAAATTACGA ACCAATTGAA AAAGTGCACG TCCATTAAAT TTAAAATGTT 24720
AATTCTATCA TCTGCTATAA TAGCAGTTGT TTCTGCTAGA GAATTTTGTT AAGGATGATG 24780
AATAAAGTCT TTAAGAACTA AACTTACGAG TCATTACAGG TCCTGTATGG ACATTGTCAA 24840
ATCCATTTAC ACATCCGTAG ATGCTGTACT TGACGAACTT GATTGTGCAT ACTTTGCTGT 24900
AACTCTTAAA GTAGAATTTA AGACTGGTAA ATTACTTGTG TGTATAGGTT TTGGTGACAC 24960
ACTTCTTGCT GCTAAGGATA AAGCATATGC TAAGCTTGGT CTCTCCATTA TTGAAGAAGT 25020
CAATAGTCAT ATAGTTGTTT AATATCATTA AACACACAAA ACCCAAAGCA TTAAGTGTTA 25080
CAAAACAATT AAAGAGAGAT TATAGAAAAA CTGTCATTCT AAATTCCATG CGAAAATGAT 25140
TGGTGGACTT TTTCTTAGTA CTCTGAGTTT TGTAATTGTT AGTAACCATT CTATTGTTAA 25200
TAACACAGCA AATGTGCATC ATATACAACA AGAACGTGTT ATAGTACAAC AGCATCATGT 25260
TGTTAGTGCT AGAACACAAA ACTATTACCC AGAGTTCAGC ATCGCTGTAC TCTTTGTATC 25320
TTTTCTAGCT TTGTACCGTA GTACAAACTT TAAGACGTGT GTCGGCATCT TAATGTTTAA 25380
GATTTTATCA ATGACACTTT TAGGACCTAT GCTTATAGCA TATGGTTACT ACATTGATGG 25440
CATTGTTACA ACAACTGTCT TATCTTTAAG ATTTGTCTAC TTAGCATACT TTTGGTATGT 25500
```

FIGURE 14-11

```
TAATAGTAGG TTTGAATTTA TTTTATACAA TACAACGACA CTCATGTTTG TACATGGCAG 25560
AGCTGCACCG TTTATGAGAA GTTCTCACAG CTCTATTTAT GTCACATTGT ATGGTGGCAT 25620
AAATTATATG TTTGTGAATG ACCTCACGTT GCATTTTGTA GACCCTATGC TTGTAAGCAT 25680
AGCAATACGT GGCTTAGCTC ATGCTGATCT AACTGTAGTT AGAGCAGTTG AACTTCTCAA 25740
TGGTGATTTT ATTTATGTAT TTTCACAGGA GCCCGTAGTC GGTGTTTACA ATGCAGCCTT 25800
TTCTCAGGCG GTTCTAAACG AAATTGACTT AAAAGAAGAA GAAGAAGACC ATACCTATGA 25860
CGTTTCCTAG GGCATTGACT GTCATAGATG ACAATGGAAT GGTCATTAAC ATCATTTTCT 25920
GGTTCCTGTT GATAATTATA TTGATATTAC TTTCAATAGC ATTGCTAAAT ATAATTAAGC 25980
TATGCATGGT GTGTTGCAAT TTAGGAAGGA CAGTTATTAT TGTTCCAGCG CAACATGCTT 26040
ACGATGCCTA TAAGAATTTT ATGCAATTA AAGCATACAA CCCCGATGGA GCACTCCTTG 26100
CTTGAACTAA ACAAAATGAA GATTTTGTTA ATATTAGCGT GTGTGATTGC ATGCGCATGT 26160
GGAGAACGCT ATTGTGCTAT GAAATCCGAT ACAGATTGT CATGTCGCAA TAGTACAGCG 26220
TCTGATTGTG AGTCATGCTT CAACGGAGGC GATCTTATTT GGCATCTTGC AAACTGGAAC 26280
TTCAGCTGGT CTATAATATT GATCGTTTTT ATAACTGTGC TACAATATGG AAGACCTCAA 26340
TTCAGCTGGT TCGTGTATGG CATTAAAATG CTTATAATGT GGCTATTATG GCCCGTTGTT 26400
TTGGCTCTTA CGATTTTTAA TGCATACTCG GAATACCAAG TGTCCAGATA TGTAATGTTC 26460
GGCTTTAGTA TTGCAGGTGC AATTGTTACA TTTGTACTCT GGATTATGTA TTTTGTAAGA 26520
TCCATTCAGT TGTACAGAAG GACTAAGTCT TGGTGGTCTT TCAACCCTGA AACTAAAGCA 26580
ATTCTTTGCG TTAGTGCATT AGGAAGAAGC TATGTGCTTC CTCTCGAAGG TGTGCCAACT 26640
GGTGTCACTC TAACTTTGCT TTCAGGGAAT TTGTACGCTG AAGGGTTCAA AATTGCAGGT 26700
GGTATGAACA TCGACAATTT ACCAAAATAC GTAATGGTTG CATTACCTAG CAGGACTATT 26760
GTCTACACAC TTGTTGGCAA GAAGTTGAAA GCAAGTAGTG CGACTGGATG GGCTTACTAT 26820
GTAAAATCTA AAGCTGGTGA TTACTCAACA GAGGCAAGAA CTGATAATTT GAGTGAGCAA 26880
GAAAAATTAT TACATATGGT ATAACTAAAC TTCTAAATGG CCAACCAGGG ACAACGTGTC 26940
AGTTGGGGAG ATGAATCTAC CAAAACACGT GGTCGTTCCA ATTCCCGTGG TCGGAAGAAT 27000
AATAACATAC CTCTTTCATT CTTCAACCCC ATAACCCTCC AACAAGGTTC AAAATTTTGG 27060
AACTTATGTC CGAGAGACTT TGTACCCAAA GGAATAGGTA ACAGGGATCA ACAGATTGGT 27120
TATTGGAATA GACAAACTCG CTATCGCATG GTGAAGGGCC AACGTAAAGA GCTTCCTGAA 27180
AGGTGGTTCT TCTACTACTT AGGTACTGGA CCTCATGCAG ATGCCAAATT TAAAGATAAA 27240
TTAGATGGAG TTGTCTGGGT TGCCAAGGAT GGTGCCATGA ACAAACCAAC CACGCTTGGT 27300
AGTCGTGGTG CTAATAATGA ATCCAAAGCT TTGAAATTCG ATGGTAAAGT GCCAGGCGAA 27360
TTTCAACTTG AAGTTAATCA ATCAAGAGAC AATTCAAGGT CACGCTCTCA ATCTAGATCT 27420
CGGTCTAGAA ATAGATCTCA ATCTAGAGGC AGGCAACAAT TCAATAACAA GAAGGATGAC 27480
AGTGTAGAAC AAGCTGTTCT TGCCGCACTT AAAAAGTTAG GTGTTGACAC AGAAAAACAA 27540
CAGCAACGCT CTCGTTCTAA ATCTAAAGAA CGTAGTAACT CTAAGACAAG AGATACTACA 27600
CCTAAGAATG AAAACAAACA CACCTGGAAG AGAACTGCAG GTAAAGGTGA TGTGACAAGA 27660
TTTTATGGAG CTAGAAGCAG TTCAGCCAAT TTTGGTGACA CTGACCTCGT TGCCAATGGG 27720
AGCAGTGCCA AGCATTACCC ACAACTGGCT GAATGTGTTC CATCTGTGTC TAGCATTCTG 27780
TTTGGAAGCT ATTGGACTTC AAAGGAAGAT GGCGACCAGA TAGAAGTCAC GTTCACACAC 27840
AAATACCACT TGCCAAAGGA TGATCCTAAG ACTGGACAAT TCCTTCAGCA GATTAATGCC 27900
TATGCTCGTC CATCAGAAGT GGCAAAAGAA CAGAGAAAAA GAAATCTCG TTCTAAATCT 27960
GCAGAAAGGT CAGAGCAAGA TGTGGTACCT GATGCATTAA TAGAAAATTA TACAGATGTG 28020
TTTGATGACA CACAGGTTGA GATAATTGAT GAGGTAACGA ACTAAACGAG ATGCTCGTCT 28080
```

FIGURE 14-12

```
TCCTCCATGC TGTATTTATT ACAGTTTTAA TCTTACTACT AATTGGTAGA CTCCAATTAT 28140
TAGAAAGACT ATTACTTAAT CACTCTTTCA ATCTTAAAAC TGTCAATGAC TTTAATATCT 28200
TATATAGGAG TTTAGCAGAA ACCAGATTAC TAAAAGTGGT GCTTCGAGTA ATCTTTCTAG 28260
TCTTACTAGG ATTTTGCTGC TACAGATTGT TAGTCACATT AATGTAAGGC AACCCGATGT 28320
CTAAAACTGG TTTTTCCGAG GAATTACTGG TCATCGCGCT GTCTACTCTT GTACAGAATG 28380
GTAAGCACGT GTAATAGGAG GTACAAGCAA CCCTATTGCA TATTAGGAAG TTTAGATTTG 28440
ATTTGGCAAT GCTAGATTTA GTAATTTAGA GAAGTTTAAA GATCCGCTAC GACGAGCCAA 28500
CAATGGAAGA GCTAACGTCT GGATCTAGTG ATTGTTTAAA ATGTAAAATT GTTTGAAAAT 28560
TTTCCTTTTG ATAGTGATAC AAAAAAAA                                  28588
```

SEQUENCE LISTING

```
<160> NUMBER OF SEQ ID NOS: 15

<210> SEQ ID NO 1
<211> LENGTH: 28588
<212> TYPE: DNA
<213> ORGANISM: Porcine Transmissible Gastroenteritis V

<400> SEQUENCE: 1
acttttaaag taaagtgagt gtagcgtggc tatatctctt cttttacttt aactagcctt     60
gtgctagatt ttgtcttcgg acaccaactc gaactaaacg aaatatttgt ctttctatga    120
aatcatagag gacaagcgtt gattatttcc attcagtttg gcaatcactc cttggaacgg    180
ggttgagcga acggtgcagt agggttccgt ccctatttcg taagtcgcct agtagtagcg    240
agtgcggttc cgcccgtaca acgttgggta gaccgggttc cgtcctgtga tctccctcgc    300
cggccgccag gagaatgagt tccaaacaat tcaagatcct tgttaatgag gactatcaag    360
tcaacgtgcc tagtcttcct attcgtgacg tgttacagga aattaagtac tgctaccgta    420
atggatttga gggctatgtt ttcgtaccag aatactgtcg tgacctagtt gattgcgatc    480
gtaaggatca ctacgtcatt ggtgttcttg gtaacggagt aagtgatctt aaacctgttc    540
ttcttaccga accctccgtc atgttgcaag gctttattgt tagagctaac tgcaatggcg    600
ttcttgagga ctttgacctt aaaattgctc gcactggcag aggtgccata tatgttgatc    660
aatacatgtg tggtgctgat ggaaaaccag tcattgaagg cgattttaag gactacttcg    720
gtgatgaaga catcattgaa tttgaaggag aggagtacca ttgcgcttgg acaactgtgc    780
gcgatgagaa accgctgaat cagcaaactc tctttaccat tcaggaaatc caatacaatc    840
tggacattcc tcataaattg ccaaactgtg ctactagaca tgtagcacca ccagtcaaaa    900
agaactctaa aatagttctg tctgaagatt acaagaagct ttatgatatc ttcggatcac    960
cctttatggg aaatggtgac tgtcttagca aatgctttga cactcttcat tttatcgctg   1020
ctactcttag atgcccgtgt ggttctgaaa gtagcggcgt tggagattgg actggtttta   1080
agactgcctg ttgtggtctt tctggcaaag ttaagggtgt cactttgggt gatattaagc   1140
ctggtgatgc tgttgtcact agtatgagcg caggtaaggg agttaagttc tttgccaatt   1200
```

-continued

```
gtgttcttca atatgctggt gatgttgaag gtgtctccat ctggaaagtt attaaaactt    1260
ttacagttga tgagactgta tgcacccctg gttttgaagg cgaattgaac gacttcatca    1320
aacctgagag caaatcacta gttgcatgca gcgttaaaag agcattcatt actggtgata    1380
ttgatgatgc tgtacatgat tgtatcatta caggaaaatt ggatcttagt accaaccttt    1440
ttggtaatgt tggtctatta ttcaagaaga ctccatggtt tgtacaaaag tgtggtgcac    1500
ttttttgtaga cgcttggaaa gtagtagagg agctttgtgg ttcactcaca cttacataca    1560
agcaaattta tgaagttgta gcatcacttt gcacttctgc ttttacgatt gtaaactaca    1620
agccaacatt tgtggttcca gacaatcgtg ttaaagatct tgtagacaag tgtgtgaaag    1680
ttcttgtaaa agcatttgat gtttttacgc agattatcac aatagctggt attgaggcca    1740
aatgctttgt gctggtgct aaatacctgt tgttcaataa tgcacttgtc aaacttgtca    1800
gtgttaaaat ccttggcaag aagcaaaagg gtcttgaatg tgcattcttt gctactagct    1860
tggttggtgc aactgttaat gtgacaccta aagaacaga gactgccact atcagcttga    1920
acaaggttga tgatgttgta gcaccaggag agggttatat cgtcattgtt ggtgatatgg    1980
cttctactaa gagtggtgaa tattatttca tgatgtctag tcctaatttt gttcttacta    2040
acaatgtttt taaagcagtt aaagttccat cttatgacat cgtttatgat gttgataatg    2100
ataccaaaag caaaatgatt gcaaaacttg gttcatcatt tgaatatgat ggtgatattg    2160
atgctgctat tgtaaaagtc aatgaactac tcattgaatt taggcagcaa agcttgtgct    2220
tcagagcttt taaggacgac aaaagcattt ttgttgaagc ctattttaaa agtataaaa    2280
tgccagcatg ccttgcaaaa catattggtt tgtggaacat cataaagaaa gattcatgta    2340
agaggggttt tcttaatctc ttcaatcact gaatgaatt ggaagatatc aaagaaacta    2400
atattcaggc tattaaaaac attctttgcc ctgatcctct tcttgatctg gattatggtg    2460
ccatttggta caattgcatg ccaggttgct ctgatccttc agttttgggg agtgttcaac    2520
ttttgatcgg taatggtgtg aaagtagttt gtgatggctg caaaggtttt gctaaccaac    2580
tttcaaaagg ttacaacaag ctctgtaatg cggctcgcaa tgatattgag atcggtggta    2640
taccattttc cacttttaaa acacctacaa atactttat tgaaatgaca gatgctatct    2700
attcagttat tgaacaaggt aaggcattat cctttagaga tgctgatgtg ccagttgtag    2760
acaatggtac catttctact gctgattggt ctgaacccat tctgcttgaa cctgctgaat    2820
atgtaaaacc aaagaacaat ggtaatgtca ttgttattgc aggttataca tttttataaag    2880
atgaggatga acatttttat ccttatggtt ttggtaaaat tgtgcagaga atgtataata    2940
aaatgggtgg tggtgacaaa actgtctcat tttcagaaga agtagatgtt caagaaattg    3000
cacctgttac acgtgttaaa cttgaattcg aatttgacaa tgaaattgta actggtgttc    3060
ttgaacgggc tattggtact agatacaaat ttactggtac aacttgggaa gaatttgaag    3120
agtctatttc tgaagaactc gatgcaatct ttgatactct agcaaccaa ggtgtcgaac    3180
ttgaaggtta cttcatttat gacacttgtg gtggctttga tataaaaaat ccagatggta    3240
ttatgatctc tcagtatgat atcaatatta ctgctgatga aaaatcagaa gttagtgcat    3300
caagtgaaga agaagaagtt gaatctgttg aagaagatcc tgagaatgaa attgtagaag    3360
catctgaagg tgctgaaggg acttcttctc aagaagaggt tgaaacagta gaagttcag    3420
atattacttc tacagaagaa gatgttgaca ttgttgaagt atctgctaaa gatgacccctt    3480
gggctgcagc tgttgatgta caagaagctg aacaatttaa tccttctcta ccacctttca    3540
agacaacgaa tctcaacgga aaaattatcc ttaagcaagg ggataataat tgttggataa    3600
```

```
atgcttgttg ctatcagctt caggcctttg attttttcaa caatgaagct tgggagaaat   3660
ttaagaaagg tgatgtcatg actttgtaa accttttgtta tgcagcaaca acactagcaa   3720
gaggtcattc tggtgatgca gagtatcttc ttgaacttat gctcaatgat tatagcacag   3780
ccaagatagt acttgcagct aagtgtggtt gtggtgaaaa agaaattgtt ttggaaagag   3840 ctgttttta actcaccca cttaaggaga gttttaatta tggtgtttgt ggtgactgca    3900
tgcaagttaa cacctgtaga tttttaagtg ttgaaggctc tggtgttttt gttcatgaca   3960
tattaagcaa gcaaacgcca gaagctatgt ttgttgtcaa acctgttatg catgcagttt   4020
acactggcac aactcaaaat ggccattaca tggttgatga tattgaacac ggttattgtg   4080
tagatggtat gggtattaaa ccacttaaga acggtgttta tacatccaca ttgttcatta   4140
atgccaatgt aatgactaga gctgaaaaac caaacaaga gtttaaagtt gaaaaagtag    4200
aacagcaacc gatagtggag gaaaacaaat cctctattga aaagaggaa attcaaagtc    4260 ctaaaaacga tgaccttata cttccatttt acaaagctgg taaactttcc ttttatcagg   4320
gtgctttgga tgttttgatc aatttcttgg aacctgatgt tattgttaat gctgctaatg   4380
gtgatcttaa acacatgggt ggtgtcgcaa gagccatcga tgttttcact ggtggcaaat   4440
taacagaacg ttctaaggat tatcttaaaa agaacaaatc tattgctcct ggtaatgctg   4500
ttttctttga aaatgtcatt gagcatctta gtgttttgaa tgcagttgga ccacgtaatg   4560
gtgacagccg agttgaagcc aaactttgta atgtttacaa agcaattgca aagtgtgaag   4620 gaaaatatt aacaccactt attagtgttg gtatcttaa tgttagactt gaaacatcat    4680
tgcagtgctt acttaagact gtgaatgaca ggggattgaa tgtcttcgta tacactgacc   4740
aggagaggca aactattgag aatttcttct cttgttctat ccctgtcaat gttactgagg   4800
ataatgttaa ccatgaacgt gtgtctgttt cttttgacaa acatacggt gaacagctta    4860 agggcaccgt tgtcatcaaa gacaaagatg ttacaaacca gttgcctagc gcttttgatg   4920
ttggtcaaaa agttattaag gctattgata tagattggca agctcattat ggtttccgtg   4980
atgctgctgc ttttagcgct agtagtcatg atgcttataa atttgaagtt gttacacata   5040
gcaatttcat tgtgcataag cagactgaca caactgttg gattaatgca atttgtcttg    5100
cattacagag actcaagcca cagtggaaat ttcctggtgt tagaggtctc tggaatgaat   5160
ttcttgagcg taaaacacaa ggttttgtac atatgttgta tcacatttct ggagtaaaga   5220
aaggtgagcc aggtgatgct gaattaatgc tgcataaact tggtgacttg atggacaatg   5280
attgtgaaat cattgtcaca cacactacag catgtgacaa gtgcgcaaaa gtagaaaagt   5340
ttgttggacc agtggtagca gcacctcttg caattcatgg cactgacgaa acatgtgtgc   5400
atggcgttag tgtcaatgtc aaagtcaccc aaattaaggg cactgttgct attacttctt   5460
tgattggtcc tattattgga gaagtactag aagcaactgg ttatatttgt tatagcggtt   5520
ctaacaggaa tggtcattac acctattacg ataaccgtaa tggattagtg ttgatgcag    5580 aaaaggctta ccattttaat agagactat tacaggtcac aacagctatt gcaagtaatt    5640
tcgttgtcaa gaaaccacaa gcagaggaaa gacctaagaa ttgtgctttt aacaaagttg   5700
cagcatctcc taagattgta caagaacaaa aattgttggc tattgaaagt ggtgctaact   5760
atgctcttac tgaatttgga agatatgctg acatgttctt tatggctgga gataaaattc   5820
ttaggttgct gctgaagtc tttaaatatt tgctggtttt atttatgtgt cttagaagta    5880
ctaagatgcc taaagttaaa gtcaaaccac ctcttgcatt taaagatttt ggtgctaagg   5940
```

```
tcagaacgct caattacatg agacaattga acaaaccctc tgtctggcgt tacgcaaaac   6000 tagtttatt gttgatagca atatataatt tcttttattt gtttgtcagt ataccagtag   6060
tgcataaatt aacatgtaac ggtgctgtac aggcatataa aaattctagt tttataaagt   6120
ctgcagtctg tggcaactct attttatgca aagcctgttt ggcttcttat gatgagttgg   6180
ctgattttca acatctccaa gttacttggg atttcaaatc tgacccacta tggaacagac   6240
tggtacaatt gtcttacttt gcattcttgg ctgttttgg taataactat gttaggtgtt   6300
ttcttatgta ttttgtatct cagtacctca acctttggct ttcttatttt ggttatgtag   6360
agtacagttg gttttgcat gttgtcaact ttgaatccat ctcagctgag tttgtgatcg   6420
tagttatagt ggttaaggca gttctcgccc ttaaacatat tgttttcgca tgctcaaacc   6480
cgtcttgcaa aacgtgctct aggactgcaa ggcagacacg tattcctatt caagttgttg   6540
ttaatggttc aatgaagact gtttatgttc atgctaatgg tactggtaaa ttctgcaaga   6600
aacacaattt ttattgtaag aactgtgatt cttatggctt tgaaaacaca ttcatctgtg   6660
acgaaattgt acgtgatctc agtaatagtg ttaaacaaac tgtttacgcc actgatagat   6720
ctcatcaaga agtcacaaaa gttgaatgtt cagatggctt ttacagattt tatgttggtg   6780
atgaattcac ttcatatgac tatgatgtaa aacacaagaa atacagtagt caagaggttc   6840
tcaagagcat gctcttgctt gatgacttca ttgtgtacag tccatctggt tctgctcttg   6900
caaatgttag aaatgcctgt gtttactttt cacaacttat tggtaagcct attaagattg   6960
ttaacagtga tttgcttgaa gacctctctg tagattttaa aggggcactt tttaatgcta   7020
aaaagaatgt aattaagaat tctttcaatg ttgatgtctc agaatgcaaa aatcttgacg   7080
aatgttacag ggcttgcaat cttaatgttt cattttctac atttgaaatg gctgtcaaca   7140
atgctcatag gtttggtatt ctgattactg atcgttcttt taacaatttc tggccatcaa   7200
aagttaagcc tggttcatct ggtgtgtcgg ccatggacat tggtaagtgt atgacttctg   7260
atgctaagat tgttaatgct aaagttttaa ctcaacgtgg taaaagtgtt gtttggctta   7320
gccaggattt tgctgcactt agctcaactg ctcagaaagt tttggttaaa acttttgtag   7380
aagaaggtgt caacttttca ctcacattta atgctgtagg ttcagatgat gatcttcctt   7440
atgaaagatt cactgaatct gtgtctccaa aaagtggttc aggcttttc gatgtaatta   7500 cacagcttaa acaaattgtg attttggttt ttgttttat ctttatttgt ggtttgtgct   7560
ctgtttacag tgttgctaca cagtcctaca ttgaatctgc tgaaggctat gactacatgg   7620
ttattaagaa tggaattgtt caaccttttg acgataccat ttcatgtgtt cataacactt   7680
ataaaggatt cggtgactgg tttaaagcta agtatggttt tatccctact tttggtaaat   7740
catgtccaat tgttgtagga actgttttg atcttgaaaa tatgagacca attcctgacg   7800
tgcctgcata tgtttctatt gtgggtagat ctcttgtttt cgctattaat gctgcttttg   7860
gtgttactaa tatgtgctat gatcatactg gcaatgcagt tagtaaggac tcttactttg   7920
atacttgtgt gtttaatact gcgtgcacca ctcttacagg tcttggtggt acaattgtat   7980
attgtgcaaa gcaaggttta gttgaaggtg ctaagctcta tagtgatctt atgccagact   8040
attattatga gcatgctagt ggtaacatgg ttaaattgcc agcaattatt agaggacttg   8100
gtctacgttt tgtgaaaaca caggctacaa cttattgtag agtgggagag tgcattgata   8160
gtaaagctgg ttttttgctt ggtggcgata actggtttgt ctacgacaat gagtttggca   8220
atggatacat ctgtggtaat tctgtgctag gattctttaa gaatgtcttc aaactcttta   8280
actctaacat gtctgtggta gctacatctg gtgcgatgct tgttaacatt attattgcat   8340
```

-continued

```
gcttagctat tgcaatgtgt tatggtgttc ttaagtttaa gaagattttt ggtgattgta      8400
cttccctcat tgttatgatc attgtcaccc ttgttgtgaa caatgtgtct tattttgtca      8460
ctcaaaacac gttctttatg atcatctacg ccattgttta ctattttata acaagaaaac      8520
ttgcataccc aggcattctt gatgctgggt ttattattgc ttatattaat atggctccat      8580
ggtacgtgat taccgcatat atcctagttt tcctctatga ctcactccct tcactgttta      8640
aacttaaagt ttcaacaaat cttttttgaag gtgataaatt tgtgggtaac tttgaatctg      8700
ctgctatggg tacttttgtt attgacatgc gttcatatga aactattgtt aattctactt      8760
ctattgctag aattaaatca tatgctaaca gcttcaataa atataagtac tacacaggtt      8820
caatgggaga agctgactac agaatggctt gctatgctca tcttggtaaa gctcttatgg      8880
actattctgt taatagaaca gacatgcttt acacacctcc tactgttagt gttaattcta      8940
cacttcagtc aggtttgcgg aaaatggcac agcctagtgg tcttagtagag ccttgcattg      9000 taagagtttc ctatggtaac aatgtgctta atggtttatg gttaggagat gaagtcatt      9060 gccctagaca tgttattgct agtgatacca cacgtgttat caactatgaa atgaaatgt      9120 ctagtgtgag acttcacaac ttttcagttt ctaagaataa tgtgtttttg ggtgttgtgt      9180
ctgccagata taagggtgtg aatcttgtac ttaaagtcaa ccaggttaat cctaacacac      9240
cagaacataa atttaagtct attaaagctg gtgaaagttt taacattctt gcttgttatg      9300
aaggatgtcc tggcagtgtt tatggtgtca acatgagaag tcaaggtacc attaaaggat      9360
cttttatagc tggtacttgt ggatcagtag gttatgtgtt agaaaatgga attctctatt      9420
ttgtatacat gcatcactta gaacttggaa atggctcgca tgttggttcc aattttgaag      9480
gagaaatgta cggtggttat gaagatcaac ctagcatgca attggaaggt actaatgtca      9540
tgtcatcaga taatgtggtt gcattcctat atgctgcact tatcaatggt gaaaggtggt      9600
ttgttacaaa cacatcgatg tcattagaat catacaatac atgggccaaa actaacagtt      9660
tcacagaact ttcttcaact gatgcttta gcatgttggc tgcaaaaact ggtcaaagtg      9720
ttgagaaatt actagatagc atcgtaagac tcaacaaggg ttttggaggt cgtactatac      9780
tttcttatgg ctcattgtgt gacgagttca ctccaactga agtcataagg caaatgtatg      9840
gtgtaaatct tcaggctggt aaagtaaaat ctttcttcta ccctattatg actgcaatga      9900
caattctctt tgccttttgg cttgaattct ttatgtacac accccttcact tggattaatc      9960 caactttgt tagcattgta ttggctgtta caactttgat ctcgacggtt tttgtctctg      10020
gcatcaaaca taagatgttg ttcttttatgt cttttgtcct tcctagtgtt atccttgtga      10080
cagcacacaa tttgttctgg gactttttctt actatgaaag tcttcagtca attgttgaga      10140
atactaacac tatgttttg cctgttgaca tgcaaggtgt catgctcaca gtgttttgct      10200
ttattgtctt tgttacatat agtgttagat tcttcacttg caaacaatca tggttctcac      10260
ttgctgtgac aactattctt gtgatcttta acatggttaa aatctttgga acatctgatg      10320
aaccatggac tgaaaaccaa attgctttct gctttgtgaa catgcttact atgattgtca      10380
gtcttactac aaaggattgg atggttgtca ttgcatcata cagaattgca tattatattg      10440
ttgtatgtgt aatgccatct gcttttgtat ctgactttgg gtttatgaag tgtattagca      10500
ttgtttacat ggcgtgcggt tatttgtttt gttgctatta tggcatcctt tattgggtta      10560 acagattttac atgcatgact tgtggtgttt atcaattcac tgtgtctgca gctgaactta      10620
aatacatgac cgctaacaac cttctgcac ctaagaacgc atatgacgct atgattctta      10680
```

```
gtgctaaatt gattggtgtt ggaggtaaga gaaacatcaa aatttcaact gtacagtcaa   10740
aacttacaga gatgaaatgt accaatgttg tcttgcttgg tcttttatct aaaatgcatg   10800
tcgagtctaa ctcaaaagag tggaactatt gtgttggact acacaatgag ataaaccttt   10860
gtgacgatcc tgaaatcgtt cttgagaaac tgttagctct tattgcattc ttcttgtcca   10920
aacataacac ttgtgacctt agcgaactta ttgaatcata ctttgagaac accaccatac   10980
tccagagtgt ggcttcagct tatgctgcat tgcctagctg gattgcactt gaaaaagctc   11040
gcgctgatct tgaagaggct aagaaaaatg atgttagccc tcaaattttg aagcagctta   11100
ctaaagcatt taacattgcc aagagtgatt ttgagcgcga agcatcagtg caaagaaac    11160 tcgacaaaat ggctgagcag gctgcagcta gtatgtataa agaagcacga gctgtggaca   11220
gaaagtcaaa gattgtttct gctatgcata gcctactttt tggtatgctt aagaaacttg   11280
atatgtccag tgtcaacact attattgacc aggctcgtaa tggtgttcta cctttaagta   11340
tcattccagc tgcatcagct acaagacttg ttgttattac acctagcctt gaagtgtttt   11400
ccaagattag gcaagaaaac aatgttcatt atgctggtgc tatttggact attgttgaag   11460
ttaaagatgc taatggttca catgtacatc ttaaggaagt caccgctgct aatgaattaa   11520
accttacttg gccattgagc attacttgtg agagaaccac aaagcttcag aacaatgaaa   11580
ttatgccagt aaacttaaaa gaaagagctg tcagagcgtc agcaactctt gatggtgaag   11640
ctttcggcag tggaaaggct cttatggcat ctgaaagtgg aaaaagcttt atgtatgcat   11700
ttatagcctc agacaacaat cttaagtatg ttaagtggga gagcaataat gatattatac   11760
ctattgaact tgaagctcca ttgcgtttct atgttgacgg cgctaatggt cctgaagtca   11820
agtatttgta ttttgtcaag aatttaaaca ctcttagacg tggtgccgtt cttggttata   11880
tcggtgcaac agttcgtctg caagctggta aacccactga acatccatct aacagtagtt   11940
tattgacatt gtgtgctttt tcacctgatc ctgctaaagc atatgttgat gctgttaaga   12000
gaggcatgca accagttaat aactgtgtaa aaatgctctc aaatggtgct ggtaatggta   12060
tggctgttac aaacggtgtc gaagctaaca cacaacagga ctcttatggt ggtgcttcag   12120
tttgtattta ttgcagatgc catgttgaac atcctgctat tgatggatta tgccgctaca   12180
aaggtaagtt cgtgcaaata ccaactggca cacaagatcc aattcggttc tgtattgaaa   12240
atgaagtttg tgttgtctgt ggttgttggc ttaacaatgg ttgcatgtgc gatcgtactt   12300
ctatgcagag ttttactgtt gatcaaagtt atttaaacga gtgcggggtt ctagtgcagc   12360
tcgactagaa ccctgcaatg gtactgatcc agaccatgtt agtagagctt ttgacatcta   12420
caacaaagat gttgcgtgta ttggtaaatt ccttaagacg aattgttcaa gatttaggaa   12480
tttggacaaa catgatgcct actacattgt caaacgttgt acaagaccg ttatggacca    12540 tgagcaagtc tgttataacg atcttaaaga ttctggtgct gttgctgagc atgacttctt   12600
cacatataaa gagggtagat gtgagttcgg taatgttgca cgtaggaatc ttacaaagta   12660
cacaatgatg gatctttgtt acgctatcag aaattttgat gaaaagaact gtgaagttct   12720
caaagaaata ctcgtgacag taggtgcttg cactgaagaa ttctttgaaa ataaagattg   12780
gtttgatcca gttgaaaatg aagccataca tgaagtttat gcaaaacttg acccattgt    12840 agccaatgct atgcttaaat gtgttgcttt ttgcgatgcg atagtggaaa aaggctatat   12900
aggtgttata acacttgaca accaagatct taatggcaat ttctacgatt tcggcgattt   12960
cgtgaagact gctccgggtt ttggttgcgc ttgtgttaca tcatattatt cttatatgat   13020
gcctttaatg gggatgactt catgcttaga gtctgaaaac tttgtgaaaa gtgacatcta   13080
```

```
tggttctgat tataagcagt atgatttact agcttatgat tttaccgaac ataaggagta   13140
ccttttccaa aaatacttta agtactggga tcgcacatat cacccaaatt gttctgattg   13200
tactagtgac gagtgtatta ttcattgtgc taattttaac acattgtttt ctatgacaat   13260
accaatgaca gcttttggac cacttgtccg taaagttcat attgatggtg taccagtagt   13320
tgttactgca ggttaccatt tcaaacaact tggtatagta tggaatcttg atgtaaaatt   13380
agacacaatg aagttgagca tgactgatct tcttagattt gtcacagatc caacacttct   13440
tgtagcatca agccctgcac ttttagacca gcgtactgtc tgtttctcca ttgcagcttt   13500
gagtactggt attacatatc agacagtaaa accaggtcac tttaacaaag atttctacga   13560
tttcataaca gagcgtggat tctttgaaga gggatctgag ttaacattaa acatttttt   13620 ctttgcacag ggtggtgaag ctgctatgac agacttcaat tattatcgct acaatagagt   13680
cacagtactt gatatttgcc aagctcaatt tgtttacaaa atagttggca gtattttga   13740 atgttatgac ggtgggtgca ttaatgctcg tgaagttgtt gttacaaact atgacaagag   13800
tgctggctat cctttgaaca aatttggtaa agctagactt tactacgaaa ctctttcata   13860
tgaagagcag gatgcacttt ttgctttaac aaagagaaat gttttaccca caatgactca   13920
aatgaatttg aaatacgcta tttctggtaa ggcaagagct cgtacagtag gaggagtttc   13980 acttcttct accatgacta cgagacaata tcatcagaag catttgaagt caattgctgc   14040
aacacgcaat gctactgtgg tcattggttc aaccaagttt tatggtggtt gggacaatat   14100
gcttaaaaat ttaatgcgtg atgttgataa tggttgtttg atgggatggg actatcctaa   14160
gtgtgaccgt gctttaccta atatgattag aatggcttct gccatgatat taggttctaa   14220
gcatgttggt tgttgtacac ataatgatag gttctaccgc ctctccaatg agttagctca   14280
agtactcaca gaagttgtgc attgcacagg tggtttttat tttaaacctg gtggtacaac   14340
tagcggtgat ggtactacag catatgctaa ctctgcttt aacatctttc aagctgtttc   14400
tgctaatgtt aataagcttt gggggttga ttcaaacgct tgtaacaacg ttacagtaaa   14460
atccatacaa cgtaaaattt acgataattg ttatcgtagt agcagcattg atgaagaatt   14520
tgttgttgag tactttagtt atttgagaaa acactttct atgatgattt tatctgatga   14580
tggagttgtg tgctacaaca agattatgc ggatttaggt tatgtagctg acattaatgc   14640
ttttaaagca acactttatt accagaataa cgtctttatg tccacttcta agtgttgggt   14700
agaaccagat cttagtgttg gaccacatga atttgttca cagcatacat gcagattgt   14760 tgggcctgat ggagactact atcttcccta tccagacccg tccagaattt tatcagctgg   14820
tgtgtttgtt gatgacatag ttaaaacaga caatgttatt atgttagaac gttacgtgtc   14880
attggctatt gacgcatacc cgctcacaaa acaccctaag cctgcttatc aaaaagtgtt   14940
ttacactcta ctagattggg ttaaacatct acagaaaaat ttgaatgcag gttcttga   15000 ttcgttttca gtgacaatgt tagaggaagg tcaagataag ttctggagtg aagagtttta   15060
cgctagcctc tatgaaaagt ccactgtctt gcaagctgca ggcatgtgtg tagtatgtgg   15120
ttcgcaaact gtacttcgtt gtggagactg tcttaggaga ccacttttat gcacgaaatg   15180
tgcttacgac catgttatgg aacaaagca taaattcatt atgtctatca caccatatgt   15240
gtgtagtttt aatggttgta atgtcaatga tgttacaaag ttgtttttag gtggtcttag   15300
ttattattgt atgaaccaca aaccacagtt gtcattccca ctctgtgcta atggcaacgt   15360
ttttggtcta tataaaagta gtgcagtcgg ctcagaggct gttgaagatt caacaaact   15420
```

```
tgcagtttct gactggacta atgtagaaga ctacaaactt gctaacaatg tcaaggaatc    15480
tctgaaaatt ttcgctgctg aaactgtgaa agctaaggag gagtctgtta aatctgaata    15540
tgcttatgct gtattaaagg aggttatcgg ccctaaggaa attgtactcc aatgggaagc    15600
ttctaagact aagcctccac ttaacagaaa ttcagttttc acgtgttttc agataagtaa    15660
ggatactaaa attcaattag gtgaatttgt gtttgagcaa tctgagtacg gtagtgattc    15720
tgtttattac aagagcacga gtacttacaa attgacacca ggtatgattt ttgtgttgac    15780
ttctcataat gtgagtcctc ttaaagctcc aatttttagtc aaccaagaaa agtacaatac    15840
catatctaag ctctatcctg tctttaatat agcggaggcc tataatacac tggttcctta    15900
ctaccaaatg ataggtaagc aaaaatttac aactatccaa ggtcctcctg gtagcggtaa    15960
atctcattgt gttataggtt tgggtttgta ttaccctcag gcgagaatag tctacactgc    16020
atgttctcat gcggctgtag acgctttatg tgaaaaagca gccaaaaact tcaatgttga    16080
tagatgttca aggataatac ctcaaagaat cagagttgat tgttacacag ctttaagcc    16140 taataacacc aatgcgcagt acttgttttg tactgttaat gctctaccag aagcaagttg    16200
tgacattgtt gtagttgatg aggtctctat gtgtactaat tatgatctta gtgtcataaa    16260
tagccgactg agttacaaac atattgttta tgttggagac ccacagcagc taccagctcc    16320
tagaactttg attaataagg gtgtacttca accgcaggat tacaatgttg taaccaaaag    16380
aatgtgcaca ctaggacctg atgtcttttt gcataaatgt tacaggtgcc cagctgaaat    16440
tgttaagaca gtctctgcac ttgttttatga aaataaattt gtacctgtca acccagaatc    16500
aaagcagtgc ttcaaaatgt tgtaaaagg tcaggttcag attgagtcta actcttctat    16560
aaacaacaag caactagagg ttgtcaaggc ctttttagca cataatccaa aatggcgtaa    16620
agctgttttc atctcacccct ataatagtca aaattatgtt gctcggcgtc ttcttggttt    16680
gcaaacgcaa actgtggatt ccgctcaggg tagtgagtat gattacgtca tctacacaca    16740
gacctccgat acacagcatg ctactaatgt taacagattt aatgttgcca ttacgagagc    16800
aaaggttggt atactttgta tcatgtgtga tagaactatg tatgagaatc ttgatttcta    16860
tgaactcaaa gattcaaaga ttggtttaca agcaaaacct gaaacttgtg gtttatttaa    16920
agattgttcg aagagcgaac aatacatacc acctgcttat gcaacgacat atatgagctt    16980
atctgataat tttaagacaa gtgatggttt agctgttaac atcggtacaa aagatgttaa    17040
atatgctaat gtcatctcat atatgggatt caggtttgaa gccaacatac caggctatca    17100
cacactattc tgcacgcgag attttgctat gcgtaatgtt agagcatggc ttgggtttga    17160
cgttgaaggt gcacatgtct gtggtgataa tgttggaact aatgtaccat tacagctggg    17220
tttctcaaac ggtgtggatt ttgtagtgca aactgaagga tgtgttatta ctgaaaaagg    17280
taatagcatt gaggttgtaa aagcacgagc accaccaggt gagcaatttg cacacttgat    17340
tccgcttatg agaaagggtc aaccttggca cattgttaga cgccgtatag tgcagatggt    17400
ctgtgactat tttgatggct tatcagacat tctgatcttt gtgctttggg ctggtggtct    17460
tgaacttaca actatgagat actttgttaa aattggaaga ccacaaaaat gtgaatgcgg    17520
caaaagtgca acttgttata gtagctctca atctgtttat gcttgcttca gcatgcatt    17580 aggatgtgat tatttatata accttactg cattgacata cagcaatggg gttacacagg    17640
atctttgagc atgaatcatc atgaagtttg caacattcat agaaatgagc atgtagctag    17700
tggtgatgct atcatgacta gatgtctcgc tatacatgac tgtttttgtca aacgtgttga    17760 ttggtcaatt gtgtaccctt ttattgacaa tgaagaaaag atcaataaag ctggtcgcat    17820
```

```
agtgcagtca catgtcatga aagctgctct gaagattttt aatcctgctg caattcacga   17880
tgtgggtaat ccaaaaggca tccgttgtgc tacaacacca ataccatggt tttgttatga   17940
tcgtgatcct attaataaca atgttagatg tctggattat gactatatgg tacatggtca   18000
aatgaatggt cttatgttat tttggaactg taatgtagac atgtacccag agttttcaat   18060
tgtttgtaga tttgatactc gcactcgctc taaattgtct ttagaaggtt gtaatggtgg   18120
tgcattgtat gttaataacc atgctttcca cacaccagct tatgatagaa gagcttttgc   18180
taagcttaaa cctatgccat tcttttacta tgatgatagt aattgtgaac ttgttgatga   18240
gcaacctaat tatgtaccac ttaagtcaaa tgtttgcata acaaaatgca acattggtgg   18300
tgctgtctgc aagaagcatg ctgctcttta cagagcgtat gttgaggatt acaacatttt   18360
tatgcaggct ggttttacaa tatggtgtcc tcaaaacttt gacacctata tgctttggca   18420
tggttttgtt aatagcaaag cacttcagag tctagaaaat gtggctttta atatcgttaa   18480
gaaaggtgcc ttcaccggtt taaaaggtga cttaccaact gctgttattg ctgacaaaat   18540
aatggtaaga gatggaccta ctgacaaatg tattttttaca aataagacta gtttacctac   18600
aaatgtagct tttgagttat atgcaaaacg caaacttgga ctcacacctc cattaacaat   18660
acttaggaat ttaggtgttg tcgcaacata taagtttgtg ttgtgggatt atgaagctga   18720 acgtccttc tcaaatttca ctaagcaagt gtgttcctac actgatcttg atagtgaagt   18780
tgtaacatgt tttgataata gtattgctgg ttcttttgag cgttttacta ctacaagaga   18840
tgcagtgctt atttctaata acgctgtgaa agggcttagt gccattaaat tacaatatgg   18900
ccttttgaat gatctacctg taagtactgt tggaaataaa cctgtcacat ggtatatcta   18960
tgtgcgcaag aatggtgagt acgtcgaaca aatcgatagt tactatacac agggacgtac   19020
ttttgaaacc ttcaaaccct cgtagtacaat ggaagaagat tttcttagta tggatactac   19080
actcttcatc caaaagtatg gtcttgagga ttatggtttt gaacacgttg tatttggaga   19140
tgtctctaaa actaccattg gtggtatgca tcttcttata tcgcaagtgc gccttgcaaa   19200
aatgggtttg ttttccgttc aagaatttat gaataattct gacagtacac tgaaaagttg   19260
ttgtattaca tatgctgatg atccatcttc taagaatgtg tgcacttata tggacatact   19320
cttggacgat tttgtgacta tcattaagag cttagatctt aatgttgtgt ccaaagttgt   19380
ggatgtcatt gtagattgta aggcatggag atggatgttg tggtgtgaga attcacatat   19440
taaaaccttc tatccacaac tccaatctgc tgaatggaat cccggctata gcatgcctac   19500
actgtacaaa atccagcgta tgtgtctcga acggtgtaat ctctacaatt atggtgcaca   19560
agtgaaatta cctgtaggca ttactactaa gttcgttaag tatactcagt gtgtcaata   19620 ccttaacact actacattgt gtgtaccaca caaaatgcgt gtattgcatt taggagctgc   19680
tggtgcatct ggtgttgctc ctggtagtac tgtattaaga agatggttac cagatgatgc   19740
catattggtt gataatgatt tgagagatta cgtttccgac gcagacttca gtgttacagg   19800
tgattgtact agtctttaca tcgaagacaa gtttgatttg ctcgtctctg atttatatga   19860
tggctccaca aaatcaattg acggtgaaaa cacgtcgaaa gatggtttct ttacttatat   19920
taatggtttc attaaagaga aactgtcact tggtggatct gttgccatta aaatcacgga   19980
atttagttgg aataaagatt tatatgaatt gattcaaaga tttgagtatt ggactgtgtt   20040
ttgtacaagt gttaacacgt catcatcaga aggcttctg attggtatta actacttagg   20100
accatactgt gacaaagcaa tagtagatgg aaatataatg catgccaatt atatatttg   20160
```

-continued

```
gagaaactct acaattatgg ctctatcaca taactcagtc ctagacactc ctaaattcaa    20220
gtgtcgttgt aacaacgcac ttattgttaa tttaaaagaa aaagaattga atgaaatggt    20280
cattggatta ctaaggaagg gtaagttgct cattagaaat aatggtaagt tactaaactt    20340
tggtaaccac ttcgttaaca caccatgaaa aaactatttg tggttttggt cgtaatgcca    20400
ttgatttatg gagacaattt tccttgttct aaattgacta atagaactat aggcaaccag    20460
tggaatctca ttgaaacctt ccttctaaac tatagtagta ggttaccacc taattcagat    20520
gtggtgttag gtgattattt tcctactgta caaccttggt ttaattgcat tcgcaatgat    20580
agtaatgacc tttatgttac actggaaaat cttaaagcat tgtattggga ttatgctaca    20640
gaaaatatca cttggaatca cagacaacgg ttaaacgtag tcgttaatgg atacccatac    20700
tccatcacag ttacaacaac ccgcaatttt aattctgctg aaggtgctat tatatgcatt    20760
tgtaagggct caccacctac taccaccaca gaatctagtt tgacttgcaa ttggggtagt    20820
gagtgcaggt taaccataaa gttccctata tgtccttcta attcagaggc aaattgtggt    20880
aatatgctgt atggcctaca atggtttgca gatgaggttg ttgcttattt acatggtgct    20940
agttaccgta ttagttttga aaatcaatgg tctggcactg tcacatttgg tgatatgcgt    21000
gcgacaacat tagaagtcgc tggcacgctt gtagaccttt ggtggtttaa tcctgtttat    21060
gatgtcagtt attatagggt taataataaa aatggtacta ccgtagtttc caattgcact    21120
gatcaatgtg ctagttatgt ggctaatgtt tttactacac agccaggagg ttttatacca    21180
tcagatttta gttttaataa ttggttcctt ctaactaata gctccacgtt ggttagtggt    21240
aaattagtta ccaaacagcc gttattagtt aattgcttat ggccagtccc tagctttgaa    21300
gaagcagctt ctcatttttg ttttgagggt gctggctttg atcaatgtaa tggtgctgtt    21360
ttaaataata ctgtagacgt cattaggttc aaccttaatt ttactacaaa tgtacaatca    21420
ggtaagggtg ccacagtgtt ttcattgaac acaacgggtg gtgtcactct tgaaatttca    21480
tgttatacag tgagtgactc gagcttttc agttacggtg aaattccgtt cggcgtaact    21540
gatggaccac ggtactgtta cgtacactat aatggcacag ctcttaagta tttaggaaca    21600
ttaccaccta gtgtcaagga gattgctatt agtaagtggg gccattttta tattaatggt    21660
tacaatttct ttagcacatt tcctattgat tgtatatctt ttaatttgac cactggtgat    21720
agtgacgttt tctggacaat agcttacaca tcgtacactg aagcattagt acaagttgaa    21780
aacacagcta ttacaaaggt gacgtattgt aatagtcacg ttaataacat taaatgctct    21840
caaattactg ctaatttgaa taatggattt tatcctgttt cttcaagtga agttggtctt    21900
gtcaataaga gtgttgtgtt actacctagc ttttacacac ataccattgt taacataact    21960
attggtcttg gtatgaagcg tagtggttat ggtcaaccca tagcctcaac attaagtaac    22020
atcacactac caatgcagga tcacaacacc gatgtgtact gtattcgttc tgaccaattt    22080
tcagtttatg ttcattctac ttgcaaaagt gctttatggg acaatatttt taagcgaaac    22140
tgcacggacg ttttagatgc cacagctgtt ataaaaactg gtacttgtcc tttctcattt    22200
gataaattga caattactt aactttaac aagttctgtt tgtcgttgag tcctgttggt    22260
gctaattgta gtttgatgt agctgcccgt acaagaacca atgagcaggt tgttagaagt    22320
ttgtatgtaa tatgaaga aggagacaac atagtgggtg taccgtctga taatagtggt    22380
gtgcacgatt tgtcagtgct acacctagat tcctgcacag attacaatat atatggtaga    22440
actggtgttg gtattattag acaaaactaac aggacgctac ttagtggctt atattacaca    22500
tcactatcag gtgatttgtt aggttttaaa aatgttagtg atggtgtcat ctactctgta    22560
```

```
acgccatgtg atgtaagcgc acaagcagct gttattgatg gtaccatagt tggggctatc   22620
acttccatta acagtgaact gttaggtcta acacattgga caacaacacc taatttttat   22680
tactactcta tatataatta cacaaatgat aggactcgtg gcactgcaat tgacagtaat   22740
gatgttgatt gtgaacctgt cataacctat tctaacatag gtgtttgtaa aaatggtgct   22800
tttgttttta ttaacgtcac acattctgat ggagacgtgc aaccaattag cactggtaat   22860
gtcacgatac ctacaaactt taccatatcc gtgcaagtcg aatatattca ggtttacact   22920
acaccagtgt caatagactg ttcaagatat gttttgtaatg gtaaccctag gtgtaacaaa   22980
ttgttaacac aatacgtttc tgcatgtcaa actattgagc aagcacttgc aatgggtgcc   23040
agacttgaaa acatggaggt tgattccatg ttgtttgttt ctgaaaatgc ccttaaattg   23100
gcatctgttg aagcattcaa tagttcagaa actttagacc ctatttacaa agaatggcct   23160
aatataggtg gttcttggct agaaggtcta aaatacatac ttccgtccca taatagcaaa   23220
cgtaagtatc gttcagctat agaggacttg cttttttgata aggttgtaac atctggttta   23280
ggtacagttg atgaagatta taacgttgt acaggtggtt atgacatagc tgacttagta   23340
tgtgctcaat actataatgg catcatggtg ctacctggtg tggctaatgc tgacaaaatg   23400
actatgtaca cagcatccct tgcaggtggt ataacattag gtgcacttgg tggaggcgcc   23460
gtggctatac cttttgcagt agcagttcag gctagactta attatgttgc tctacaaact   23520
gatgtattga acaaaaacca gcagattctg ctagtgcttt caatcaagc tattggtaac   23580 attacacagt catttggtaa ggttaatgat gctatacatc aaacatcacg aggtcttgct   23640
actgttgcta aagcattggc aaaagtgcaa gatgttgtca acatacaagg gcaagcttta   23700
agccacctaa cagtacaatt gcaaaataat ttccaagcca ttagtagttc tattagtgac   23760
atttataata ggcttgacga attgagtgct gatgcacaag ttgacaggct gatcacagga   23820
agacttacag cacttaatgc atttgtgtct cagactctaa ccagacaagc ggaggttagg   23880
gctagtagac aacttgccaa agacaaggtt aatgaatgcg ttaggtctca gtctcagaga   23940
ttcggattct gtggtaatgg tacacatttg ttttcactcg caaatgcagc accaaatggc   24000
atgattttct ttcacacagt gctattacca acggcttatg aaactgtgac tgcttggcca   24060
ggtatttgtg cttcagatgg tgatcgcact tttggacttg tcgttaaaga tgtccagttg   24120
actttgtttc gtaatctaga tgacaagttc tatttgaccc ccagaactat gtatcagcct   24180
agagttgcaa ctagttctga ctttgttcaa attgaagggt gcgatgtgct gtttgttaat   24240
gcaactgtaa gtgatttgcc tagtattata cctgattata ttgatattaa tcagactgtt   24300
caagacatat tagaaaattt tagaccaaat tggactgtac ctgagttgac atttgacatt   24360
tttaacgcaa cctatttaaa cctgactggt gaaattgatg acttagaatt taggtcagaa   24420
aagctacata acaccactgt agaacttgcc attctcattg acaacattaa caatacatta   24480
gtcaatcttg aatggctcaa tagaattgaa acctatgtaa aatggccttg gtatgtgtgg   24540
ctactaatag gcttagtagt aatattttgc ataccattac tgctattttg ctgttgtagt   24600
acaggttgct gtggatgcat aggttgttta ggaagttgtt gtcactctat atgtagtaga   24660
agacaatttg aaaattacga accaattgaa aaagtgcacg tccattaaat ttaaaatgtt   24720
aattctatca tctgctataa tagcagttgt ttctgctaga gaattttgtt aaggatgatg   24780
aataaagtct ttaagaacta aacttacgag tcattacagg tcctgtatgg acattgtcaa   24840
atccatttac acatccgtag atgctgtact tgacgaactt gattgtgcat actttgctgt   24900
```

```
aactcttaaa gtagaattta agactggtaa attacttgtg tgtataggtt ttggtgacac    24960
acttcttgct gctaaggata aagcatatgc taagcttggt ctctccatta ttgaagaagt    25020
caatagtcat atagttgttt aatatcatta aacacacaaa acccaaagca ttaagtgtta    25080
caaaacaatt aaagagagat tatagaaaaa ctgtcattct aaattccatg cgaaaatgat    25140
tggtggactt tttcttagta ctctgagttt tgtaattgtt agtaaccatt ctattgttaa    25200
taacacagca aatgtgcatc atatacaaca agaacgtgtt atagtacaac agcatcatgt    25260
tgttagtgct agaacacaaa actattaccc agagttcagc atcgctgtac tctttgtatc    25320
ttttctagct ttgtaccgta gtacaaactt taagacgtgt gtcggcatct taatgtttaa    25380
gattttatca atgacacttt taggacctat gcttatagca tatggttact acattgatgg    25440
cattgttaca acaactgtct tatctttaag atttgtctac ttagcatact tttggtatgt    25500
taatagtagg tttgaattta ttttatacaa tacaacgaca ctcatgtttg tacatggcag    25560
agctgcaccg tttatgagaa gttctcacag ctctatttat gtcacattgt atggtggcat    25620
aaattatatg tttgtgaatg acctcacgtt gcattttgta daccctatgc ttgtaagcat    25680
agcaatacgt ggcttagctc atgctgatct aactgtagtt agagcagttg aacttctcaa    25740
tggtgatttt atttatgtat tttcacagga gcccgtagtc ggtgtttaca atgcagcctt    25800
ttctcaggcg gttctaaacg aaattgactt aaaagaagaa gaagaagacc atacctatga    25860
cgtttcctag ggcattgact gtcatagatg acaatggaat ggtcattaac atcatttct    25920
ggttcctgtt gataattata ttgatattac tttcaatagc attgctaaat ataattaagc    25980
tatgcatggt gtgttgcaat ttaggaagga cagttattat tgttccagcg caacatgctt    26040
acgatgccta taagaatttt atgcgaatta aagcatacaa ccccgatgga gcactccttg    26100
cttgaactaa acaaaatgaa gattttgtta atattagcgt gtgtgattgc atgcgcatgt    26160
ggagaacgct attgtgctat gaaatccgat acagatttgt catgtcgcaa tagtacagcg    26220
tctgattgtg agtcatgctt caacggaggc gatcttattt ggcatcttgc aaactggaac    26280
ttcagctggt ctataatatt gatcgttttt ataactgtgc tacaatatgg aagacctcaa    26340
ttcagctggt tcgtgtatgg cattaaaatg cttataatgt ggctattatg gcccgttgtt    26400
ttggctctta cgattttaa tgcatactcg gaataccaag tgtccagata tgtaatgttc    26460
ggctttagta ttgcaggtgc aattgttaca tttgtactct ggattatgta ttttgtaaga    26520
tccattcagt tgtacagaag gactaagtct tggtggtctt tcaaccctga actaaagca    26580
attctttgcg ttagtgcatt aggaagaagc tatgtgcttc ctctcgaagg tgtgccaact    26640
ggtgtcactc taactttgct ttcagggaat ttgtacgctg aagggttcaa aattgcaggt    26700
ggtatgaaca tcgacaattt accaaaatac gtaatggttg cattacctag caggactatt    26760
gtctacacac ttgttggcaa gaagttgaaa gcaagtagtg cgactggatg ggcttactat    26820
gtaaaatcta aagctggtga ttactcaaca gaggcaagaa ctgataattt gagtgagcaa    26880
gaaaaattat tacatatggt ataactaaac ttctaaatgg ccaaccaggg acaacgtgtc    26940
agttggggag atgaatctac caaaacacgt ggtcgttcca attcccgtgg tcggaagaat    27000
aataacatac ctctttcatt cttcaacccc ataaccctcc aacaaggttc aaaattttgg    27060
aacttatgtc cgagagactt tgtacccaaa ggaataggta acagggatca acagattggt    27120
tattggaata gacaaactcg ctatcgcatg gtgaagggcc aacgtaaaga gcttcctgaa    27180
aggtggttct tctactactt aggtactgga cctcatgcag atgccaaatt taaagataaa    27240
ttagatggag ttgtctgggt tgccaaggat ggtgccatga acaaaccaac cacgcttggt    27300
```

-continued

```
agtcgtggtg ctaataatga atccaaagct ttgaaattcg atggtaaagt gccaggcgaa    27360
tttcaacttg aagttaatca atcaagagac aattcaaggt cacgctctca atctagatct    27420
cggtctagaa atagatctca atctagaggc aggcaacaat tcaataacaa gaaggatgac    27480
agtgtagaac aagctgttct tgccgcactt aaaaagttag gtgttgacac agaaaaacaa    27540
cagcaacgct ctcgttctaa atctaaagaa cgtagtaact ctaagacaag agatactaca    27600
cctaagaatg aaaacaaaca cacctggaag agaactgcag gtaaaggtga tgtgacaaga    27660
ttttatggag ctagaagcag ttcagccaat tttggtgaca ctgacctcgt tgccaatggg    27720
agcagtgcca agcattaccc acaactggct gaatgtgttc catctgtgtc tagcattctg    27780
tttggaagct attggacttc aaaggaagat ggcgaccaga tagaagtcac gttcacacac    27840
aaataccact tgccaaagga tgatcctaag actggacaat tccttcagca gattaatgcc    27900
tatgctcgtc catcagaagt ggcaaaagaa cagagaaaaa gaaatctcg ttctaaatct    27960 gcagaaaggt cagagcaaga tgtggtacct gatgcattaa tagaaaatta tacagatgtg    28020
tttgatgaca cacaggttga gataattgat gaggtaacga actaaacgag atgctcgtct    28080
tcctccatgc tgtatttatt acagttttaa tcttactact aattggtaga ctccaattat    28140
tagaaagact attacttaat cactctttca atcttaaaac tgtcaatgac tttaatatct    28200
tatataggag tttagcagaa accagattac taaaagtggt gcttcgagta atctttctag    28260
tcttactagg attttgctgc tacagattgt tagtcacatt aatgtaaggc aacccgatgt    28320
ctaaaactgg ttttccgag gaattactgg tcatcgcgct gtctactctt gtacagaatg    28380
gtaagcacgt gtaataggag gtacaagcaa ccctattgca tattaggaag tttagatttg    28440
atttggcaat gctagattta gtaatttaga gaagtttaaa gatccgctac gacgagccaa    28500
caatggaaga gctaacgtct ggatctagtg attgtttaaa atgtaaaatt gtttgaaaat    28560
tttccttttg atagtgatac aaaaaaaa                                      28588
```

```
<210> SEQ ID NO 2
<211> LENGTH: 21
<212> TYPE: DNA
<213> ORGANISM: Porcine Transmissible Gastroenteritis V

<400> SEQUENCE: 2
cctaggattt aaatcctaag g                                             21

<210> SEQ ID NO 3
<211> LENGTH: 27
<212> TYPE: DNA
<213> ORGANISM: Porcine Transmissible Gastroenteritis V

<400> SEQUENCE: 3
gcggccgcgc cggcgaggcc tgtcgac                                       27

<210> SEQ ID NO 4
<211> LENGTH: 6
<212> TYPE: DNA
<213> ORGANISM: Porcine Transmissible Gastroenteritis V

<400> SEQUENCE: 4 gtcgac                                                              6

<210> SEQ ID NO 5
<211> LENGTH: 22
<212> TYPE: DNA
```

<213> ORGANISM: Porcine Transmissible Gastroenteritis V
<300> PUBLICATION INFORMATION:

<400> SEQUENCE: 5
gctagcccag gcgcgcggta cc    22

<210> SEQ ID NO 6
<211> LENGTH: 11
<212> TYPE: DNA
<213> ORGANISM: Porcine Transmissible Gastroenteritis V

<400> SEQUENCE: 6
ctatggtata a    11

<210> SEQ ID NO 7
<211> LENGTH: 11
<212> TYPE: DNA
<213> ORGANISM: Porcine Transmissible Gastroenteritis V

<400> SEQUENCE: 7
aatgtaagtt a    11

<210> SEQ ID NO 8
<211> LENGTH: 11
<212> TYPE: DNA
<213> ORGANISM: Porcine Transmissible Gastroenteritis V

<400> SEQUENCE: 8
atttgcttga a    11

<210> SEQ ID NO 9
<211> LENGTH: 11
<212> TYPE: DNA
<213> ORGANISM: Porcine Transmissible Gastroenteritis V

<400> SEQUENCE: 9
ctatggtata a    11

<210> SEQ ID NO 10
<211> LENGTH: 25
<212> TYPE: DNA
<213> ORGANISM: Porcine Transmissible Gastroenteritis V

<400> SEQUENCE: 10
tttggtaaca cttcgttaac acacc    25

<210> SEQ ID NO 11
<211> LENGTH: 23
<212> TYPE: DNA
<213> ORGANISM: Porcine Transmissible Gastroenteritis V

<400> SEQUENCE: 11
ttacgagtca ttacaggtcc tgt    23

<210> SEQ ID NO 12
<211> LENGTH: 24
<212> TYPE: DNA
<213> ORGANISM: Porcine Transmissible Gastroenteritis V

<400> SEQUENCE: 12
tttaagacgt gtgtcggcat ctta    24

<210> SEQ ID NO 13

-continued

```
<211> LENGTH: 37
<212> TYPE: DNA
<213> ORGANISM: Porcine Transmissible Gastroenteritis V

<400> SEQUENCE: 13
gaaattgact taaaagaaga agaagaagac catacct                              37

<210> SEQ ID NO 14
<211> LENGTH: 10
<212> TYPE: DNA
<213> ORGANISM: Porcine Transmissible Gastroenteritis V

<400> SEQUENCE: 14
gtcgacgacc                                                            10

<210> SEQ ID NO 15
<211> LENGTH: 12
<212> TYPE: DNA
<213> ORGANISM: Porcine Transmissible Gastroenteritis V

<400> SEQUENCE: 15
gaaatatttg tc                                                         12
```

US 7,445,928 B2

BACTERIAL ARTIFICIAL CHROMOSOME CONSTRUCT ENCODING RECOMBINANT CORONAVIRUS

This application is a national stage entry filed under 35 U.S.C. 371 of PCT/EP00/12063, filed Nov. 30, 2000.

FIELD OF THE INVENTION

This invention relates to methods of preparing a DNA or an RNA, nucleic acids obtainable by this method and their use as vaccines and for gene therapy.

BACKGROUND OF THE INVENTION

Advances in recombinant DNA technology have led to progress in the development of gene transfer between organisms. At this time, numerous efforts are being made to produce chemical, pharmaceutical, and biological products of economic and commercial interest through the use of gene transfer techniques.

One of the key elements in genetic manipulation of both prokaryotic and eukaryotic cells is the development of vectors and vector-host systems. In general, a vector is a nucleic acid molecule capable of replicating or expressing in a host cell. A vector-host system can be defined as a host cell that bears a vector and allows the genetic information it contains to be replicated and expressed.

Vectors have been developed from viruses with both DNA and RNA genomes. Viral vectors derived from DNA viruses that replicate in the nucleus of the host cell have the drawback of being able to integrate into the genome of said cell, so they are generally not very safe. In contrast, viral vectors derived from RNA viruses, which replicate in the cytoplasm of the host cell, are safer than those based on DNA viruses, since the replication occurs through RNA outside the nucleus. These vectors are thus very unlikely to integrate into the host cell's genome.

cDNA clones have been obtained from single-chain RNA viruses with positive-polarity [ssRNA(+)], for example, picornavirus (Racaniello & Baltimore, 1981); bromovirus (Ahlquist et al., 1984); alphavirus, a genus that includes the Sindbis virus; Semliki Forest virus (SFV) and the Venezuelan equine encephalitis virus (VEE) (Rice et al., 1987; Liljeström and Garoff, 1991; Frolov et al., 1996; Smerdou and Liljestrom, 1999); flavivirus and pestivirus (Rice and Strauss, 1981; Lai et al., 1991; Rice et al., 1989); and viruses of the Astroviridae family (Geigen-muller et al., 1997). Likewise, vectors for the expression of heterologous genes have been developed from clones of DNA complementary to the genome of ssRNA(+) virus, for example alphavirus, including the Sindbis virus, Semliki Forest virus (SFV), and the Venezuelan equine encephalitis (VEE) virus (Frolov et al., 1996; Liljeström, 1994; Pushko et al., 1997). However, all methods of preparing recombinant viruses starting from RNA viruses are still complicated by the fact that most of the viruses comprise sequences which are toxic for bacteria. Preparing a cDNA of the viral RNA and subcloning of the cDNA in bacteria therefore often leads to deletion or rearrangement of the DNA sequences in the bacterial host. For this purpose most of the commonly used subcloning and expression vectors cannot be used for preparation of large DNA sections derived from recombinant RNA viruses. However, obtaining vectors, which can carry long foreign DNA sequences is required for a number of aspects in the development of pharmaceuticals, specifically vaccines.

The coronaviruses are ssRNA(+) viruses that present the largest known genome for an RNA virus, with a length comprised between about 25 and 31 kilobases (kb) (Siddell, 1995; Lai & Cavanagh, 1997; Enjuanes et al., 1998). During infection by coronavirus, the genomic RNA (gRNA) replicates and a set of subgenomic RNAs (sgRNA) of positive and negative polarity is synthesized (Sethna et al., 1989; Sawicki and Sawicki, 1990; van der Most & Spaan, 1995). The synthesis of the sgRNAs is an RNA-dependent process that occurs in the cytoplasm of the infected cell, although its precise mechanism is still not exactly known.

The construction of cDNAs that code defective interfering (DI) genomes (deletion mutants that require the presence of a complementing virus for their replication and transcription) of some coronaviruses, such as the murine hepatitis virus (MHV), infectious bronchitis virus (IBV), bovine coronavirus (BCV) (Chang et al., 1994), and porcine gastroenteritis virus (TGEV) (Spanish Patent Application P9600620; Méndez et al., 1996; Izeta et al., 1999; Sánchez et al., 1999) has been described. However, the construction of a cDNA clone that codes a complete genome of a coronavirus has not been possible due to the large size of and the toxic sequences within the coronavirus genome.

In summary, although a large number of viral vectors have been developed to replicate and express heterologous nucleic acids in host cells, the majority of the known vectors for expression of heterologous genes are not well suited for subcloning of RNA viruses. Further, the viral vectors so obtained present drawbacks due to lack of species specificity and target organ or tissue limitation and to their limited capacity for cloning, which restricts the possibilities of use in both basic and applied research.

Hence there is a need for methods to develop new vectors for expression of heterologous genes that can overcome the aforesaid problems. In particular, it would be advantagous to have large vectors for expression of heterologous genes with a high level of safety and cloning capacity, which can be designed so that their species specificity and tropism can be controlled.

SUMMARY OF THE INVENTION

According to the present invention the above problems are solved by a method of preparing a DNA comprising steps, wherein
(a) a DNA comprising a full length copy of the genomic RNA (gRNA) of an RNA virus; or
(b) a DNA comprising one or several fragments of a gRNA of an RNA virus, which fragments code for an RNA dependent RNA polymerase and at least one structural or non-structural protein; or
(c) a DNA having a homology of at least 60% to the sequences of (a) or (b); is cloned into a bacterial artificial chromosome (BAC).

Surprisingly, the present inventors found that the problems encountered by the prior art methods to subclone and express large DNA sequences derived from viral gRNA can be overcome by using BACs as a cloning vector. The use of BACs has the particular advantage that these vectors are present in bacteria in a number of one or two copies per cell, which considerably limits the toxicity and reduces the possibilities of interplasmid recombinantion.

The invention further provides methods of preparing a viral RNA or a virion comprising steps, wherein a DNA is prepared according to one of the above methods, the DNA is expressed and the viral RNA or the virion is isolated. Further, methods of preparing pharmaceuticals, specifically vaccines comprising the steps of the above methods to prepare a DNA are disclosed.

According to another aspect of the present invention provides a DNA comprising sequences derived from the genomic RNA (gRNA) of a coronavirus which sequences have a homology of at least 60% to the natural sequence of the coronavirus and code for an RNA dependent RNA polymerase and at least one structural or non-structural protein, wherein a fragment of said DNA is capable of being transcribed into RNA and which RNA can be assembled to a virion. The present invention also encompasses methods of preparing respective DNAs.

The present invention further provides vectors, more specifically bacterial artificial chromosomes (BACs) comprising respective nucleic acids. According to a further embodiment the present invention is directed to host cells and infectious, attenuated or inactivated viruses comprising the DNAs or RNAs of the present invention.

The invention also provides pharmaceutical preparations, such as mono- or multivalent vaccines comprising nucleic acids, vectors, host cells or virions of the present invention.

Finally, the present invention provides methods for producing a virion or a viral RNA comprising steps, wherein a DNA according to the present invention is transcribed and the virions or viral RNAs are recovered, as well as viral RNAs obtainable by this method.

BRIEF DESCRIPTION OF THE FIGURES

FIG. 1 shows the construction of a cDNA clone that codes an infective RNA of TGEV.

FIG. 1A shows the genetic structure of the TGEV, with the names of the genes indicated by letters and numbers (1a, 1b, S, 3a, 3b, E, M, N, and 7).

FIG. 1B shows the cDNA-cloning strategy, which consisted in completing the DI-C genome. Deletions Δ1, Δ2, and Δ3 that have been completed to reestablish the full length of the cDNA are indicated. The numbers located beneath the structure of the DI-C genome indicate the nucleotides that flank each deletion in said DI-C genome.

FIG. 1C shows the four cDNA fragments constructed to complete deletion Δ1 and the position of the principal restriction sites used during joining. The insertion of fragment Δ1 produced an increase in the toxicity of the cDNA.

FIG. 6 shows the cytopathic effect (CPE) produced by the TGEV cDNA in the transfected ST cells. The absence of CPE in non-transfected (control) ST cells (FIG. 6A) and the CPE observed 14 and 20 h after transfection with pBAC-TcDNA$^{FL}$ in ST cells are shown (FIGS. 6B and 6C, respectively).

FIG. 9 shows the results of the RT-PCR analysis of the virus recovered. The viral RNA was expressed under the control of the CMV promoter recognized by the cellular polymerase pol II. In principle, this RNA could undergo splicing during its transport to the cytoplasm. To study whether this was the case, the sites of the RNA with a high probability of splicing were determined using a program for predicting splicing sites in sequences of human DNA (Version 2.1.5.94, Department of Cell Biology, Baylor College of Medicine) (Solovyev et al., 1994). The potential splicing site with maximum probability of cut had the donor site at nt 7,243 and the receiver at nt 7,570 (FIG. 9A). To study whether this domain had undergone splicing, a RT-PCR fragment flanked by nt 7,078 and nt 7,802 (FIG. 9B) was prepared from RNA of passages 0 and 2 of nontransfected cultures (control), or from ST cells transfected with TcDNA with the ClaI fragment in reverse orientation (TcDNA$^{FL(-\Delta ClaI)RS}$), or in the correct orientation (TcDNA$^{FL}$), and the products resulting from the RT-PCR were analyzed in agarose gels. The results obtained are shown in FIGS. 9C (passage 0) and 9D (passage 2).

FIG. 10 shows the results of the immunofluorescence analysis of the virus produced in cultures of ST cells transfected with TcDNA. Staining for immunofluorescence was done with antibodies specific for the TGEV PUR46-MAD isolate, and for the virus recovered after transfection with the pBAC-TcDNA$^{FL}$ plasmid. For this, TGEV-specific monoclonal antibodies were used which bind to both isolates or only to PUR46-MAD (Sánchez et al., 1990). The result confirmed that the TcDNA virus had the expected antigenicity. The specific polyclonal antiserum for TGEV bound to both viruses, but not to the uninfected cultures, and only the expected monoclonal antibodies specific for the S (ID.B12 and 6A.C3), M (3B.B3), and N (3B.D8) proteins bound to the TcDNA virus (Sánchez et al., 1999).

FIG. 11 (SEQ ID NOS: 10-15)shows the expression of GUS under different transcription-regulatory sequences (TRSs) that vary flanking region 5' of the intergenic (IG) sequence. Minigenome M39 was cloned under the control of the CMV promoter. ( FIG. 11A.) Inserted into this minigenome was a multiple cloning sequence (PL1, 5'-CCTAG-GATTTAA-ATCCTAAGG-3'; SEQ ID NO: 2) and the transcription unit formed by the selected transcription-regulating sequences (TRS), another multiple cloning sequence (PL2, 5'-GCGGCCGCGCCGGCGAGGCCTGTCGAC-3'; SEQ ID NO:3; or PL3, 5'-GTCGAC-3'; SEQ ID NO:4), sequences with the structure of a Kozak (Kz) domain, the β-glucuronidase (GUS) gene, and another multiple cloning site (PL4, 5'-GCTAGCCCAGGCGCGCGGTACC-3'; SEQ ID NO: 5). These sequences [1]were flanked at the 3'-end by the 3'-sequence of minigenome M39, the HDV ribozyme, and the termination and polyadenylation sequences of BGH. The TRSs had a different number (0, −3, −8, and −88) of nucleotides of the 5'-end of the IG sequence (CUAAAC)[1], and came from the N, S, or M genes, as indicated. ST cells were transfected with the different plasmids, were infected with the complementing virus (PUR46-MAD), and the supernatants were passed 6 times. The GUS activity in the infected cells was determined by means of the protocol described by Izeta (Izeta et al., 1999). The results obtained by relating the GUS activity to the passage number are collected in FIG. 11B.

Figure 2:
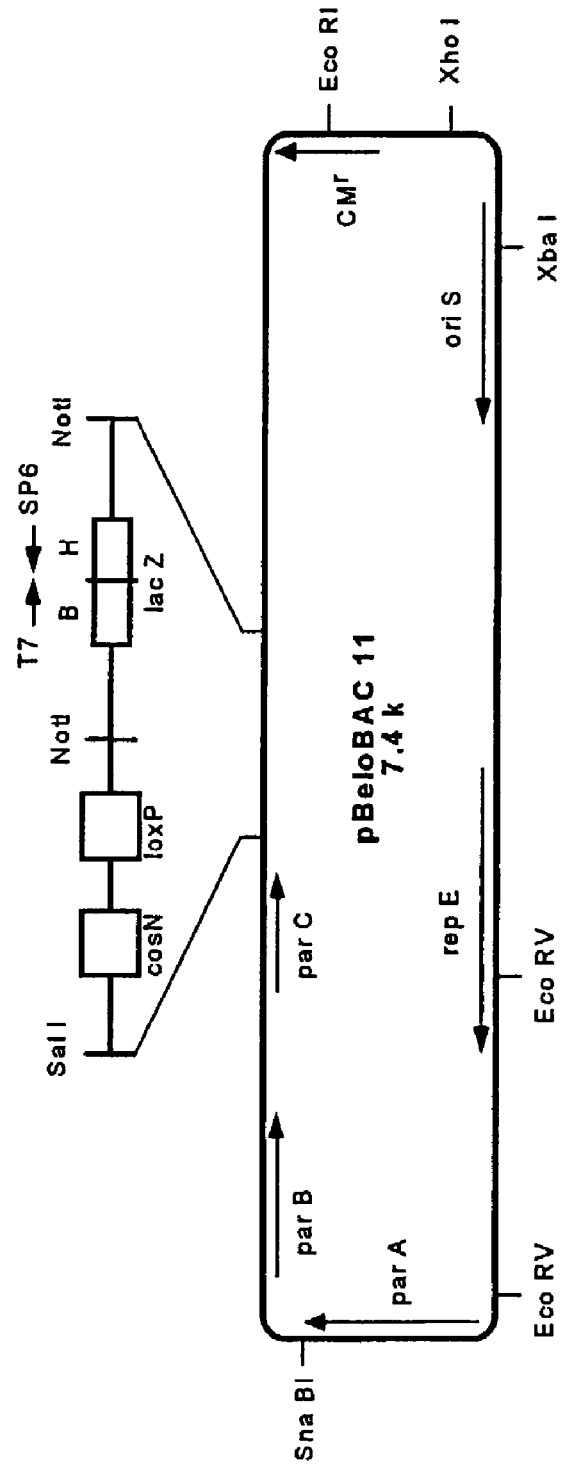
FIG. 2 shows the structure of the pBeloBAC plasmid (Wang et al., 1997) used in cloning the infective cDNA of TGEV. The pBeloBAC plasmid was provided by H. Shizuya and M. Simon (California Institute of Technology) and includes 7,507 base pairs (bp) that contain the replication origin of the F factor of *E. coli* (oriS), the genes necessary to keep one single copy of the plasmid per cell (parA, parB, parC, and repE), and the chloramphenicol-resistance gene (CM$^r$). The positions of the T7 and SP6 promoters and of the unique restriction sites are indicated. CosN: site cosN of lambda to facilitate the construction of the pBAC plasmid; lac Z: β-galactosidase gene. Sequence loxP used during the generation of the plasmid is also indicated.

[1] It should be noted that CTAAAC and CUAAC have the same meaning for the purpose of this patent. The first represents the sequence of the DNA and the second that of the corresponding RNA.

FIG. 12 (SEQ ID NOS: 16-24) shows the expression of GUS under different TRSs that vary in the 3'-flanking region of the IG sequence (see FIG. 11A). Using this transcription unit with the 5'-flanking region corresponding to the -88 nt of the N gene of TGEV plus the IG sequence (CUAAAC), the 3'-flanking sequences were modified. These sequences corresponded to those of the different TGEV genes (S, 3a, 3b, E, M, N, and 7), as is indicated in FIG. 12A. In two cases, 3'-sequences were replaced by others that contained a restriction site (SalI) and an optimized Kozak sequence (Kz), or by a sequence identical to the one that follows the first IG sequence located following the leader of the viral genome. The activity of GUS in the infected cells was determined by means of the protocol described above (Izeta et al., 1999). cL12 indicates a sequence of 12 nucleotides identical to that of 3'-end of the "leader" sequence of the TGEV genome (see the virus sequence indicated at the end). The results obtained by relating the expression of GUS to the passage number are collected in FIG. 12B.

FIG. 13 shows the effect of the site of insertion of the module of expression in the minigenome over the levels of GUS expression. The GUS transcription unit, containing −88 nt of the N gene flanking the 5'-end of the IG sequence (CUAAAC), and the Kz sequences flanking the 3'-end (see FIG. 12A), was inserted into four single restriction sites in minigenome M39 (FIG. 13A) to determine if all these sites were equally permissive for the expression of the heterologous gene. ST cells were transfected with these plasmids and infected with the complementing virus (PUR46-MAD). The GUS activity in the infected cells was determined at passage 0 (P0) following the protocol described above (Izeta et al., 1999). The results obtained are collected in FIG. 13B.

FIG. 14 (SEQ ID No: 1) shows the consent sequence of the PUR46-MAD isolate of TGEV.

DETAILED DESCRIPTION OF THE INVENTION

According to the present invention methods of preparing a DNA are provided, which comprise steps, wherein
 (a) a DNA comprising a full length copy of the genomic RNA (gRNA) of an RNA virus; or
 (b) a DNA comprising one or several fragments of a gRNA of an RNA virus, which fragments code for an RNA dependent RNA polymerase and at least one structural or non-structural protein; or
 (c) a DNA having a homology of at least 60% to the sequences of (a) or (b);

is cloned into a bacterial artificial chromosome (BAC).

According to the present application a "bacterial artificial chromosome" is a DNA sequence which comprises the sequence of the F factor. Plasmids containing this sequences, so-called F plasmids, are capable of stably maintaining heterologous sequences longer than 300 Kb in low copy number (one or two copies per cell). Respective BACs are known in the art (Shizuya et al., 1992).

According to the present invention the DNA cloned into the BAC has a homology of at least 60%, preferably 75% and more preferably 85 or 95%, to a natural sequence of an RNA virus. Sequence homology is preferably determined using the Clustal computer program available from the European Bioinformatics Institute (EBI).

According to the methods of the present invention the DNA cloned into the BAC may further comprise sequences coding for several or all except one of the structural or non-structural proteins of the virus.

In a preferred embodiment of the present invention the DNA cloned into the BAC further comprises sequences encoding one or several heterologous gene. According to the present application a gene is characterized as a "heterologous gene" if it is not derived from the virus which was used as a source for the genes encoding the RNA dependent RNA polymerase and the structural or non-structural protein. A "heterologous gene" thus also refers to genes derived from one type of virus and expressed in a vector comprising sequences derived from another type of virus. Any heterologous gene of interest can be inserted into the nucleic acids of the present invention. The insertion of genes encoding one or several peptides or proteins which are recognised as an antigen from an infectious agent by the immune system of a mammal is especially preferred. Alternatively, the method of the present invention may be performed using heterologous genes encoding at least one molecule interfering with the replication of an infectious agent or an antibody providing protection against an infectious agent. The heterologous sequences may contain sequences encoding an immune modulator, a cytokine, an immonenhancer and/or an anti-inflammatory compound.

The method of the present invention may be performed using a DNA for cloning into a BAC that has any size. However, specific advantages over the known methods to prepare subcloned DNA from viral are obtained, if large sequences are used. The DNA cloned into the BAC may thus comprise a length of at least 5 Kb, wherein DNA with a size of at least 15, 25 or 30 Kb is specifically preferred.

According to specifically preferred embodiments of the present invention methods are provided, wherein the BAC comprises a sequence controlling the transcription of the DNA cloned into the BAC. This will allow transcription of the viral RNA and thus enable expression of the virus. Any sequence controlling transcription known in the art may be used for this purpose, including sequences driving the expression of genes derived from DNA or RNA genomes. The use of the immediately early (IE) promoter of cytomegalovirus (CMV) is preferred.

The DNA cloned into the BAC may also be flanked at the 3'-end by a poly(A)tail. The nucleic acid may comprise termination and/or polyadenylation sequences of bovine growth hormone (BGH). Additionally or alternatively, the nucleic acids may comprise sequences encoding a ribozyme, for example the ribozyme of the hepatitis δ virus (HDV).

Additional advantages may be achieved if at least one of the genes of the virus has been modified by substituting, deleting or adding nucleotides. For example the gene controlling tropism of the virus may be modified to obtain viruses with altered tropism. Alternativly, the gene controlling tropism of the virus has been substituted with the respective gene of another virus. The modification is preferably performed in the S, M and/or N genes of the virus.

In a preferred embodiment of the present invention a method is provided, wherein the DNA cloned into the BAC is capable of being transcribed into RNA which RNA can be assembled to an virion. The virion may be an infectious, attenuated, replication defective or inactivated virus.

Any RNA virus may be used in the methods of the invention. The virus can for example be a picornavirus, flavivirus, togavirus, coronavirus, toroviruses, arterivurses, calcivirus, rhabdovirus, paramixovirus, filovirus, bornavirus, orthomyxovirus, bunyavirus, arenavirus or reovirus. The use of viruses naturally having a plus strand genome is preferred.

Additionally, the present invention provides methods of preparing a viral RNA or a virion comprising steps, wherein a DNA is prepared according to one of above methods, the DNA is expressed in a suitable host cell and the viral RNA or the virion is isolated from that host cell. Any of methods for isolating viruses from the cell culture known in the art may be used. Alternatively, methods of preparing a viral RNA or a virion are disclosed, wherein the DNA of the present invention is transcribed or translated using chemicals, biological reagents and/or cell extracts and the viral RNA or the virion is subsequently isolated. For certain embodiments, the virus may subsequently be inactivated or killed.

The invention also provides methods for preparing a pharmaceutical composition comprising steps, wherein a DNA, a viral RNA or a virion is prepared according to one of the above methods and is subsequently mixed with a pharmaceutically acceptable adjuvans and/or carrier. A large number of adjuvans and carriers and diluents are known in the prior art and may be used in accordance with the present invention. The pharmaceutical is preferably a vaccine for protecting humans or animals against an infectious disease. The pharmaceutical can advantageously also be used for gene therapy.

The present invention further provides for the first time a DNA comprising sequences derived from the genomic RNA (gRNA) of a coronavirus which sequences have a homology of at least 60% to the natural sequence of the coronavirus and code for an RNA dependent RNA polymerase and at least one structural or non-structural protein, wherein a fragment of said DNA is capable of being transcribed into RNA which can be assembled to a virion.

According to the present invention the term "sequence derived from a coronavirus" is used to refer to a nucleic acid sequence which has a homology of at least 60%, preferably 75% and more preferably 85 or 95%, to a natural sequence of a coronavirus. Sequence homology can be determined using the Clustal computer program available from the European Bioinformatics Institute (EBI).

The term "coronavirus" is used according to the present invention to refer to a group of viruses having a single molecule of linear, positive sense, ssRNA of 25 to 33 Kb. These viruses usually contain 7 to 10 structural genes, i.e. genes encoding proteins that determine the viral structure. These genes are typically arranged in the viral genome in the order of 5' replicase-(hemagglutinin-esterase)-spike-envelope-membrane-nucleoprotein-3'. Additionally the viral genome may comprise a number of non-structural genes which encode a nested set of mRNAs with a common 3' end and are largely non-essential.

The term "capable of being transcribed into RNA which can be assembled into a virion" is used to characterize a DNA sequence, which—once introduced into a suitable host cell—will be transcribed into RNA and generate virions. The virions are preferably infectious viruses, but may also be inactivated, attenuated or replication defective viruses comprising said RNA. Preferably all the information necessary for expression of the virion is encoded by the DNA sequence of the present invention.

The nucleic acids of the present invention may further comprise a sequence encoding one or several heterologous genes of interest. According to the present invention a gene is characterized as a "heterologous gene" if it is not derived from the coronavirus which was used as a source for the genes encoding the RNA dependent RNA polymerase and the structural or non-structural protein. A "heterologous gene" thus also refers to genes derived from one type of coronavirus and expressed in a vector comprising sequences derived from another type of coronavirus. Any heterologous gene of interest can be inserted into the nucleic acids of the present invention. The insertion of genes encoding peptides or proteins which are recognised as an antigen from an infectious agent by the immune system of a mammal is especially preferred. The heterologous gene may thus encode at least one antigen suitable for inducing an immune response against an infectious agent, at least one molecule interfering with the replication of an infectious agent or an antibody providing protection against an infectious agent. Alternatively or additionally, the heterologous gene may encode an immune modulator, a cytokine, an immonenhancer or an anti-inflammatory compound.

The fragment of the DNA according to the present invention which is transcribed into RNA preferably has a size of at least 25 Kb. Fragments with a size of at least 30 Kb are especially preferred.

According to a preferred embodiment of the present invention the DNA further comprises sequences derived from a coronavirus coding for several or all except one of the structural or nonstructural proteins of a coronavirus. Alternatively, the DNA of the present invention further comprises sequences coding for all of the structural or non-structural proteins of a coronavirus.

According to a further embodiment, the nucleic acids of the present invention comprise a sequence controlling the transcription of a sequence derived from a coronavirus gRNA. Any sequence controlling transcription known in the art may be used for this purpose, including sequences driving the expression of genes derived from DNA or RNA genomes. The use of the immediately early (IE) promoter of cytomegalovirus (CMV) is preferred.

The nucleic acid according to the present invention may also be flanked at the 3'-end by a poly(A)tail. The nucleic acid may comprise termination and/or polyadenylation sequences of bovine growth hormone (BGH). Additionally or alternatively, the nucleic acids may comprise sequences encoding a ribozyme, for example the ribozyme of the hepatitis δ virus (HDV).

The nucleic acids of the present invention may comprise sequences derived from any coronavirus, for example derived from an isolate of the porcine transmissible gastroenteritis virus (TGEV), murine hepatitits virus (MHV), infectious bronchitis virus (IBV), bovine coronavirus (BoCV), canine coronavirus (CCoV), feline coronavirus (FcoV) or human coronavirus. According to a preferred embodiment the nucleic acid is derived from a transmissable gastroenteritis virus.

According to a further embodiment of the present invention, the DNAs of the present invention are part of a plasmid, preferably part of a bacterial artificial chromosome (BAC).

The present invention further provides host cells comprising respective nucleic acids or vectors. The host cells may be eucaryotes or procaryotes. Alternatively, the present invention provides virions comprising a nucleic acid according the present invention. Respective virions may for example be isolated from cell cultures transfected or infected with the nucleic acids of the present invention.

According to a further embodiment, the present invention provides methods for producing a virion or a viral RNA comprising steps, wherein a DNA of the present invention is introduced into a host cell, host cells containing the DNA are cultivated under conditions allowing the expression thereof and the virion or viral RNA is recovered. Additionally, methods for producing a virion or a viral RNA are provided, wherein a DNA of the present invention is mixed in vitro with chemicals, biological reagents and/or cell extracts under conditions allowing the expression of the DNA and the virion or viral RNA is recovered. The present invention also encompasses the virions and viral RNAs obtainable by either of the above methods. RNAs and virions carrying a heterologous gene are preferred. The viruses so obtained may have the form of an infectious, attenuated, replication defective or inactivated virus.

The virus may comprise modified genes, for example a modified S, N or M gene. In a specific embodiment of the present invention the modification of the S, N or M gene gives raise to an attenuated virus or a virus with altered tropism.

According to a further embodiment the invention provides a pharmaceutical preparation comprising nucleic acids, host cells or virions according to the present invention. According to a preferred embodiment the pharmaceutical preparation is a vaccine capable of protecting an animal against diseases caused by an infectious agent. The vaccine may for example comprise sequences of at least one antigen suitable for inducing an immune response against the infectious agent or an antibody providing protection against said infectious agent. The vaccine may comprise a DNA expressing at least one molecule interfering with the replication of the infectious agent. Alternatively the vaccine may comprise a vector expressing at least one antigen capable of inducing a systemic immune response and/or an immune response in mucous membranes against different infectious agents that propagate in respiratory, intestinal mucous membranes or in other tissues. The vaccine may also be a multivalent vaccine capable of protecting an animal against the infection caused by more than one infectious agent, that comprises more than one nucleic acid of the present invention each of which expresses an antigen capable of inducing an immune response against each of said infectious agents, or antibodies that provide protection against each one of said infectious agents or other molecules that interfere with the replication of any infectious agent.

The vaccines of the present invention may further comprise any of the pharmaceutically acceptable carriers or diluents known in the state of the art.

The present invention further provides methods for preparing a DNA of the present invention comprising steps, wherein an interfering defective genome derived from a coronavirus is cloned under the expression of a promotor into a BAC vector and the deletions within the defective genome are re-inserted. The method may further comprise steps, wherein toxic sequences within the viral genome are identified before re-insertion into the remaining genomic DNA. Preferably, the toxic sequences within the viral genome are the last sequences to be re-inserted before completing the genome. According to the present invention this method is suitable to yield infectious clones of coronaviruses which are stable in bacteria for at least 80 generations and thus provides a very efficient cloning vector.

The present invention provides the development of infective clones of cDNA derived from coronavirus (Almazan et al., 2000), as well as vectors constructed from said infective clones that also include heterologous nucleic acid sequences inserted into said clones. The infective clones and vectors provided by this invention have numerous applications in both basic and applied research, as well as a high cloning capacity, and can be designed in such a way that their species specificity and tropism can be easily controlled.

This patent describes the development of a method that makes it possible to obtain, for the first time in the history of coronavirus, a full-length infective cDNA clone that codes the genome of a coronavirus (Almazan et al., 2000).

A new vector or system of expression of heterologous nucleic acids based on a coronavirus generated from an infective cDNA clone that codes the genomic RNA (gRNA) of a coronavirus has been developed. In one particular realization of this invention, the coronavirus is the porcine transmissible gastroenteritis virus (TGEV).

The new system of expression can be used in basic or applied research, for example, to obtain products of interest (proteins, enzymes, antibodies, etc.), as a vaccinal vector, or in gene therapy in both humans and animals. The infective coronavirus obtained from the infective cDNA clone can be manipulated by conventional genetic engineering techniques so that new genes can be introduced into the genome of the coronavirus, and so that these genes can be expressed in a tissue- and species-specific manner to induce an immune response or for gene therapy. In addition, the expression has been optimized by the selection of new transcription-regulating sequences (TRS) that make it possible to increase the levels of expression more than a hundredfold.

The vectors derived from coronavirus, particularly TGEV, present several advantages for the induction of immunity in mucous membranes with respect to other systems of expression that do not replicate in them: (i) TGEV infects intestinal and respiratory mucous membranes (Enjuanes and Van der Zeijst, 1995), that is, the best sites for induction of secretory immunity; (ii) its tropism can be controlled by modifying the S (spike) gene (Ballesteros et al., 1997); (iii) there are non-pathogenic strains for the development of systems of expression that depend on complementing virus (Sánchez et al., 1992); and (iv) coronaviruses are cytoplasmic RNA viruses that replicate without passing through an intermediate DNA stage (Lai and Cavanagh, 1997), making its integration into the cellular chromosome practically impossible.

The procedure that has made it possible to recover an infective coronavirus from a cDNA that codes the gRNA of a coronavirus includes the following strategies:

(i) expression of the RNA of the coronavirus under the control of an appropriate promoter;
(ii) cloning of the genome of the coronavirus in bacterial artificial chromosomes (BACs);
(iii) identification of the sequences of cDNA of the coronavirus that are directly or indirectly toxic to bacteria;
(iv) identification of the precise order of joining of the components of the cDNA that codes an infective RNA of coronavirus (promoters, transcription-termination sequences, polyadenylation sequences, ribozymes, etc.); and
(V) identification of a group of technologies and processes (conditions for the growth of BACs, modifications to the purification process of BAC DNA, transformation techniques, etc.) that, in combination, allow the efficient rescue of an infective coronavirus of a cDNA.

The promoter plays an important role in increasing the expression of viral RNA in the nucleus, where it is synthesized, to be transported to the cytoplasm later on.

The use of BACs constitutes one of the key points of the procedure of the invention. As is known, cloning of eukaryotic sequences in bacterial plasmids is often impossible due to the toxicity of the exogenous sequences for bacteria. In these cases, the bacteria usually eliminate toxicity by modifying the introduced sequences. Nevertheless, in the strategy followed in this case, to avoid the possible toxicity of these viral sequences, the necessary clonings were carried out to obtain a complete cDNA of the coronavirus in BACs. These plasmids appear in only one copy or a maximum of two per cell, considerably limiting their toxicity and reducing the possibilities of interplasmid recombination.

Through the identification of the bacteriotoxic cDNA sequences of the coronavirus, the construction of the cDNA that codes the complete genome of a coronavirus can be completed, with the exception of the toxic sequences, which are added in the last step of construction of the complete genome, that is, just before transfection in eukaryotic cells, avoiding their modification by the bacteria.

One object of the present invention therefore consists in an infective double-chain cDNA clone that codes the gRNA of a coronavirus, as well as the procedure for obtaining it.

An additional object of this invention consists in a set of recombinant viral vectors that comprises said infective clone and sequences of heterologous nucleic acids inserted into said infective clone.

An additional object of this invention consists in a method for producing a recombinant coronavirus that comprises the introduction of said infective clone into a host cell, the culture of the transformed cell in conditions that allow the replication of the infective clone and production of the recombinant coronavirus, and recovering the recombinant coronavirus from the culture.

Another object of this invention consists in a method for producing a modified recombinant coronavirus that comprises introducing the recombinant viral vector into a host cell, cultivating it in conditions that allow the viral vector to replicate and the modified recombinant coronavirus to be produced, and recovering the modified recombinant coronavirus from the culture. Another object of this invention consists in a method for producing a product of interest that comprises cultivating a host cell that contains said recombinant viral vector in conditions that allow the expression of the sequence of heterologous DNA.

Cells containing the aforementioned infective clones or recombinant viral vector constitute another object of the present invention.

Another object of this invention consists in a set of vaccines that protect animals against infections caused by infectious agents. These vaccines comprise infective vectors that express at least one antigen adequate for inducing an immune response against each infective agent, or at least one antibody that provides protection against said infective agent, along with a pharmaceutically acceptable excipient. The vaccines can be mono- or multivalent, depending on whether the vectors express one or more antigens capable of inducing an immune response to one or more infectious agents, or, alternatively, one or more antibodies that provide protection against one or more infectious agents.

Another object provided by this invention comprises a method of animal immunization that consists in the administration of said vaccine.

The invention provides a cDNA clone that codes the infective RNA of a coronavirus, henceforth the infective clone of the invention, which comprises: (1) a copy of the complementary DNA (cDNA) to the infective genomic RNA (gRNA) of a coronavirus or the viral RNA itself; and (2) an expression module for an additional gene, which includes optimized transcription-promoting sequences.

In one particular realization of this invention, the coronavirus is a TGEV isolate, in particular, the PUR46-MAD isolate (Sánchez et al., 1990), modified by the replacement of the S gene of this virus by the S gene of the clone C11 TGEV isolate or the S-gene of a canine or human coronavirus.

The transcription-promoting sequence, or promoter, is an RNA sequence located at the 5'-terminal end of each messenger RNA (mRNA) of coronavirus, to which the viral polymerase RNA binds to begin the transcription of the messenger RNA (mRNA). In a particular and preferred embodiment the viral genome is expressed from a cDNA using the IE promoter of CMV, due to the high level of expression obtained using this promoter (Dubensky et al., 1996), and to previous results obtained in our laboratory that indicated that large defective genomes (9.7 kb and 15 kb) derived from the TGEV coronavirus expressed RNAs that did not undergo splicing during their transport from the nucleus, where they are synthesized, to the cytoplasm.

The infective clone of the invention also contains a transcription termination sequence and a polyadenylation signal such as that coming from the BGH gene. These termination sequences have to be placed at the 3'-end of the poly(A) tail. In one particular realization, the infective clone of the invention contains a poly(A) tail of 24 residues of A and the termination and polyadenylation sequences of the BGH separated from the poly(A) tail by the sequence of the HDV ribozyme.

The plasmid into which the infective cDNA of the virus has been inserted is a DNA molecule that possesses a replication origin, and is therefore potentially capable of replicating in a suitable cell. The plasmid used is a replicon adequate for maintaining and amplifying the infective clone of the invention in an adequate host cell such as a bacterium, for example, *Escherichia coli*. The replicon generally carries a gene of resistance to antibiotics that allows the selection of the cells that carry it (for example, cat).

In Example 1, the construction of an infective clone of TGEV under the control of the IE promoter of CMV is described. The 3'-end of the cDNA appears flanked by a 24 nt poly(A) sequence, the HDV ribozyme, and the transcription termination sequence of the BGH.

The procedure for obtaining the infective clone of the invention comprises constructing the full-length cDNA from the gRNA of a coronavirus and joining the transcription-regulating elements.

The cDNA that codes the infective gRNA of a coronavirus was obtained from a DI genome derived from a coronavirus cloned as a cDNA under the control of an appropriate promoter in a BAC, for the purpose of increasing the cDNA's stability. Then the bacteriotoxic sequences were identified and, for the purpose of eliminating that toxicity, said toxic sequences were removed and inserted at the end of the construction of the complete genome, just before transfection in eukaryotic cells. The viral progeny can be reconstituted by means of transfection of the BAC plasmid that contains the coronavirus genome in eukaryotic cells that support viral replication.

The transcription-regulating elements are joined by means of conventional techniques (Maniatis et al., 1989).

The infective clone of the invention can be manipulated by conventional genetic engineering techniques to insert at least one sequence of a heterologous nucleic acid that codes a determined activity, under the control of the promoter that is present in the infective clone and of the regulating sequences contained in the resulting expression vector.

The infective clone of the invention presents numerous applications; for example, it can be used both in basic research, for example, to study the mechanism of replication and transcription of coronaviruses, and in applied research, for example, in the development of efficient systems of expression of products of interest (proteins, enzymes, antibodies, etc.).

Appropriate cells can be transformed from the infective cDNA clone of the invention, and the virions obtained containing the complete genome of the coronavirus can be recovered. Therefore, the invention moreover provides a method for producing a recombinant coronavirus that comprises the introduction of an infective cDNA of the invention into a host cell, the culture of said cell under conditions that allow the expression and replication of the infective clone and the recovery of the virions obtained from the recombinant coronavirus, which contain the infective genome of the coronavirus. The infective clone of the invention can be introduced into the host cell in various ways, for example by transfection of the host cell with an RNA transcribed in vitro from an infective clone of the invention, or by infecting the host cell with the infective cDNA clone of the invention. Said host cells that contain the infective clone of the invention constitute an additional object of the present invention.

The invention also provides a set of recombinant viral vectors derived from an infective clone of the invention, henceforth viral vectors of-the invention. The viral vectors of the invention comprise an infective cDNA clone of the invention modified to contain a heterologous nucleic acid inserted into said infective clone under conditions that allow said heterologous nucleic acid to be expressed.

The term "nucleic acid," as it is used in this description, includes genes or gene fragments as well as, in general, any molecule of DNA or RNA.

In the sense used in this description, the term "heterologous" applied to a nucleic acid refers to a nucleic acid sequence that is not normally present in the vector used to introduce the heterologous nucleic acid into a host cell.

The heterologous nucleic acid that can contain the viral vector of the invention can be a gene or fragment that codes a protein, a peptide, an epitope, or any gene product of interest (such as antibodies, enzymes, etc.). The heterologous nucleic acid can be inserted into the infective clone of the invention by means of conventional genetic engineering techniques in any appropriate region of the cDNA, for example, after ORF 1b or between genes N and 7, following the initiator codon (AUG), and in reading frame with that gene; or, alternatively, in the zones corresponding to other ORFs. In the construction of the viral vector of the invention, it is essential that the insertion of the heterologous nucleic acid not interfere with any of the basic viral functions.

The viral vector of the invention can express one or more activities. In this latter case, the viral vector will include as many sequences of heterologous nucleic acid as activities to be expressed, preceded by one or several promoters, or by a promoter and various ribosome recognition sites (IRES, internal ribosome entry sites), or by various promoters and one ribosome recognition site.

Therefore, the invention provides a method for producing a product of interest that comprises cultivating a host cell that contains a viral vector of the invention under conditions that allow the heterologous nucleic acid to be expressed and the product of interest to be recovered. Said host cells that contain the viral vector of the invention constitute an additional object of the present invention.

The viral vector of the invention can be designed so that its species specificity and tropism can be easily controlled. Due to these characteristics, a very interesting application of the viral vectors of the invention is their use in gene therapy as a vector of the gene of interest, or as a vaccinal vector to induce immune responses against different pathogens.

The invention furthermore provides vaccines, capable of protecting an animal against the infection caused by an infectious agent, that comprise (i) at least one viral vector of the invention that expresses at least one antigen suitable for inducing an immune response against said infectious agent, or an antibody that provides protection against said infectious agent, along with, optionally, (ii) a pharmaceutically acceptable excipient.

In the sense used in this description, "inducing protection" should be understood as the immune response of the receiving organism (animal to be immunized) induced by the viral vector of the invention, through suitable mechanisms such as that induced by substances that potentiate cellular response (interleukins, interferons, etc.), cellular necrosis factors, and similar substances that protect the animal from infections caused by infectious agents.

Included under the term "animal" are all animals of any species, preferably mammals, including man.

The term "infectious agent" in the sense used in this description includes any viral, bacterial, fungal, parasitic, or other infective agent that can infect an animal and cause it a pathology.

In one particular realization, the vaccine provided by this invention comprises at least one viral vector of the invention that expresses at least one antigen capable of inducing a systemic immune response and/or an immune response in mucous membranes against different infectious agents that propagate in respiratory or intestinal mucous membranes. The vectors of the invention are quite suitable to induce immunity in mucous membranes as well as lactogenic immunity, which is of special interest in protecting newborns against intestinal tract infections.

In another particular realization, the vaccine provided by this invention comprises at least one viral vector of the invention that expresses at least one gene that codes for the light and heavy chains of an antibody of any isotype (for example, $IgG_1$, IgA, etc.) that protects against an infectious agent.

Species specificity can be controlled so that the viral vector may express the S protein of the envelope of a coronavirus that infects the desired species (man, dog, cat, pig, etc.), suitable to be recognized by the cellular receptors of the corresponding species.

The vaccines provided by this invention can be monovalent or multivalent, depending on whether the viral vectors of the invention express one or more antigens capable of inducing an immune response to one or more infectious agents, or one or more antibodies that provide protection against one or more infectious agents.

In a particular realization of this invention, monovalent vaccines capable of protecting man, pigs, dogs and cats against different infectious human, porcine, canine, and feline agents are provided, and tropism is controlled by expressing the S glycoprotein of the coronavirus with the desired species specificity.

The monovalent vaccines against porcine infectious agents can contain a vector that expresses an antigen selected from the group consisting essentially of antigens of the following porcine pathogens: *Actinobacillus pleuropneumoniae*, *Actinobacillus suis*, *Haemophilus parasuis*, porcine parvovirus, *Leptospira*, *Escherichia coli*, *Erysipelotrix rhusiopathiae*, *Pasteurella multocida*, *Bordetella bronchiseptica*, *Clostridium sp.*, *Serpulina hydiosenteriae*, *Mycoplasma hyopneumoniae*, porcine epidemic diarrhea virus (PEDV), porcine respiratory coronavirus, rotavirus, or against the pathogens that cause porcine respiratory and reproductive syndrome, Aujeszky's disease (pseudorabies), swine influenza, or transmissible gastroenteritis, and the etiological agent of atrophic rhinitis and proliferative ileitis. The monovalent vaccines against canine infectious agents can contain an expression vector that expresses an antigen selected from the group essentially consisting of antigens of the following canine pathogens: canine herpes viruses, types 1 and 2 canine adenovirus, types 1 and 2 canine parvovirus, canine reovirus, canine rotavirus, canine coronavirus, canine parainfluenza virus, canine influenza virus, distemper virus, rabies virus, retrovirus, and canine calicivirus.

The monovalent vaccines against feline infectious agents can contain an expression vector that expresses an antigen selected from the group essentially consisting of antigens of the following feline pathogens: cat calicivirus, feline immunodeficiency virus, feline herpes viruses, feline panleukopenia virus, feline reovirus, feline rotavirus, feline coronavirus, cat infectious peritonitis virus, rabies virus, feline *Chlamydia psittaci*, and feline leukemia virus.

The vectors can express an antibody that provides protection against an infectious agent, for example, a porcine, canine or feline infectious agent such as those cited above. In one particular realization, the vector expresses the recombinant monoclonal antibody identified as 6A.C3, which neutralizes TGEV, expressed with isotypes $IgG_1$ or IgA, in which the constant part of the immunoglobulin is of porcine origin, or neutralizing antibodies for human and porcine rotaviruses.

As the excipient, a diluent such as physiological saline or other similar saline solutions can be used. Likewise, these vaccines can also contain an adjuvant from those usually used in the formulation of both aqueous vaccines, such as aluminum hydroxide, QuilA, suspensions of alumina gels and the like, and oily vaccines based on mineral oils, glycerides, fatty acid derivatives, and their mixtures.

The vaccines of the present invention can also contain cell-response-potentiating (CRP) substances, that is, substances that potentiate subpopulations of helper T-cells ($Th_1$ and $Th_2$) such as interleukin-1 (IL-1), IL-2, IL-4, IL-5, IL-6, IL-12, gamma-IFN (gamma-interferon), cellular necrosis factor, and similar substances that could theoretically provoke cellular immunity in vaccinated animals. These CRP substances could be used in vaccine formulations with aqueous or oily adjuvants. Another type of adjuvants that modulate and immunostimulate cellular response can also be used, such as MDP (muramyl dipeptide), ISCOM (Immunostimulant Complex), or liposomes.

The invention provides multivalent vaccines capable of preventing and protecting animals from infections caused by different infectious agents. These multivalent vaccines can be prepared from viral vectors of the invention into which the different sequences that code the corresponding antigens have been inserted in the same recombinant vector, or by constructing independent recombinant vectors that would later be mixed for joint inoculation. Therefore, these multivalent vaccines comprise a viral vector that contains more than one sequence of heterologous nucleic acids that code for more than one antigen or, alternatively, different viral vectors, each of which expresses at least one different antigen.

Analogously, multivalent vaccines that comprise multivalent vectors can be prepared using sequences that code antibodies that protect against infectious agents, instead of sequences that code the antigens.

In one particular realization of this invention, vaccines capable of immunizing humans, pigs, dogs, and cats against different porcine, canine and feline infectious agents, respectively, are provided. For this, the viral vectors contained in the vaccine must express different antigens of the human, porcine, canine or feline pathogens mentioned above or others.

The vaccines of this invention can be presented in liquid or lyophilized form and can be prepared by suspending the recombinant systems in the excipient. If said systems were in lyophilized form, the excipient itself could be the reconstituting substance.

Alternatively, the vaccines provided by this invention can be used in combination with other conventional vaccines, either forming part of them or as a diluent or lyophilized fraction to be diluted with other conventional or recombinant vaccines.

The vaccines provided by this invention can be administered to the animal orally, nasally, subcutaneously, intradermally, intraperitoneally, intramuscularly, or by aerosol.

The invention also provides a method for the immunization of animals, in particular pigs, dogs and cats, against one or various infectious agents simultaneously, that comprises the oral, nasal, subcutaneous, intradermal, intraperitoneal, intramuscular, or aerosol administration (or combinations thereof) of a vaccine that contains an immunologically efficacious quantity of a recombinant system provided by this invention.

In addition, the invention also provides a method for protecting newborn animals against infectious agents that infect said animals, consisting in the oral, nasal, subcutaneous, intradermal, intraperitoneal, intramuscular, or aerosol administration (or combinations thereof) of a vaccine of those provided by this invention to mothers before or during the gestation period, or to their offspring.

The invention is illustrated by the following examples, which describe in detail the obtainment of infective clones and the construction of the viral vectors of the invention. These examples should not be considered as limiting the scope of the invention, but as illustrating it. In said example, the transformation and growth of bacteria, DNA purification, sequence analysis, and the-assay to evaluate the stability of the plasmids were carried out according to the methodology described below.

Transformation of Bacteria

All of the plasmids were electroporated in the *E. coli* DH10B strain (Gibco BRL), introducing slight modifications to previously described protocols (Shizuya et al., 1992). For each transformation, 2 μL of the ligation and 50 μL of competent bacteria were mixed in 0.2-cm dishes (BioRad) and electroporated at 200 Ω, 2.5 kV, and 25 μF. Then, 1 mL of SOC medium (Maniatis et al., 1989) was added at each transformation, the cells were incubated a 37° C. for 45 min, and finally, the recombinant colonies were detected on plates of LB SOC media (Maniatis et al., 1989) with 12.5 μg/mL of chloramphenicol.

Growth Conditions of the Bacteria

The bacteria containing the original plasmids, in which the incomplete genome of TGEV was cloned (FIG. 3), were grown at 37° C., showing normal growth kinetics. On the other hand, the BAC that contained the complete cDNA was grown at 30° C. for the purpose of minimizing instability as much as possible. Even so, the size of the colonies was reduced and incubation periods of up to 24 h were necessary to achieve normal colony sizes.

Purification of DNA

The protocol described by Woo (Woo et al., 1994) was followed, with slight modifications. From a single colony, 4 L of LB were inoculated with chloramphenicol (12.5 μg/ml). After an incubation period of 18 h at 30° C., the bacteria were collected by centrifugation at 6,000 G, and the plasmid was purified using the Qiagen Plasmid Maxipreparations kit according to the manufacturer's recommendations. By means of this procedure, it was observed that the plasmid DNA obtained was contaminated with bacterial DNA. To eliminate the contaminating bacterial DNA, the plasmidic DNA was purified by means of centrifugation at 55,000 rpm for 16 h on a CsCl gradient. The yield obtained was between 15 and 30 μg/L, depending on the size of the plasmid.

Sequence Analysis

The DNA was sequenced in an automatic sequencer (373 DNA Sequencer, Applied Biosystems) using dideoxynucleotides marked with fluorochromes and a temperature-resistant polymerase (Perkin Elmer). The reagents were obtained by way of a kit (ABI PRISM Dye Terminator Cycle Sequencing Ready Reaction Kit) from the Applied Biosystems company. The thermocycler used to perform the sequencing reactions was a "GeneAmpPCR System 9600" (Perkin Elmer).

The joining of the sequences and their comparison with the consensus sequence of the TGEV were carried out using the SeqMan II and Align (DNASTAR) programs, respectively. No differences in relation to the consent sequence were detected.

Stability of the Plasmids

From the original glycerolates, the bacteria that contained recombinant pBeloBAC11 plasmids were grown in 20 mL of LB with chloramphenicol (12.5 μg/mL) for 16 h at 30° C. and 37° C. This material was considered passage 0. The bacteria were diluted $10^6$ times and grown at 30° C. and 37° C. for 16 h. Serial passages were realized during eight consecutive days (each passage represents approximately 20 generations). The plasmid DNA was purified by Miniprep at passages 0 and 8 (160 generations) and analyzed with restriction endonucleases. The two plasmids that contained part of the genome of TGEV were highly stable, whereas the plasmid that contained the complete genome of TGEV showed a certain instability after 40 generations (at this point approximately 80% of the DNA presented the correct restriction pattern).

EXAMPLE 1

Construction of a Recombinant Vector based on a Clone of Infective cDNA Derived from TGEV 1.1 Generation of an Infective cDNA of TGEV For the purpose of obtaining a cDNA that coded for the complete TGEV genome, we originally started with a cDNA that coded for the defective DI-C genome (Méndez et al., 1996). This cDNA, with an approximate length of one third of the TGEV genome, was cloned in the low-copy pACNR1180 plasmid (Ruggli et al., 1996) and its sequence was determined. The cDNA that coded the defective genome was efficiently rescued (replicated and packaged) with the help of a complementing virus (Méndez et al., 1996; Izeta et al., 1999).

The DI-C genome presents three deletions ($\Delta 1$, $\Delta 2$, and $\Delta 3$) of approximately 10, 1 and 8 kilobases (kb), at ORFs 1a, 1b, and between genes S and 7, respectively (see FIG. 1).

The strategy followed to complete the sequence of a cDNA that would code for an infective TGEV genome was to incorporate, step by step, the sequences deleted in the DI-C genome, analyzing the bacteriotoxicity of the new generated constructions. This aspect is very important, since it is widely documented in the scientific literature that recombinant plasmids presenting cDNAs of RNA virus generally grew poorly and were unstable (Boyer and Haenni, 1994; Rice et al., 1989; Mandl et al., 1997).

The first deletion to be completed was deletion $\Delta 2$, of 1 kb, of ORF 1b, yielding a stable recombinant plasmid. The sequence that lacked ORF 1a was introduced by cloning cDNA fragments A, B, C, and D (FIG. 1) (Almazan et al., 2000) in such a way that all the information required for the gene of the replicase would be complete. The recombinant plasmid obtained was unstable in the bacteria, generating new plasmids that had incorporated additions and deletions in fragment B (Almazan et al., 2000). Interestingly, the elimination of a 5,198 bp ClaI-ClaI restriction fragment that encompassed the region of the genome comprised between nucleotides 4,417 and 9,615 (Penzes et al., 1999) yielded a relatively stable plasmid in the *E. coli* DH10B strain. Later, the sequence of deletion $\Delta 3$ was added by cloning all the genetic information for the structural and nonstructural proteins of the 3'-end of the TGEV genome (FIG. 1).

For the purpose of incrementing the stability of the TGEV cDNA, it was decided that it would be subcloned in BAC using the pBeloBAC11 plasmid (Kim et al., 1992) (see FIG. 2). The pBeloBAC11 plasmid was a generous gift from H. Shizuya and M. Simon (California Institute of Technology). The plasmid, 7,507 bp in size, includes the replication origin of the F factor from parB, parC, *E. coli* (oriS) and the genes necessary to keep a single copy of the plasmid per cell (parA, and repE). The plasmid also presents the gene of resistance to chloramphenicol (cat) as a selection marker. The cDNA was cloned under the control of the IE promoter of CMV, due to the high level of expression obtained using this promoter (Dubensky et al., 1996) and to previous results obtained in our laboratory, indicating that large (9.7 kb and 15 kb) defective genomes derived from TGEV expressed RNAs that did not undergo splicing during transport from the nucleus, where they are synthesized, to the cytoplasm (Izeta et al., 1999; Penzes et al., 1999; Almazan et al., 2000). The generated TGEV cDNA (pBAC-TcDNA-AClaI) contained the information for the genes of the replicase, with the exception of the deleted 5,198 bp ClaI fragment, and all the information of the structural and nonstructural genes. The 3'-end of the cDNA appears flanked by a 24 nt polyA sequence, the HDV ribozyme, and the transcription termination sequence of BGH (Izeta et al., 1999). On the other hand, the ClaI fragment necessary to generate a complete genome of TGEV was cloned in BAC, generating the plasmid pBAC-B+C+D5', which contained the region of the TGEV genome between 4,310 and 9,758 (see FIG. 3). Both plasmids were grown in the E. coli DH10B strain and sequenced in their entirety. The sequence obtained was identical to the consent sequence of the PUR46-MAD isolate of TGEV provided at the end of this document (SEQ ID NO: 1), with the exception of two replacements in the positions of nucleotides 6,752 (A=>G, silent) and 18,997 (T=>C, silent), and the changes in the S gene of the PUR46-MAD that has been replaced by the D gene of isolate C11 (these changes are indicated in FIG. 4).

Furthermore, for the purpose of generating a cDNA that would code a virulent TGEV, the S gene of the PUR46-MAD isolate, which replicates at highs levels in the respiratory tract (>$10^6$ PFU/g of tissue) and at low levels in the intestinal tract (<$10^3$ PFU/mL), was completely replaced by the S gene of TGEV clone 11, henceforth C11, which replicates with elevated titers both in the respiratory tract (<$10^6$ PFU/mL) and in the intestinal tract (<$10^6$ PFU/mL) (Sánchez et al., 1999). The S gene of C11 presents 14 nucleotides that differ from the S gene of the PUR46-MAD isolate, plus a 6 nt insertion at the 5'-end of the S gene (see FIG. 4) (Sánchez et al., 1999). Previous results in our laboratory (Sánchez et al., 1999) showed that mutants generated by directed recombination, in which the S gene of the PUR46-MAD isolate of the TGEV was replaced with the S gene of the C11 intestinal isolate, acquired intestinal tropism and increased virulence, unlike the natural PUR46-MAD isolate of the TGEV that replicates very little or not at all in the intestinal tracts of infected pigs.

Figure 3:
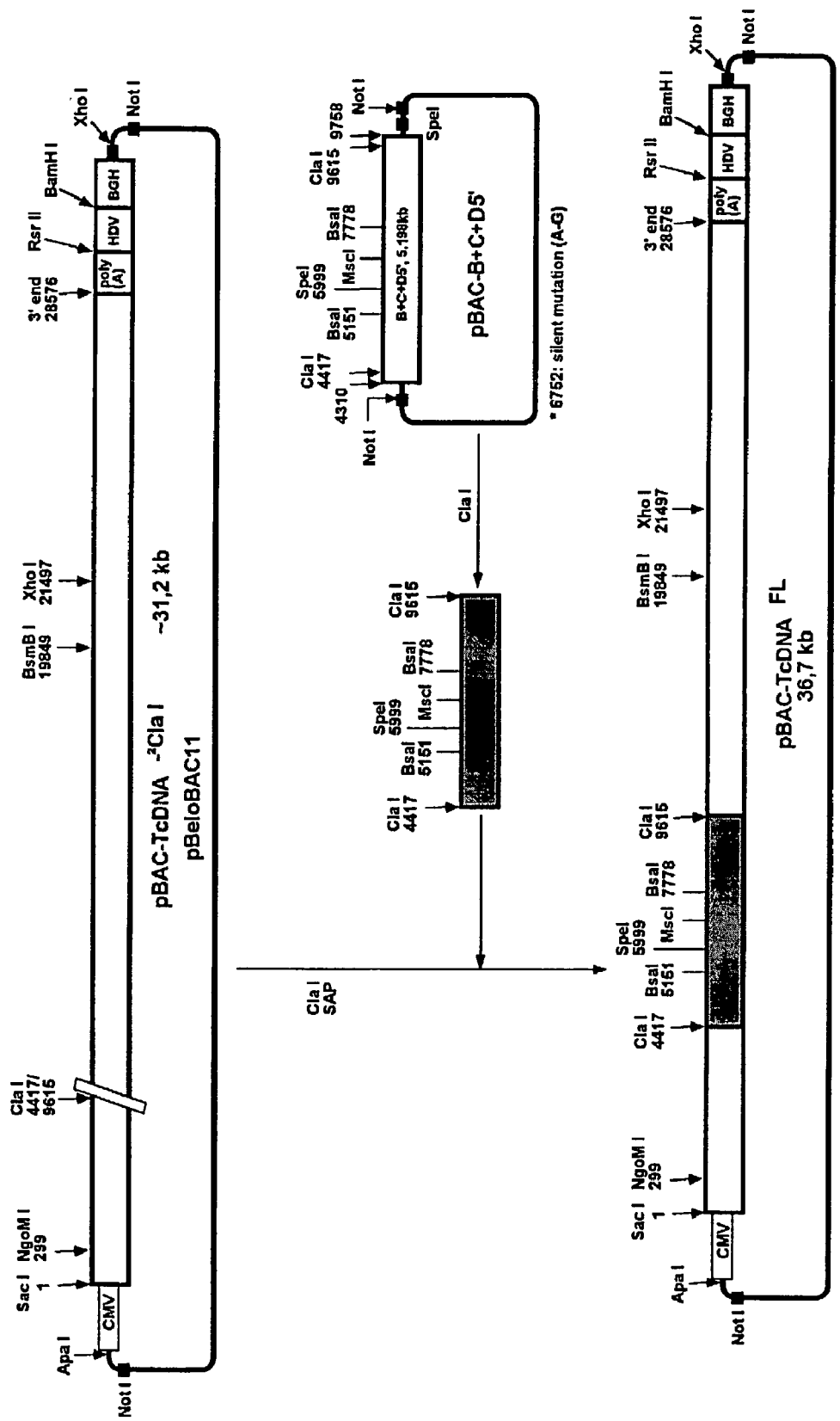
FIG. 3 shows the structure of the basic plasmids used in the construction of TGEV cDNA. The pBAC-TcDNA$^{\Delta ClaI}$ plasmid contains all the information of the TGEV RNA except for one ClaI-ClaI fragment of 5,198 bp. The cDNA was cloned under the immediately early (IE) promoter of expression of cytomegalovirus (CMV) and is flanked at the 3'-end by a poly(A) tail with 24 residues of A, the ribozyme of the hepatitis delta virus (HDV), and the termination and polyadenylation sequences of bovine growth hormone (BGH). The pBAC-B+C+D5' plasmid contains the ClaI-ClaI fragment required to complete the pBAC-TcDNA$^{\Delta ClaI}$ until the cDNA is full length. The pBAC-TcDNA$^{FL}$ plasmid contains the full-length cDNA of TGEV. SAP: shrimp alkaline phosphatase.
Figure 4:
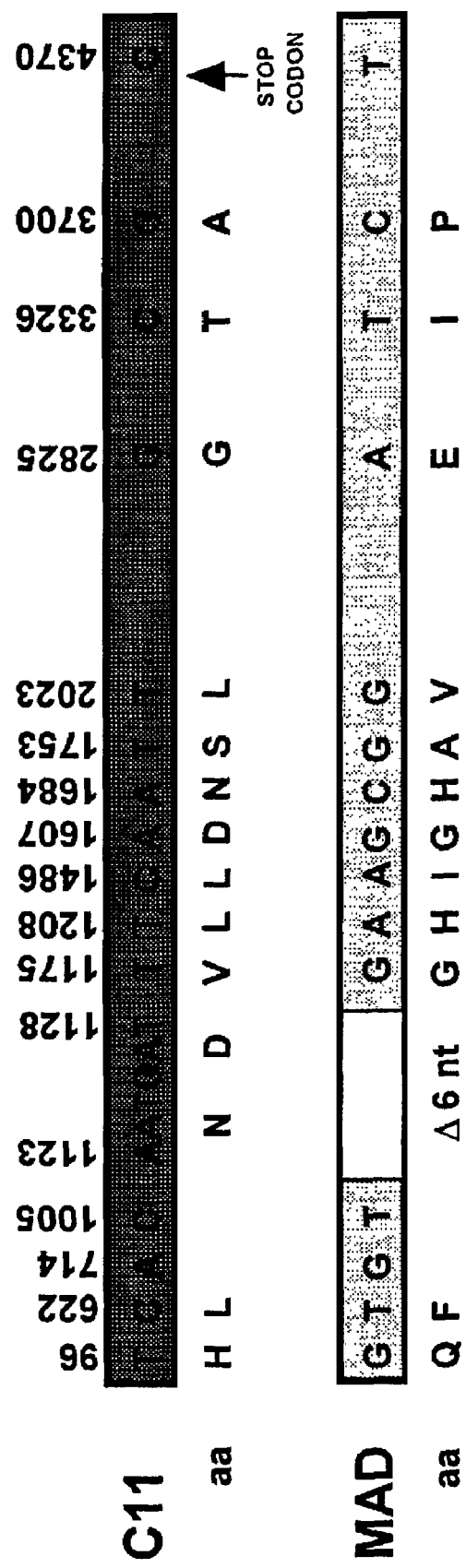
FIG. 4 shows the differences in the nucleotide sequence of the S gene of the clones of TGEV PUR46-MAD (MAD) (SEQ ID NOS: 8 & 9) and C11 (SEQ ID NOS: 6 & 7). The numbers indicate the positions of the substituted nucleotides, considering as nucleotide one of each gene the A of the initiating codon. The letters within the bars indicate the corresponding nucleotide in the position indicated. The letters located beneath the bars indicate the amino acid (aa) substitutions coded by the nucleotides that are around the indicated position. Δ6 nt indicates a 6-nucleotide deletion. The arrow indicates the position of the termination codon of the S gene.

A cDNA was constructed from the PUR46-MAD isolate of TGEV with the S gene of the intestinal isolate C11, by means of cloning of the 5,198 bp ClaI-ClaI fragment, obtained from the pBAC-B+C+D5' plasmid, in the pBAC-TcDNA$^{-\Delta ClaI}$ plasmid, to generate the pBAC-TcDNA$^{FL}$ plasmid that contains the cDNA that codes for the complete TGEV genome (FIG. 3).

The stability in bacteria of the plasmids used in the construction of the clone of infective cDNA (pBAC-TcDNA$^-$ $\Delta ClaI$ and pBAC-ClaI$^F$), as well as the plasmid that contains the complete cDNA (pBAC-TcDNA$^{FL}$); was analyzed after being grown in E. coli for 160 generations. The stability was analyzed by means of digestion with restriction enzymes of the purified DNAs. No deletions or insertions were detected, although the presence of minor changes not detected by the analysis technique used cannot be ruled out in the case of the pBAC-TcDNA$^{-\Delta ClaI}$ plasmid and the pBAC-B+C+D5' plasmid. In the case of the pBAC-TcDNA plasmid, which contains the complete genome of TGEV, a certain instability was detected after 40 generations (at this point approximately 80% of the DNA presented the correct restriction pattern). This slight instability, however, does not represent an obstacle to the rescue of the infective virus, since 20 generations (4 L of culture) of bacterial growth are sufficient to generate a quantity of plasmid DNA that allows the virus to be rescued.

1.2 Rescue of an Infective TGEV from a cDNA that Codes for the complete Genome

Figure 5:
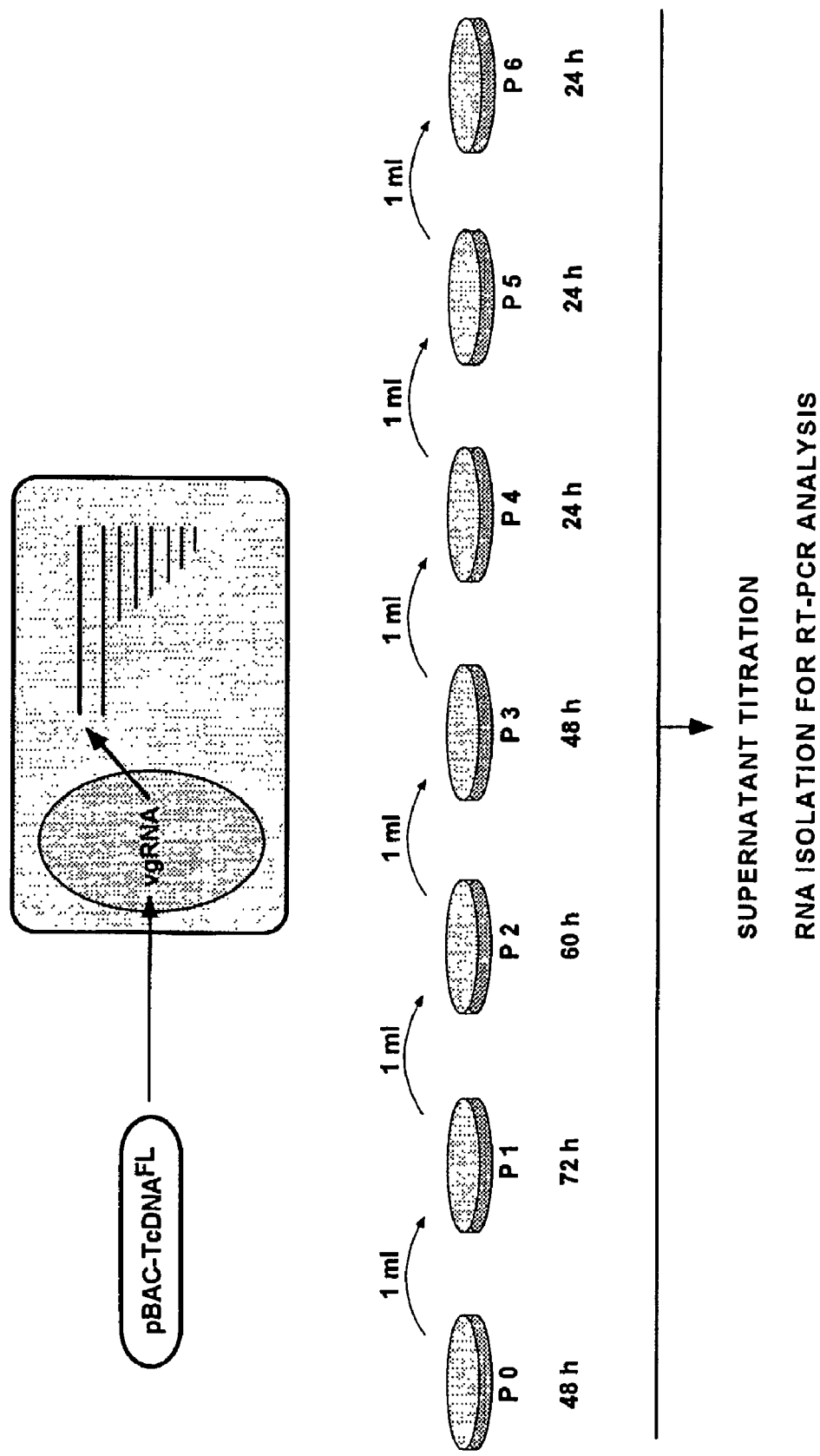
FIG. 5 shows the strategy followed to rescue the infective TGEV from the full-length TGEV cDNA. The pBAC-TcDNA$^{FL}$ plasmid was transfected to ST cells (pig testicle cells), and 48 h after transfection, the supernatant was used to infect new ST cells. The virus was passed at the times indicated. At each passage, aliquots of supernatant and of cellular monolayer were collected for virus titration and isolation of RNA for RT-PCR analysis, respectively. vgRNA: full-length viral RNA.
Figure 7:
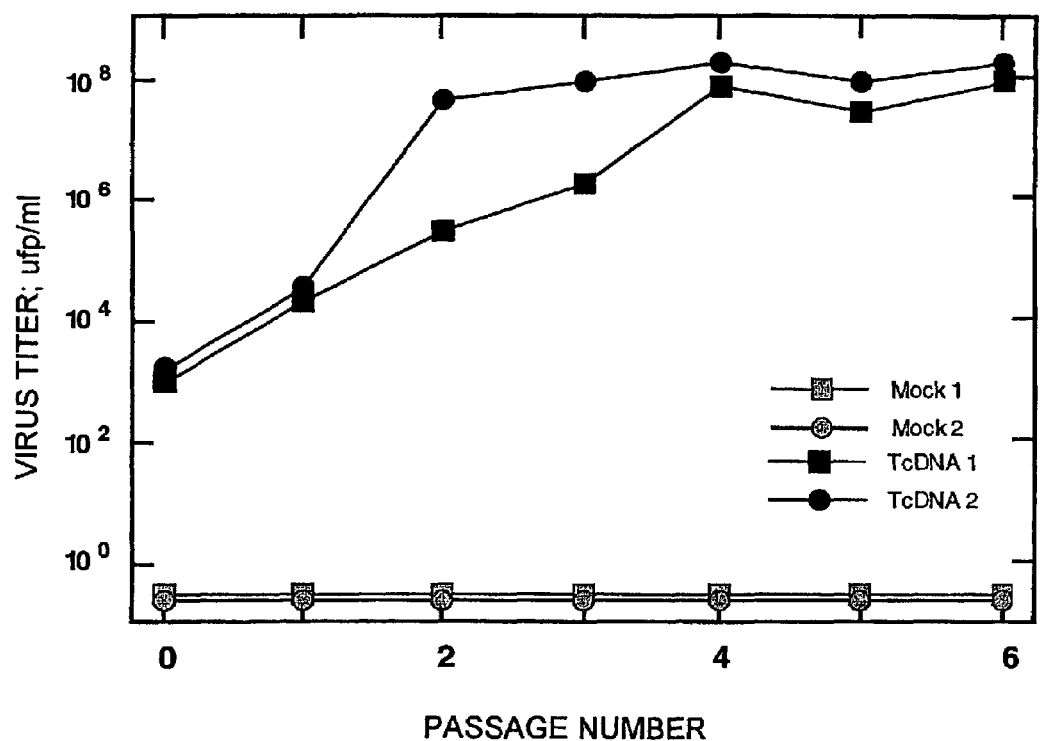
FIG. 7 shows the evolution of the viral titer with the passage. A graph representing the viral titer in the supernatant of two series of cellular monolayers (1 and 2) at different passages after transfection with pBAC-TcDNA$^{FL}$ is shown. Mock 1 and-2 refer to nontransfected ST cells. TcDNA 1 and 2 refer to ST cells transfected with pBAC-TcDNA$^{FL}$.

ST cells were transfected with the pBAC-TcDNA$^{FL}$ plasmid. At 48 h posttransfection, the supernatant of the culture was collected and passed into ST cells six times (see FIG. 5). Starting at passage 2, at 14 h postinfection, the cytopathic effect became apparent, extending later, at 20 h postinfection, to practically all of these cells that formed the monolayer (see FIG. 6). On the other hand, the titer of rescued virus increased rapidly with the passages, reaching values on the order of $10^8$ PFU/mL as of passage 3 (see FIG. 7). The experiment was repeated five times, and in ail cases, infective virus with similar titers were recovered, whereas, in the case of non-transfected ST cells or ST cells transfected with a similar plasmid, where the ClaI-ClaI fragment was found in the opposite orientation, virus was never recovered.

Figure 8:
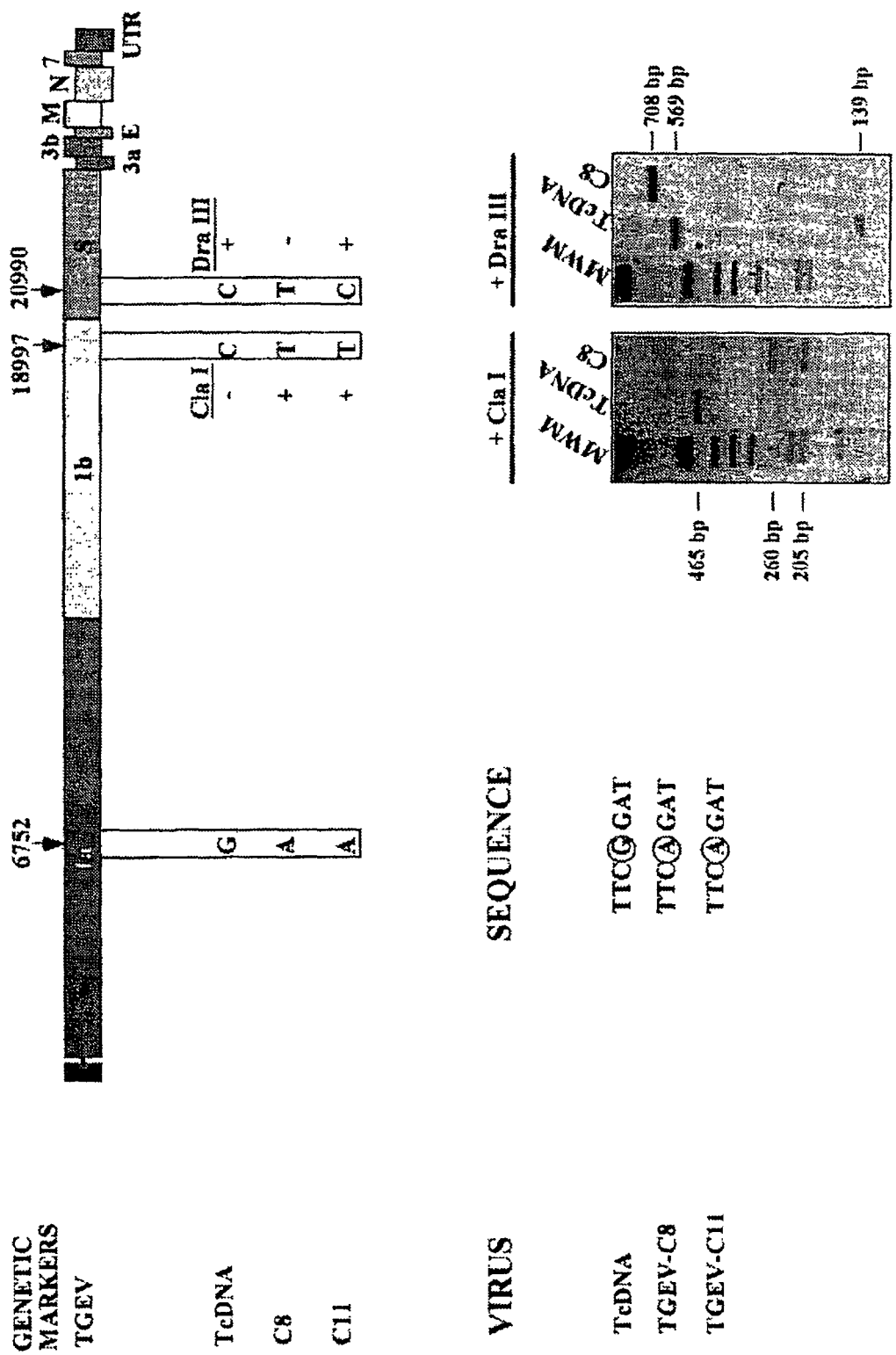
FIG. 8 shows the results of the analysis of the sequence of the virus recovered after transfecting ST cells with pBAC-TcDNA$^{FL}$. The structure of the TGEV genome is indicated at the top of the figure. Likewise, the differences in the sequence of nucleotides (genetic markers) between the virus recovered from the pBAC-TcDNA$^{FL}$ (TcDNA) plasmid, and TGEV clones C8 and C11 are indicated. The positions of the differences between the nucleotides are indicated by the numbers located over the bar. The cDNA sequences of the TcDNA virus and of clone C11 were determined by sequencing the fragments obtained by RT-PCR (reverse-transcription and polymerase chain reaction). The sequence of clone C8 is being sent for publication (Penzes et al., 1999) and is included at the end of this patent. The restriction patterns are shown with ClaI and DraIII of the fragments obtained by RT-PCR that include nucleotides 18,997 and 20,990 of the TcDNA and C8 viruses. The restriction patterns show the presence or absence of ClaI and DraIII sites in the cDNA of these viruses. The result of this analysis indicated that the TcDNA virus recovered had the S-gene sequence expected for isolate C11. MWM: molecular weight markers.

For the purpose of eliminating the possibility that the virus obtained was the product of contamination, the sequence at positions 6,752 and 18,997 was determined by means of sequencing of cDNA fragments amplified by RT-PCR using the genomic RNA of the rescued virus as a template. The analysis of the sequence determined that the nucleotides in positions 6,752 and 18,997 were those present in the cDNA. Furthermore, the rescued virus presented, in the cDNA sequence of the S gene, a restriction site DraIII at position 20,990, as was expected for the S gene of C11 (FIG. 8). The presence of these three genetic markers confirmed that the isolated virus came from the cDNA.

Figure 10:
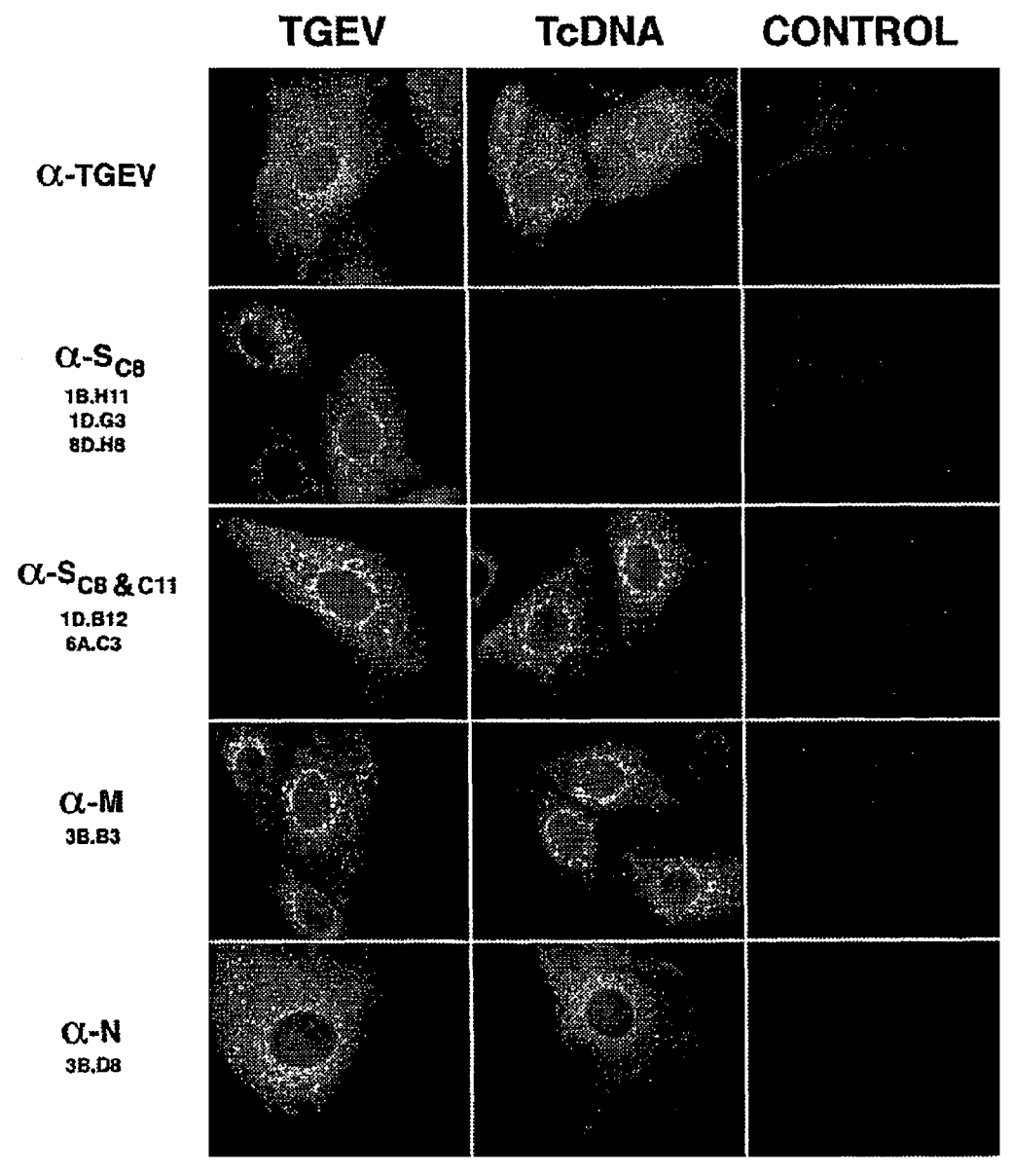

In a more in-depth characterization of the virus generated, a comparative analysis was made by immunofluorescence of infected cells with the virus recovered (TcDNA) after transfection with the pBAC-TcDNA$^{FL}$ plasmid or cells infected with the PUR46-MAD isolate of the TGEV. For this, specific polyclonal and monoclonal antibodies that recognized both the C11 isolate and the PUR46-MAD isolate, or only the latter, were used (see FIG. 10). The results obtained confirmed the antigenicity expected for the new TcDNA virus. The polyclonal antibody specific for TGEV, the expected specific monoclonal of the S protein (ID.B12 and 6A.C3), as well as the specific monoclonal of the M (3B.B3) and N (3B.D8) proteins recognized both the TcDNA and the PUR46-MAD. The data obtained indicated that the virus generated presented the M and N proteins of the PUR46-MAD isolate and the S protein of the C11 isolate, as had been designed in the original cDNA.

1.3 In Vivo Infectivity and Virulence

For the purpose of analyzing the in vivo, infectivity of the TcDNA virus, a group of five newborn pigs was inoculated with virus cloned from passage 6, and mortality was analyzed. The five inoculated pigs died 3 to 4 days postinoculation, indicating that the TcDNA virus was virulent. In contrast, two pigs inoculated only with the diluent of the virus and maintained in the same conditions did not suffer alterations.

1.4 Optimization of the Levels of Expression by Modification of the Transcription-Regulating Sequences RNA synthesis in coronavirus takes place by means, of an RNA-dependent process, in which the mRNAs are transcribed from templates with negative polarity. In the TGEV, a conserved consensus sequence, CUAAAC, appears, which is located just in front of the majority of the genes. These sequences represent signals for the transcription of the subgenomic mRNAs. In coronavirus, there are between six and eight types of mRNAs with variable sizes, depending on the type of coronavirus and of the host. The largest corresponds to the genomic RNA, which in turn serves as mRNA for ORFs 1a and 1b. The rest of the mRNAs correspond to subgenomic mRNAs. These RNAs are denominated mRNA 1 to 7, in decreasing size order. On the other hand, some mRNAs that have been discovered after the set of originally described mRNAs have been denominated with the name of the corresponding mRNA, a dash, and a number, e.g., mRNA 2-1. The mRNAs present a coterminal structure in relation to the structure of the genomic RNA. With the exception of the smallest mRNA, the rest are structurally polycistronic, while, in general, only the ORF located closest to 5' is translated.

The efficiency in the expression of a marker gene (GUS) has been studied using different sequences flanking the 5'-terminal of the minimal intergenic (IG) sequence CUAAAC (FIG. 11), different sequences flanking the 3'-terminal of the IG sequence (FIG. 12), and various insertion sites (FIG. 13). The results obtained (FIGS. 11 to 13) indicated that optimal expression was achieved with a TRS consisting of: (i) the −88 nt flanking the consent sequence for the N gene of TGEV; (ii) the IG sequence; and (iii) the 3'-flanking sequence of the IG sequence of the S gene. Furthermore, in agreement with the results obtained in relationship to the point of insertion of the heterologous gene, the greatest levels of expression were achieved when the heterologous gene was located at the 3'-end of the genome. A TRS such as that described allows the GUS to be expressed at levels between 2 and 8 μg per $10^6$ cells.

1.5 Tissue Specificity of the System of Expression

Many pathogens enter the host through the mucous membranes. To prevent this type of infections, it is important to develop systems of expression that allow the induction of high levels of secretory immunity. This can be achieved fundamentally through the administration of antigens in the lymph nodes associated with the respiratory and intestinal tract. To achieve this goal, and in general to direct the expression of a gene at the tissue of interest, the molecular bases of the tropism of TGEV have been studied. These studies have showed that the tissue specificity of TGEV can be modified by the construction of recombinant viruses containing the S gene of coronavirus with the desired tropism (Ballesteros et al., 1997; Sánchez et al., 1999). This information makes it possible to construct systems of expression based on cDNA genomes of coronavirus with respiratory or intestinal tropism.

1.6 Expression of the Viral Antigen Coded by the ORF5 of PRRSV using Infective cDNA For the purpose of optimizing the levels of expression of heterologous genes, constructions were made from a vector of interchangeable modules flanked by cloning sequences that facilitate the exchange of TRSs and heterologous genes within the vector. The construction, which included ORF 5 of the PRRSV (Porcine respiratory and reproductive syndrome virus) flanked at the 5'-end by the minimal IGS consensus sequence (CUAAAC) preceded by the −88 nts flanking the gene of the viral nucleocapsid (N), and at the 3'-end by restriction site SalI (GTCGAC) and a sequence analogous to that of Kozak (AC)GACC, yielded an optimal expression (about 10 μg/$10^6$ cells). In principle, these levels of expression of the heterologous gene are more than sufficient to induce an immune response. The heterologous gene was inserted into the position previously occupied by genes 3a and 3b of the virus, which are dispensable.

1.7 Induction of an Immune Response in Swine to an Antigen Expressed with the cDNA Derived Virus Vector Using the same type of virus vector derived from the cDNA and the TRSs described above, the gene encoding the green fluorescent protein (GFP) was expressed at high levels (20 μg of protein per million of cells in swine testis, ST, cells). The expression levels were stable for more than 20 passages in cell culture. Furthermore, a set of swine were immunized with the live virus vector, that was administered by the oral, intranasal and intragastric routes and a strong humeral immune response was detected against both the virus vector and the GFP. Interestingly, no secondary effect was observed in the inoculated animals after the administration of three doses of the virus vector.

1.8 Construction of a Safe Virus Vector that Expresses the Foreign Gene without Leading to the Generation of an Infectious Virus.

To design vector for humans, biosafety is a priority. To achieve this goal, three types of safety guards are being engineered in the vector. Two of these are based on the deletion of two virus components, mapping at different positions of the virus genome, essential for the replication of the virus. These components are being provided in trans by a packaging cell line. This cell (Baby Hamster Kidney, BHK) expresses the missing TGEV genes encoding essential structural proteins of the virus (the envelope E and the membrane M proteins). The third safety guard is the relocation of the packaging signal of the virus genome, in such a way that the recovery of an infectious virus by recombination is prevented, leading to the generation of a suicide vector that efficiently expresses the heterologous genes but that is unable to propagate even to the closest neighbor cell.

With the design of the new vector for use in humans, we are not producing a new virus that could be propagated within the human species, since this vector can not be transmitted from cell to cell in human beings. The vector is based on a replication defective virus. It can only be grown in the vaccine factory by using packaging cells complementing the deletions of the virus. These safety guards represent novel procedures in the engineering of coronaviruses. The recombinant virus with a new tropism will be replication competent at least in feline cells, since these cells replicate human, porcine, canine and feline coronaviruses.

Deposition of Microorganisms:

The bacterium derived from *Escherichia coli,* carrying the plasmid with the infective clone of the invention, identified as *Escherichia coli* pBAC-TcDNA$^{FL}$, has been deposited with the Spanish Collection of Type Cultures (CECT), Burjassot (Valencia), on Nov. 24$^{th}$ 1999, under registration number CECT 5265.

BIBLIOGRAPHY

Ahlquist, P., R. French, M. Janda, and L. S. Loesch-Fries. (1984). Multicomponent RNA plant virus infection derived from cloned viral cDNA. *Proc. Natl. Acad. Sci. USA.* 81:7066-7070.

Almazan, F., J. M. González, Z. Pénzes, A. Izeta, E. Calvo, J. Plana-Durán, and L. Enjuanes. (2000). Engineering the largest RNA virus genome as an infectious bacterial artificial chromosome. *Proc. Natl. Acad. Sci. USA.* 97:5516-5521.

Ballesteros, M. L., C. M. Sanchez, and L. Enjuanes. (1997). Two amino acid changes at the N-terminus of transmissible gastroenteritis coronavirus spike protein result in the loss of enteric tropism. *Virology.* 227:378-388.

Baron, M. D., and T. Barrett. (1997). Rescue of rinderpest virus from cloned cDNA. *J. Virol.* 71:1265-1271.

Boyer, J. C., A. L. and Haenni. (1994). Infectious transcripts and cDNA clones of RNA viruses. *Virology.* 198:415-426.

Chang, R. Y., M. A. Hofmann, P. B. Sethna, and D. A. Brian. (1994). A cis-acting function for the coronavirus leader in defective interfering RNA replication. *J. Virol.* 68:8223-8231.

Collins, P. L., M. G. Hill, E. Camargo, H. Grosfeld, R. M. Chanock, and B. R. Murphy. (1995). Production of infectious human respiratory syncytial virus from cloned dCNA confirms an essential role for the transcription elongation factor from the 5' proximal open reading frame of the M2 mRNA in gene expression and provides a capability for vaccine development. *Proc. Natl. Acad. Sci. USA.* 92:11563-11567.

Davis, N. L., L. V. Willis, J. F. Smith, and R. E. Johnston. (1989). In vitro synthesis of infectious Venezuelan equine encephalitis virus RNA from a cDNA clone: analysis of a viable deletion mutant. *Virology.* 171:189-204.

Dubensky, J., T. W., D. A. Driver, J. M. Polo, B. A. Belli, E. M. Latham, C. E. Ibanez, S. Chada, D. Brumm, T. A. Banks, S. J. Mento, D. J. Jolly, and S. M. W. Chang. (1996). Sindbis virus DNA-based expression vectors: utility for in vitro and in vivo gene transfer. *J. Virol.* 70:508-519.

Durbin, A. P., S. L. Hall, J. W. Slew, S. S. Whitehead, P. L. Collins, and B. R. Murphy. (1997). Recovery of infectious human parainfluenza virus type 3 from cDNA. *Virology.* 235:323-332.

Enjuanes, L., S. G. Siddell, and W. J. Spaan. 1998. *Coronaviruses and Arteriviruses.* Plenum Press, New York.

Enjuanes, L., and B. A. M. Van der Zeijst. 1995. Molecular basis of transmissible gastroenteritis coronavirus epidemiology. In *The Coronaviridae.* S. G. Siddell, editor. Plenum Press, New York. 337-376.

Frolov, I., T. A. Hoffman, B. M. Prágai, S. A. Dryga, H. V. Huang, S. Schlesinger, and C. M. Rice. (1996). Alphavirus-based expression vectors: Strategies and applications. *Proc. Natl. Acad. Sci. USA.* 93:11371-11377.

Garcin, D., T. Pelet, P. Calain, L. Roux, J. Curran, and D. Kolakofsky. (1995). A highly recombinogenic system for the recovery of infectious sendai paramyxovirus from cDNA: generation of a novel. *EMBO J.* 14:6087-6094.

Geigenmuller, U., N. H. Ginzton, and S. M. Matsui. (1997). Construction of a genome-length cDNA clone for human astrovirus serotype 1 and synthesis of infectious RNA transcripts. *J. Virol.* 71:1713-1717.

Izeta, A., C. Smerdou, S. Alonso, Z. Penzes, A. Mendez, J. Plana-Duran, and L. Enjuanes. (1999). Replication and packaging of transmissible gastroenteritis coronavirus-derived synthetic minigenomes. *J. Virol.* 73:1535-1545.

Kim, U. -J., H. Shizuya, P. de Jong, B. W. Birren, and M. I. Simon. (1992). Stable propagation of cosmid-sized human DNA inserts in an F-factor based vector. *Nucleic Acids Res.* 20:1083-1085.

Lai, C. -J., B. Zhao, H. Hori, and M. Bray. (1991). Infectious RNA transcribed from stably cloned full-length cDNA of dengue type 4 virus. *Proc. Natl. Acad. Sci. USA.* 88:5139-5143.

Lai, M. M. C., and D. Cavanagh. (1997). The molecular biology of coronaviruses. *Adv. Virus Res.* 48:1-100.

Lai, M. M. C., C. -L. Liao, Y. -J. Lin, and X. Zhang. (1994). Coronavirus: how a large RNA viral genome is replicated and transcribed. *Infect. Agents Dis.* 3:98-105.

Liljeström, P. (1994). Alphavirus expression systems. *Curr. Opin. Biotech.* 5:495-500.

Liljeström, P., and H. Garoff. (1991). A new generation of animal cell expression vectors based on the Semliki Forest virus replicon. *Bio/Technology.* 9:1356-1361.

Luytjes, W., M. Krystal, M. Enami, J. D. Parvin, and P. Palese. (1989). Amplification, expression, and packaging of a foreign gene by influenza virus. *Cell.* 59:1107-1113.

Mandl, C. W., M. Ecker, H. Holzmann, C. Kunz, F. X. Heinz. (1997).Infectious cDNA clones of tick-borne encephalitis virus European subtype prototypic strain Neudoerfl and high virulence strain Hypr. *J. Gen. Virol.* 78:1049-1057.

Maniatis, T., E. F. Fritsh, and J. Sambrook, (1989). *Molecular cloning: a laboratory manual.* Cold Spring Harbour Laboratory Press. New York Méndez, A., C. Smerdou, A. Izeta, F. Gebauer, and L. Enjuanes. (1996). molecular characterization of transmissible gastroenteritis coronavirus defective interfering genomes: packaging and heterogeneity. *Virology.* 217:495-507.

Penzes, Z., A. Izeta, C. Smerdou, A. Mendez, M. L. Ballesteros, and L. Enjuanes. (1999). Complete nucleotide sequence of transmissible gastroenteritis coronavirus strain PUR46-MAD. Submitted for publication Pushko, P., M. Parker, G. V. Ludwing, N. L. Davis, R. E. Johnston, and J. F. Smith. (1997). Replication-helper systems from attenuated Venezuelan equine encephalitis virus: expression of heterologous genes in vitro and immunization against heterologous pathogens in vivo. *Virology.* 239:389-401.

Racaniello, V. R., and D. Baltimore. (1981). Cloned poliovirus cDNA is infectious in mammalian cells. *Science.* 214: 916-919.

Radecke, F., P. Spielhofer, H. Schneider, K. Kaelin, M. Huber, C. Dotsch, G. Christiansen, and M. A. Billeter. (1995). Rescue of measles viruses form cloned DNA. *EMBO J.* 14:5773-5784.

Rice, C. M., A. Grakoui, R. Galler, and T. J. Chambers. (1989). Transcription of infectious yellow fever RNA from full-length cDNA templates produced by in vitro ligation. *New Biologist.* 1:285-296.

Rice, C. N., R. Levis, J. H. Strauss, and H. V. Huang. (1987). Production of infectious RNA transcripts from Sindbis virus cDNA clones: Mapping of lethal mutations, rescue of a temperature-sensitive marker, and in vitro mutagenesis to generate defined mutants. *J. Virol.* 61:3809-3819.

Rice, C. M., and J. H. Strauss. (1981). Synthesis, cleavage, and sequence analysis of DNA complementary to the 26S messenger RNA of Sindbis virus. *J. Mol. Biol.* 150:315-340.

Ruggli, N., J. D. Tratschin, C. Mittelholzer, M. A. Hofmann. (1996). Nucleotide sequence of classical swine fever virus strain Alfort/187 and transciption of infectious RNA from stably cloned full-length cDNA. *J. Virol.* 70:3479-3487.

Sánchez, C. M., G. Jiménez, M. D. Laviada, I. Correa, C. Suñé, M. J. Bullido, F. Gebauer, C. Smerdou, P. Callebaut, J. M. Escribano, and L. Enjuanes. (1990). Antigenic homology among coronaviruses related to transmissible gastroenteritis virus. *Virology.* 174:410-417

Sánchez, C. M., F. Gebauer, C. Suñé, A. Mendez, J. Dopazo, and L. Enjuanes. (1992). Genetic evolution and tropism of transmissible gastroenteritis coronaviruses. *Virology.* 190: 92-105.

Sánchez, C. M., A. Izeta, J. M. Sanchez-Morgado, S. Alonso, I. Sola, M. Balasch, J. Plana-Durán, and L. Enjuanes. (1999). Targeted recombination demonstrates that the spike gene of transmissible gastroenteritis coronavirus is a determinant of its enteric tropism and virulence. *J. Virol.* 73:7607-7618.

Sawicki, S. G., and D. L. Sawicki. (1990). Coronavirus transcription: subgenomic mouse hepatitis virus replicative intermediates function in RNA synthesis. *J. Virol.* 64:1050-1056.

Schnell, M. J., T. Mebatsion, and K. -K. Conzelmann. (1994). Infectious rabies viruses from cloned cDNA. *EMBO J.* 13:4195-4203.

Sethna, P. B., S. -L. Hung, and D. A. Brian. (1989). Coronavirus subgenomic minus-strand RNAs and the potential for mRNA replicons. *Proc. Natl. Acad. Sci. USA.* 86:5626-5630.

Shizuya, H., B. Birren, U. -J. Kim, V. Mancino, T. Slepak, Y. Tachiuri, and M. Simon. (1992). Cloning and stable maintenance of 300-kilobase-pair fragments of human DNA in *Escherichia coli* using an F-factor-based vector. *Proc. Natl. Acad. Sci. USA.* 89:8794-8797.

Siddell, S. G. 1995. *The Coronaviridae.* Plenum Press, New York. 418 pp.

Smerdou, C., and P. Liljestrom. (1999). Non-viral amplification systems for gene transfer: vectors based on alphaviruses. *Curr. Opin. Mol. Therap.* 1:244-251.

Taniguchi, M., and F. A. P. Miller. (1978). Specific suppressive factors produced by hybridomas derived from the fusion of enriched suppressor T cells and A T lymphoma cell line. *J. Exp. Med.* 148:373-382.

van der Most, R. G., and W. J. M. Spaan. 1995. Coronavirus replication, transcription, and RNA recombination. *In The Coronaviridae.* S. G. Siddell, editor. Plenum Press, New York. 11-31.

Wang, K., C. Boysen, H. Shizuya, M. I. Simon, and L. Hood. (1997). Complete nucleotide sequence of two generations of a bacterial artificial chromosome cloning vector. *BioTechniques.* 23:992-994.

Woo, S. -S., J. Jiang, B. S. Gill, A. H. Paterson, and R. A. Wing. (1994). Construction and characterization of a bacterial artificial chromosome library of Sorghum bicolor. *Nucleic Acids Res.* 22:4922-4931.

Zhang, X., C. L. Liao, and N. M. C. Lai. (1994). Coronavirus leader RNA regulates and initiates subgenomic mRNA transcription both in trans and in cis. *J. Virol.* 68:4738-4746.

The invention claimed is:

1. A bacterial artificial chromosome construct comprising a nucleic acid sequence that directs formation of a recombinant coronavirus upon introduction into a cell.

2. The artificial chromosome construct of claim 1, wherein said artificial chromosome or said nucleic acid sequence further comprises a heterologous nucleic acid sequence.

3. The artificial chromosome construct of claim 2, wherein said heterologous nucleic acid sequence encodes a therapeutic gene product.

4. The artificial chromosome construct of claim 3, wherein said therapeutic gene product is a protein, a peptide, or an epitope.

5. The artificial chromosome construct of claim 3, wherein said therapeutic gene product is selected from the group consisting of a ribozyme, an antigen from an infectious agent, a molecule interfering with the replication of an infectious agent, an antibody, an immune modulator, a cytokine, an immunoenhancer, an anti-inflammatory compound, an enzyme, a substance that potentiates subpopulations of helper T-cells, cellular necrosis factor, and substances that provoke cellular immunity.

* * * * *